(12) United States Patent
Or et al.

(10) Patent No.: US 8,178,531 B2
(45) Date of Patent: May 15, 2012

(54) ANTIVIRAL AGENTS

(75) Inventors: Yat Sun Or, Watertown, MA (US);
Guoqiang Wang, Belmont, MA (US);
Xuri Gao, Newton, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 13/033,015

(22) Filed: Feb. 23, 2011

(65) Prior Publication Data

US 2011/0218175 A1 Sep. 8, 2011

Related U.S. Application Data

(60) Provisional application No. 61/307,214, filed on Feb. 23, 2010.

(51) Int. Cl.
*A61K 31/506* (2006.01)
*A61K 31/496* (2006.01)
*A61K 31/4436* (2006.01)
*A61K 31/443* (2006.01)
*A61K 31/4433* (2006.01)
*C07D 413/14* (2006.01)
*C07D 401/14* (2006.01)
*C07D 213/30* (2006.01)
*C07D 211/58* (2006.01)
*C07D 261/20* (2006.01)
*C07D 405/14* (2006.01)

(52) U.S. Cl. ............ 514/235.8; 514/253.09; 514/266.22; 514/316; 514/318; 514/321; 514/323; 514/326; 544/130; 544/328; 544/364; 546/175; 546/187; 546/194; 546/198; 546/209; 546/210

(58) Field of Classification Search .................. None
See application file for complete search history.

(56) References Cited

U.S. PATENT DOCUMENTS

| | | | |
|---|---|---|---|
| 5,935,982 | A | 8/1999 | Dykstra et al. |
| 7,141,574 | B2 | 11/2006 | Beaulieu et al. |
| 2006/0003942 | A1 | 1/2006 | Tung et al. |
| 2006/0058317 | A1 | 3/2006 | Gravestock et al. |
| 2006/0276511 | A1 | 12/2006 | Serrano-Wu et al. |
| 2007/0299068 | A1 | 12/2007 | Karp et al. |
| 2008/0044380 | A1 | 2/2008 | Bachand et al. |
| 2009/0004111 | A1 | 1/2009 | Rice et al. |
| 2009/0202478 | A1 | 8/2009 | Bachand et al. |
| 2009/0202483 | A1 | 8/2009 | Bachand et al. |
| 2009/0226398 | A1 | 9/2009 | Leivers et al. |
| 2009/0317360 | A1 | 12/2009 | Rai et al. |
| 2010/0221214 | A1 | 9/2010 | Or et al. |
| 2010/0221215 | A1 | 9/2010 | Qiu et al. |
| 2010/0221216 | A1 | 9/2010 | Or et al. |
| 2010/0226882 | A1 | 9/2010 | Or et al. |
| 2010/0226883 | A1 | 9/2010 | Qiu et al. |
| 2010/0233120 | A1 | 9/2010 | Bachand et al. |
| 2010/0233122 | A1 | 9/2010 | Qiu et al. |
| 2010/0260708 | A1 | 10/2010 | Belema et al. |
| 2010/0260715 | A1 | 10/2010 | Or et al. |
| 2010/0266543 | A1 | 10/2010 | Qiu et al. |
| 2010/0305117 | A1 | 12/2010 | Herdewijn et al. |
| 2010/0310512 | A1 | 12/2010 | Guo et al. |
| 2010/0316607 | A1 | 12/2010 | Or et al. |
| 2011/0008288 | A1 | 1/2011 | Or et al. |
| 2011/0064695 | A1 | 3/2011 | Qiu et al. |
| 2011/0064696 | A1 | 3/2011 | Or et al. |
| 2011/0064697 | A1 | 3/2011 | Qiu et al. |
| 2011/0064698 | A1 | 3/2011 | Or et al. |
| 2011/0070196 | A1 | 3/2011 | Qiu et al. |
| 2011/0070197 | A1 | 3/2011 | Or et al. |

FOREIGN PATENT DOCUMENTS

| | | |
|---|---|---|
| WO | 2006133326 A1 | 12/2006 |
| WO | 2008021927 A2 | 2/2008 |
| WO | 2008021928 A2 | 2/2008 |
| WO | 2008021936 A2 | 2/2008 |
| WO | 2008144380 A1 | 11/2008 |
| WO | 2009020825 A1 | 2/2009 |
| WO | 2009020828 A1 | 2/2009 |
| WO | 2009102318 A1 | 8/2009 |
| WO | 2009102325 A1 | 8/2009 |

(Continued)

OTHER PUBLICATIONS

Bressanelli, et al., "Crystal Structure of the RNA-dependent RNA Polymerase of Hepatitis C Virus," PNAS, 96 (23):13034-13039, 1999. Sofia, "R7128, A Potent and Selective Nucleoside Inhibitor of HCV NS5B Polymerase: An Overview of Clinical Efficacy and Progress Toward Second Generation Inhibitors," Pharmasset, CHI:HCV Drug Discovery, 2008.

*Primary Examiner* — Rebecca Anderson
*Assistant Examiner* — Alicia L Otton
(74) *Attorney, Agent, or Firm* — Edgar W. Harlan; Carolyn S. Elmore; Elmore Patent Law Group, P.C.

(57) ABSTRACT

The present invention relates to antiviral compounds of formula (I),

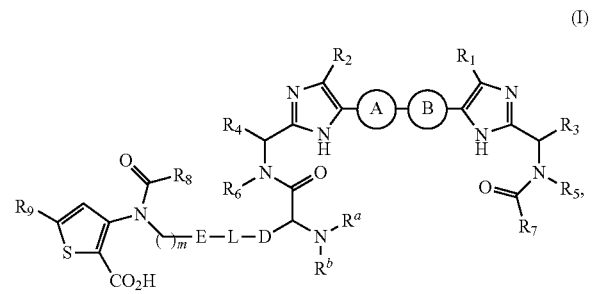

compositions containing these compounds, processes for their preparation, intermediates in their synthesis, and their use as therapeutics for prevention of organ transplantation rejection, the treatment of immune disorders and inflammation, and treatment of viral (particularly hepatitis C viral) infection.

6 Claims, No Drawings

FOREIGN PATENT DOCUMENTS

| | | | |
|---|---|---|---|
| WO | 2009102568 A1 | 8/2009 |
| WO | 2009102633 A1 | 8/2009 |
| WO | 2009102694 A1 | 8/2009 |
| WO | 2010014744 A1 | 2/2010 |
| WO | 2010017401 A1 | 2/2010 |
| WO | 2010039793 A1 | 4/2010 |
| WO | 2010065668 A1 | 6/2010 |
| WO | 2010065674 A1 | 6/2010 |
| WO | 2010065681 A1 | 6/2010 |
| WO | 2010096302 A1 | 8/2010 |
| WO | 2010096777 A1 | 8/2010 |
| WO | 2010111483 A1 | 9/2010 |
| WO | 2010111534 A1 | 9/2010 |
| WO | 2010111673 A1 | 9/2010 |
| WO | 2010117635 A1 | 10/2010 |
| WO | 2010117704 A1 | 10/2010 |
| WO | 2010117977 A1 | 10/2010 |
| WO | 2010120621 A1 | 10/2010 |
| WO | 2010120935 A1 | 10/2010 |
| WO | 2010122162 A1 | 10/2010 |
| WO | 2010132538 A1 | 11/2010 |
| WO | 2010138368 A1 | 12/2010 |
| WO | 2010138488 A1 | 12/2010 |
| WO | 2010138790 A1 | 12/2010 |
| WO | 2010138791 A1 | 12/2010 |
| WO | 2010144646 A2 | 12/2010 |
| WO | 2011004276 A1 | 1/2011 |
| WO | 2011009084 A2 | 1/2011 |
| WO | 2011015657 A1 | 2/2011 |
| WO | 2011015658 A1 | 2/2011 |
| WO | 2011026920 A1 | 3/2011 |
| WO | 2011028596 A1 | 3/2011 |

ANTIVIRAL AGENTS

RELATED APPLICATION

This application claims the benefit of U.S. Provisional Application No. 61/307,214, filed Feb. 23, 2010. The entire teachings of the above application are incorporated herein by reference.

TECHNICAL FIELD

The present invention relates to novel antiviral agents, compositions containing them, processes for their preparation, intermediates in their synthesis, and their use as therapeutics for prevention of organ transplantation rejection, the treatment of immune disorders and inflammation, and treatment of viral (particularly hepatitis C viral) infection.

BACKGROUND OF THE INVENTION

Infection with HCV is a major cause of human liver disease throughout the world. In the US, an estimated 4.5 million Americans are chronically infected with HCV. Although only 30% of acute infections are symptomatic, greater than 85% of infected individuals develop chronic, persistent infection. Treatment costs for HCV infection have been estimated at $5.46 billion for the US in 1997. Worldwide over 200 million people are estimated to be infected chronically. HCV infection is responsible for 40-60% of all chronic liver disease and 30% of all liver transplants. Chronic HCV infection accounts for 30% of all cirrhosis, end-stage liver disease, and liver cancer in the U.S. The CDC estimates that the number of deaths due to HCV will minimally increase to 38,000/year by the year 2010.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Due to the high degree of variability in the viral surface antigens, existence of multiple viral genotypes, and demonstrated specificity of immunity, the development of a successful vaccine in the near future is unlikely. Only two approved therapies for HCV infection are currently available. The original treatment regimen generally involves a 3-12 month course of intravenous interferon-α(IFN-α), while a new approved second-generation treatment involves co-treatment with IFN-α and the general antiviral nucleoside mimics like ribavirin. Both of these treatments suffer from interferon related side effects as well as low efficacy against HCV infections. There exists a need for the development of effective antiviral agents for treatment of HCV infection due to the poor tolerability and disappointing efficacy of existing therapies.

First identified by molecular cloning in 1989 (Choo, Q-L et al (1989) Science 244:359-362), HCV is now widely accepted as the most common causative agent of post-transfusion non-A, non-B hepatitis (NANBH) (Kuo, G et al (1989) Science 244:362-364). Due to its genome structure and sequence homology, this virus was assigned as a new genus in the Flaviviridae family. Like the other members of the Flaviviridae, such as flaviviruses (e.g. yellow fever virus and Dengue virus types 1-4) and pestiviruses (e.g. bovine viral diarrhea virus, border disease virus, and classic swine fever virus) (Choo, Q-L et al (1989) Science 244:359-362; Miller, R. H. and R. H. Purcell (1990) Proc. Natl. Acad. Sci. USA 87:2057-2061), HCV is an enveloped virus containing a single strand RNA molecule of positive polarity. The HCV genome is approximately 9.6 kilobases (kb) with a long, highly conserved, noncapped 5' nontranslated region (NTR) of approximately 340 bases which functions as an internal ribosome entry site (IRES) (Wang C Y et al 'An RNA pseudoknot is an essential structural element of the internal ribosome entry site located within the hepatitis C virus 5' noncoding region' RNA—A Publication of the RNA Society. 1(5): 526-537, 1995 July). This element is followed by a region which encodes a single long open reading frame (ORF) encoding a polypeptide of ~3000 amino acids comprising both the structural and nonstructural viral proteins.

Upon entry into the cytoplasm of the cell, this RNA is directly translated into a polypeptide of ~3000 amino acids comprising both the structural and nonstructural viral proteins. This large polypeptide is subsequently processed into the individual structural and nonstructural proteins by a combination of host and virally-encoded proteinases (Rice, C. M. (1996) in B. N. Fields, D. M. Knipe and P. M. Howley (eds) Virology $2^{nd}$ Edition, p 931-960; Raven Press, N.Y.). There are three structural proteins, C, E1 and E2. The P7 protein is of unknown function and is comprised of a highly variable sequence. There are several non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease. NS5A is a membrane-anchored phosphoprotein that is observed in basally phosphorylated (56 kDa) and hyperphosphorylated (58 kDa) forms. While its function has not fully been elucidated, NS5A is believed to be important in viral replication. The NS5B protein (591 amino acids, 65 kDa) of HCV (Behrens, S. E. et at (1996) EMBO J. 151 2-22), encodes an RNA-dependent RNA polymerase (RdRp) activity and contains canonical motifs present in other RNA viral polymerases. The NS5B protein is fairly well conserved both intra-typically (~95-98% amino acid (aa) identity across 1b isolates) and inter-typically (~85% aa identity between genotype 1a and 1b isolates). The essentiality of the HCV NS5B RdRp activity for the generation of infectious progeny virions has been formally proven in chimpanzees (A. A. Kolykhalov et al. (2000) Journal of Virology, 74(4): 2046-2051). Thus, inhibition of NS5B RdRp activity (inhibition of RNA replication) is predicted to be useful to treat HCV infection.

Following the termination codon at the end of the long ORF, there is a 3' NTR which roughly consists of three regions: an ~40 base region which is poorly conserved among various genotypes, a variable length poly(U)/polypyrimidine tract, and a highly conserved 98 base element also called the "3' X-tail" (Kolykhalov, A. et al (1996) J. Virology 70:3363-3371; Tanaka, T. et al (1995) Biochem Biophys. Res. Commun. 215744-749; Tanaka, T. et al (1996) J. Virology 70:3307-3312; Yamada, N. et al (1996) Virology 223:255-261). The 3' NTR is predicted to form a stable secondary structure which is essential for HCV growth in chimps and is believed to function in the initiation and regulation of viral RNA replication.

Compounds useful for treating HCV-infected patients are desired which selectively inhibit HCV viral replication. In particular, compounds which are effective to inhibit the function of the NS5A protein and/or NS5B protein are desired.

SUMMARY OF THE INVENTION

The present invention relates to novel antiviral compounds represented herein below, pharmaceutical compositions comprising such compounds, and methods for the treatment or prophylaxis of viral (particularly HCV) infection in a subject in need of such therapy with said compounds. Compounds of the present invention interfere with the life cycle of the hepatitis C virus and are also useful as antiviral agents.

In its principal embodiment, the present invention provides a compound of formula (I):

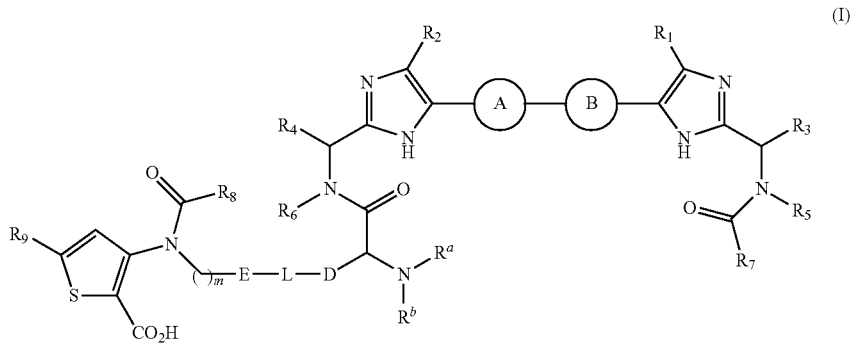

(I)

or a pharmaceutically acceptable salt, ester or prodrug thereof, where:

Ring A and ring B are each independently selected from:
  a) Phenyl;
  b) Substituted phenyl;
  c) Six membered heteroaryl containing one, two or three nitrogen atoms;
  d) Substituted six membered heteroaryl containing one, two or three nitrogen atoms;

$R_1$ and $R_2$ are each independently selected from:
  a) Hydrogen;
  b) Deuterium;
  c) Halogen;
  d) $R_{11}$, where $R_{11}$ is selected from:
    1) $C_1$-$C_{12}$ alkyl;
    2) Substituted $C_1$-$C_{12}$ alkyl;
    3) $C_2$-$C_{12}$ alkenyl;
    4) Substituted $C_2$-$C_{12}$ alkenyl;
    5) $C_2$-$C_{12}$ alkynyl;
    6) Substituted $C_2$-$C_{12}$ alkynyl;
    7) $C_3$-$C_{12}$ cycloalkyl;
    8) Substituted $C_3$-$C_{12}$ cycloalkyl;
    9) Aryl;
    10) Substituted aryl;
    11) Heterocycloalkyl;
    12) Substituted heterocycloalkyl;
    13) Heteroaryl; and
    14) Substituted heteroaryl;
  e) —C(O)O$R_{12}$, where $R_{12}$ is selected from hydrogen or $R_{11}$ where $R_{11}$ as previously defined;
  f) —C(O) $R_{12}$, where $R_{12}$ is as previously defined;
  g) —C(O)N($R_{13}$)($R_{14}$), where $R_{13}$ and $R_{14}$ are independently selected from $R_{12}$ and $R_{12}$ is as previously defined or $R_{13}$ and $R_{14}$ combined together with the N which attached to is substituted or unsubstituted heterocycloalkyl;
  h) —C(O)S$R_{12}$, where $R_{12}$ is as previously defined;
  i) —C(S)O$R_{12}$, where $R_{12}$ is as previously defined;
  j) —C(S)S $R_{12}$, where $R_{12}$ is as previously defined;
  k) —O$R_{12}$, where $R_{12}$ is as previously defined;
  l) —S$R_{12}$, where $R_{12}$ is as previously defined; and
  m) —N$R_{13}R_{14}$, where $R_{13}$ and $R_{14}$ are as previously defined;

$R_3$, $R_4$, $R_5$ and $R_6$ are independently selected from:
  a) Hydrogen;
  b) Deuterium;
  c) $C_1$-$C_{12}$ alkyl;
  d) Substituted $C_1$-$C_{12}$ alkyl;
  e) $C_2$-$C_{12}$ alkenyl;
  f) Substituted $C_2$-$C_{12}$ alkenyl;
  g) $C_2$-$C_{12}$ alkynyl;
  h) Substituted $C_2$-$C_{12}$ alkynyl;
  i) $C_3$-$C_{12}$ cycloalkyl;
  j) Substituted $C_3$-$C_{12}$ cycloalkyl;
  k) Aryl;
  l) Substituted aryl;
  m) Heterocycloalkyl;
  n) Substituted heterocycloalkyl;
  o) Heteroaryl;
  p) Substituted heteroaryl;
or $R_3$ and $R_5$, together with the nitrogen atom and the carbon atom to which they are attached, and/or $R_4$ and $R_6$, together with the nitrogen atom and the carbon atom to which they are attached, independently form a substituted or unsubstituted heterocycloalkyl;

$R^a$ and $R^b$ are independently selected from:
  a) Hydrogen;
  b) $R_{11}$;
  c) —C(O)O—$R_{11}$, where $R_{11}$ is as previously defined;
  d) —C(O)NH$R_{11}$, where $R_{11}$ is as previously defined;
  or $R^a$ and $R^b$ together with the nitrogen atom to which they are attached form a substituted or unsubstituted heterocycloalkyl;

$R_7$ is selected from:
  a) $R_{11}$, where $R_{11}$ is as previously defined;
  b) —O$R_{11}$, where $R_{11}$ is as previously defined;
  c) —S$R_{11}$, where $R_{11}$ is as previously defined; and
  d) —N$R_{13}R_{14}$, where $R_{13}$ and $R_{14}$ are as previously defined;

D is selected from:
  a) $C_1$-$C_{12}$ alkylene containing 0, 1, 2 or 3 heteroatoms independently selected from O, S and N;

b) Substituted $C_1$-$C_{12}$ alkylene containing 0, 1, 2 or 3 heteroatoms independently selected from O, S and N;
c) $C_2$-$C_{12}$ alkenylene containing 0, 1, 2 or 3 heteroatoms independently selected from O, S and N;
d) Substituted $C_2$-$C_{12}$ alkenylene containing 0, 1, 2 or 3 heteroatoms independently selected from O, S and N;
e) $C_2$-$C_{12}$ alkynylene containing 0, 1, 2 or 3 heteroatoms independently selected from O, S and N;
f) Substituted $C_2$-$C_{12}$ alkynylene containing 0, 1, 2 or 3 heteroatoms independently selected from O, S and N;
g) $C_3$-$C_{12}$ cycloalkylene;
h) Substituted $C_3$-$C_{12}$ cycloalkylene;
i) Heterocycloalkylene; and
j) Substituted heterocycloalkylene;

E is absent or selected from:
a) $C_1$-$C_{12}$ alkylene;
b) Substituted $C_1$-$C_{12}$ alkylene;
c) $C_3$-$C_{12}$ cycloalkylene;
d) $C_3$-$C_{12}$ cycloalkylene-M-, where M is selected from optionally substituted $C_1$-$C_{12}$ alkylene, or optionally substituted $C_2$-$C_{12}$ alkenylene, or optionally substituted $C_2$-$C_{12}$ alkynylene, and optionally substituted $C_3$-$C_{12}$ cycloalkylene, each of which contains 0, 1, 2 or 3 heteroatoms independently selected from O, S and N;
e) Substituted $C_3$-$C_{12}$ cycloalkylene;
f) Substituted $C_3$-$C_{12}$ cycloalkylene-M, where M is as previously defined;
g) Heterocycloalkylene;
h) Heterocycloalkylene-M-, where M is as previously defined;
i) Substituted heterocycloalkylene; and
j) Substituted heterocycloalkylene-M-, where M is as previously defined;

L is absent, or selected from:
a) —O—;
b) —N($R_{12}$)—, where $R_{12}$ is as previously defined;
c) —N(C(O)$R_{11}$)—, where $R_{11}$ is as previously defined;
d) —N(C(O)O$R_{11}$)—, where $R_{11}$ is as previously defined;
e) —S(O)$_n$—, where n=0, 1, or 2;
f) —C(O)—;
g) —C(O)NH—;
h) —OC(O)NH—;
i) —OC(S)NH—;
j) —SC(S)NH—;
k) —NHC(O)NH—;
l) —NHC(S)NH—;
m) —O-M-, where M is as previously defined;
n) —O-M-OC(O)NH—, where M is as previously defined;
o) —S-M-OC(O)NH—, where M is as previously defined;
p) —S(O)$_n$-M-, where n=0, or 1, or 2 and M is as previously defined;
q) —OC(O)NH-M-, where M is as previously defined;
r) —OC(S)NH-M-, where M is as previously defined;
s) —NHC(O)NH-M-, where M is as previously defined;
t) —NHC(S)NH-M-, where M is as previously defined;

$R_8$ is $R_{11}$, where $R_{11}$ is as previously defined;
$R_9$ is selected from:
a) Aryl;
b) Substituted aryl;
c) Heteroaryl; or
d) Substituted heteroaryl;
m is 0, 1, 2, 3 or 4.

In embodiments in which $R_3$ and $R_5$, together with the nitrogen atom and the carbon atom to which they are attached, and/or $R_4$ and $R_6$, together with the nitrogen atom and the carbon atom to which they are attached form a substituted or unsubstituted heterocycloalkyl, suitable substituted or unsubstituted heterocycloalkyl groups include, but are not limited to:

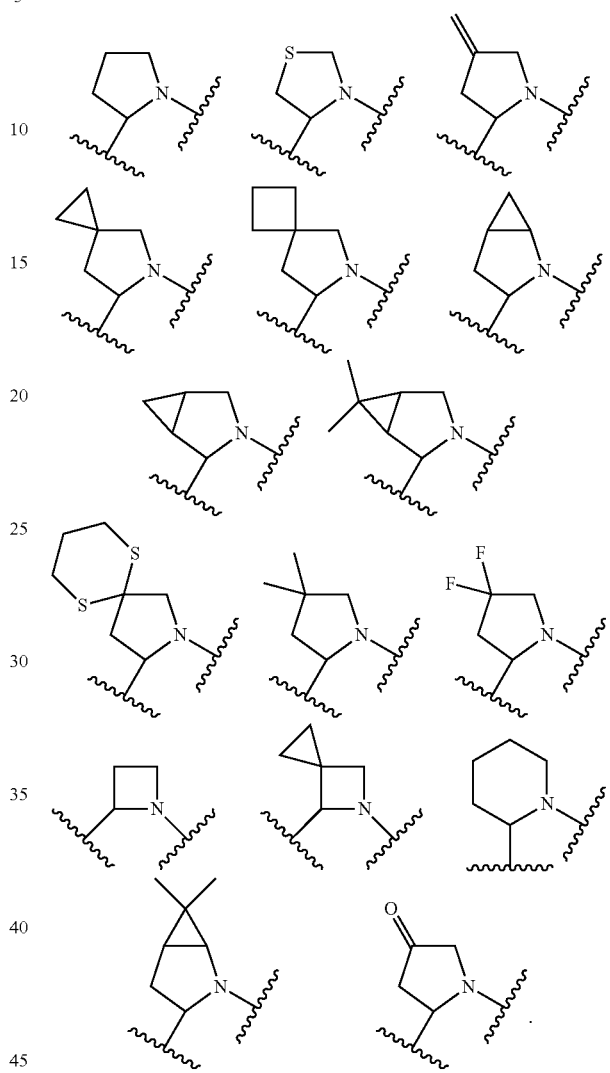

In another embodiment, the present invention provides the use of antiviral agents for the treatment of, with or without the concurrent use of other drugs, organ transplantation rejections, immune disorders, and inflammation including, but not limited to, indications such as rheumatoid arthritis, psoriasis, inflammatory bowel diseases, chronic obstructive pulmonary disease, allergic rhinitis, and asthma.

In yet another embodiment, the present invention provides a pharmaceutical composition comprising a therapeutically effective amount of a compound or combination of compounds of the present invention, or a pharmaceutically acceptable salt form, prodrug, salt of a prodrug, stereoisomer, tautomer, solvate, or combination thereof, in combination with a pharmaceutically acceptable carrier or excipient.

In still another embodiment, the present invention provides a method of inhibiting the replication of an RNA-containing virus comprising contacting said virus with a therapeutically effective amount of a compound or a combination of compounds of the present invention, or a pharmaceutically acceptable salt, prodrug, salt of a pro drug, stereoisomer, tautomer, solvate, or combination thereof. Particularly, this invention is directed to methods of inhibiting the replication of hepatitis C virus.

In yet another embodiment, the present invention provides a method of treating or preventing infection caused by an RNA-containing virus comprising administering to a patient in need of such treatment a therapeutically effective amount of a compound or combination of compounds of the present invention, or a pharmaceutically acceptable salt form, prodrug, salt of a prodrug, stereoisomer, or tautomer, solvate, or combination thereof. Particularly, this invention is directed to methods of treating or preventing infection caused by hepatitis C virus.

Yet another embodiment of the present invention provides the use of a compound or combination of compounds of the present invention, or a therapeutically acceptable salt form, prodrug, salt of a prodrug, stereoisomer or tautomer, solvate, or combination thereof, as defined hereinafter, in the preparation of a medicament for the treatment or prevention of infection caused by RNA-containing virus, specifically hepatitis C virus (HCV).

DETAILED DESCRIPTION OF THE INVENTION

In a first embodiment of the present invention is a compound of formula (I) as illustrated above, or a pharmaceutically acceptable salt, ester or prodrug thereof.

Representative subgenera of the present invention include:
Compounds of formula (I) which are represented by the formula (II),

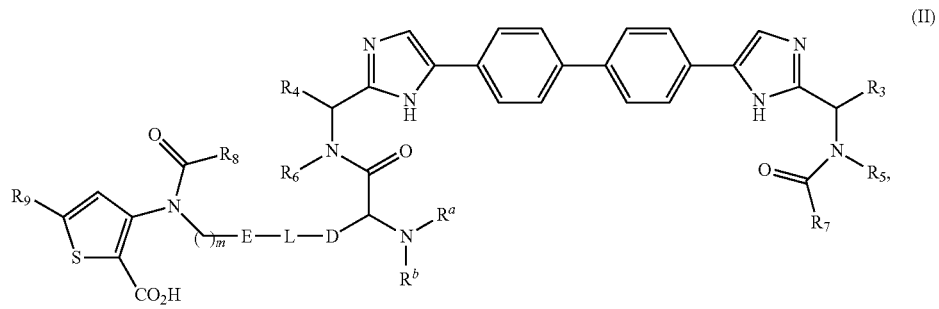

wherein $R_3$, $R_4$, $R_5$, $R_6$, $R_7$, $R_8$, $R_9$, $R^a$, $R^b$, m, E, L, and D are as defined in formula (I);

Compounds of formula (I) which are represented by the formula (III),

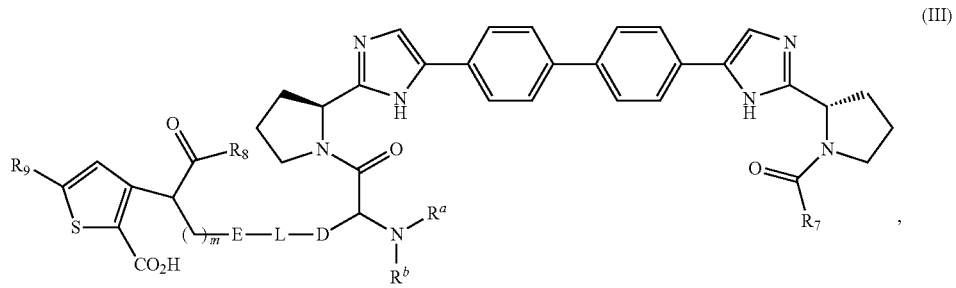

wherein $R_7$, $R_8$, $R_9$, $R^a$, $R^b$, m, E, L, and D are as defined in formula (I);

Compounds of formula (I) which are represented by the formula (IV),

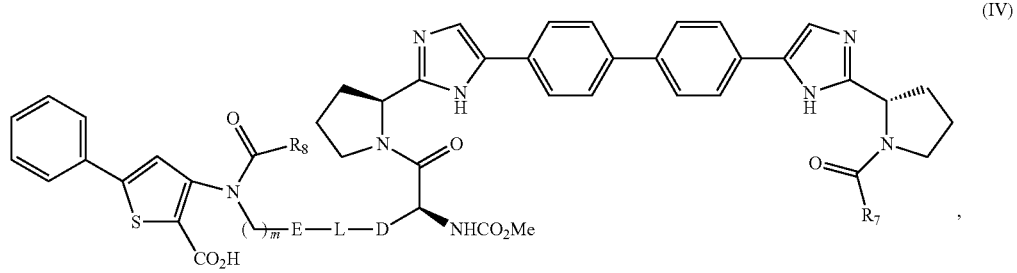

wherein $R_7$, $R_8$, m, E, L, and D are as defined in formula (I).

Representative compounds of the present invention are those of formula (V):
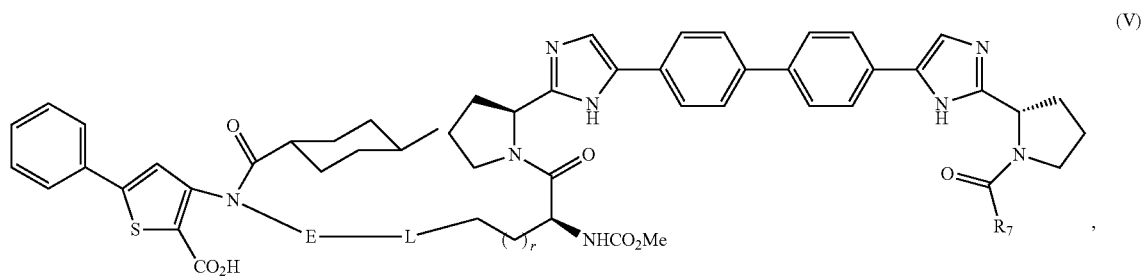
wherein:
E is selected from:
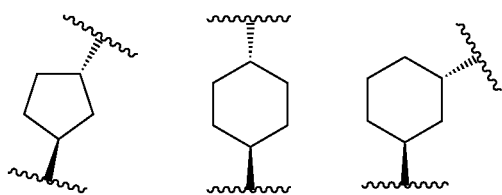
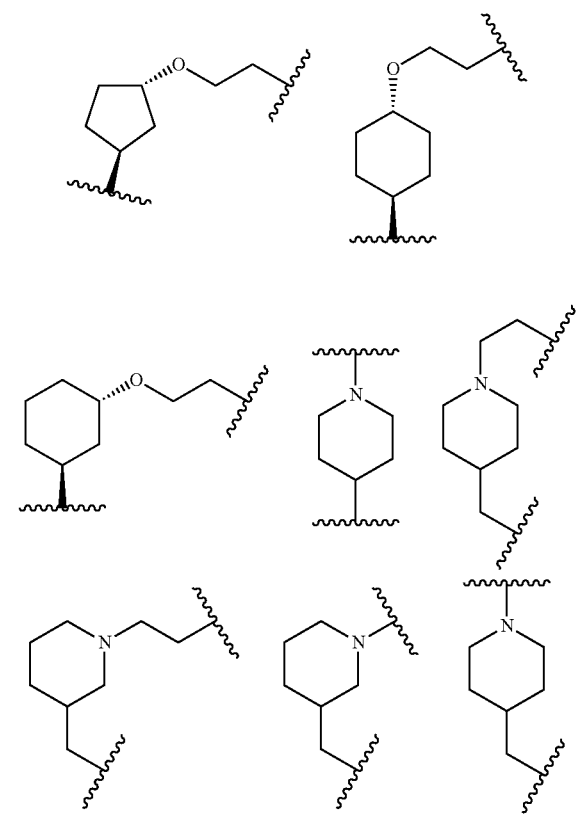
L is selected from: —N(Me)-; —NH—; —N(Boc)-; —N(Ac)—; —OC(O)NH—, —SCH$_2$CH$_2$OC(O)NH—, —OCH$_2$CH$_2$OC(O)NH—;
r is 0, 1, 2, 3, 4 or 5; and
R$_7$C(O)— is selected from the groups set forth in Table 1:
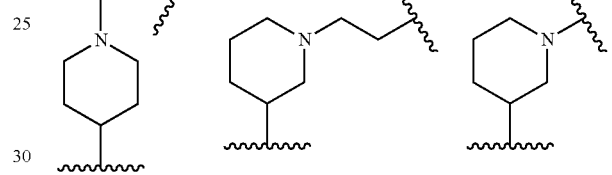

TABLE 1-continued

| Entry | R₇-C(O)- group |
|---|---|
| 5 | CH₃CH₂-CH(OH)-C(O)- |
| 6 | CH₃CH₂-C(O)- |
| 7 | CH₃O-CH₂-C(O)- |
| 8 | (CH₃)₂N-C(O)- |
| 9 | CH₃O-C(O)- |
| 10 | CH₃-C(O)-CH₂CH₂-C(O)- |
| 11 | (CH₃)₂CH-CH(OH)-C(O)- |
| 12 | CH₂=CH-CH₂CH₂-C(O)- |
| 13 | cyclopropyl-C(O)- |
| 14 | 1-(CF₃)-cyclopropyl-C(O)- |
| 15 | 1-(OH)-cyclopropyl-C(O)- |
| 16 | Ph-C(O)- |
| 17 | Ph-CH₂-C(O)- |
| 18 | cyclopropyl-CH₂-C(O)- |
| 19 | Ph-C(CH₃)(OH)-C(O)- |
| 20 | Ph-CH(OMe)-C(O)- |
| 21 | Ph-CH(OH)-C(O)- |
| 22 | pyridin-3-yl-CH₂-C(O)- |
| 23 | pyridin-4-yl-CH₂-C(O)- |
| 24 | Ph-CH₂-CH(OH)-C(O)- |
| 25 | tetrahydrofuran-2-yl-C(O)- |

TABLE 1-continued

| Entry | R₇ group |
|---|---|
| 26 | 2-tetrahydrofuranyl-C(O)- |
| 27 | 3-tetrahydrofuranyl-C(O)- |
| 28 | (1-methylpiperidin-4-yl)-C(O)- |
| 29 | (tetrahydropyran-4-yl)-C(O)- |
| 30 | morpholin-4-yl-C(O)- |
| 31 | trans-4-(Boc-amino)cyclohexyl-C(O)- |
| 32 | cis-4-(Boc-amino)cyclohexyl-C(O)- |
| 33 | (1-Boc-piperidin-4-yl)-C(O)- |
| 34 | 4-(diethylamino)cyclohexyl-C(O)- |
| 35 | 4-(methoxycarbonylamino)cyclohexyl-C(O)- |
| 36 | (4-methylpiperazin-1-yl)-C(O)- |
| 37 | 2-(piperidin-1-ylmethyl)phenyl-CH₂-C(O)- |
| 38 | 2-(pyrrolidin-1-ylmethyl)phenyl-CH₂-C(O)- |
| 39 | 2-((dimethylamino)methyl)phenyl-CH₂-C(O)- |
| 40 | 2-((4-methylpiperazin-1-yl)methyl)phenyl-CH₂-C(O)- |
| 41 | 2-(morpholin-4-ylmethyl)phenyl-CH₂-C(O)- |

TABLE 1-continued

| Entry | R₇ group |
|---|---|
| 42 | methyl carbamate trans-cyclohexyl ketone |
| 43 | thiazol-4-yl ketone |
| 44 | oxazol-2-yl ketone |
| 45 | oxazol-5-yl ketone |
| 46 | (1H-imidazol-5-yl)methyl ketone |
| 47 | 1H-imidazol-5-yl ketone |
| 48 | 1-methyl-1H-imidazol-5-yl ketone |
| 49 | (1H-tetrazol-5-yl)methyl ketone |
| 50 | 2-fluorophenyl ketone |
| 51 | 4-(dimethylamino)phenyl ketone |
| 52 | pyridin-4-yl ketone |
| 53 | pyridin-3-yl ketone |
| 54 | pyridin-2-yl ketone |
| 55 | (S)-2-methoxy-2-phenyl ketone |
| 56 | 2-methoxy-2-phenyl-3,3,3-trifluoro ketone |
| 57 | 2,2-diphenyl ketone |
| 58 | 2-methyl-2-(pyridin-3-yl) ketone |
| 59 | (R)-2-hydroxy-2-(3-fluoropyridin-2-yl) ketone |

TABLE 1-continued
| Entry | |
|---|---|
| 60 | 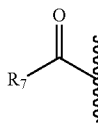 |
| 61 | 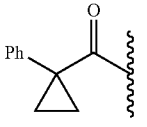 |
| 62 | 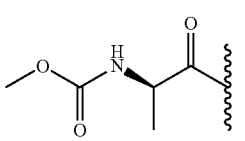 |
| 63 | 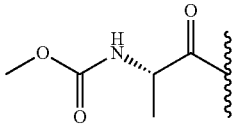 |
| 64 | 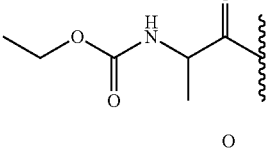 |
| 65 | 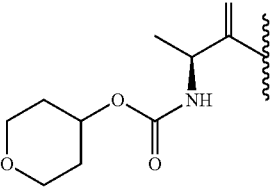 |
| 66 | 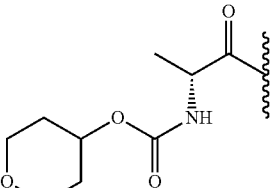 |
| 67 | 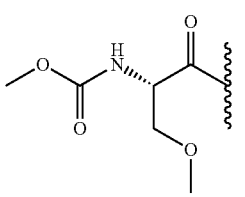 |
| 68 | 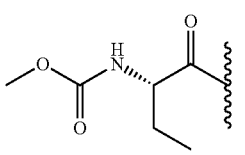 |
TABLE 1-continued
| Entry | |
|---|---|
| 69 | 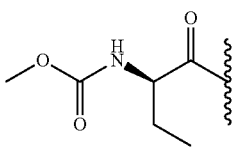 |
| 70 | 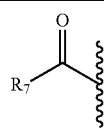 |
| 71 | 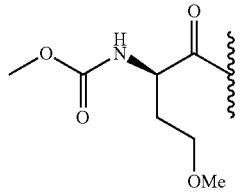 |
| 72 | 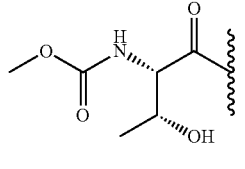 |
| 73 | 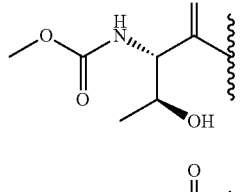 |
| 74 | 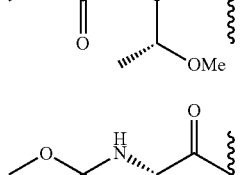 |
| 75 | 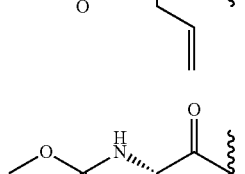 |
| 76 | 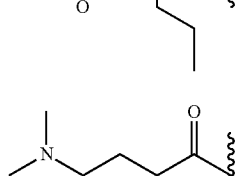 |

TABLE 1-continued
| Entry | |
|---|---|
| 77 | 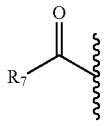 |
| 78 | 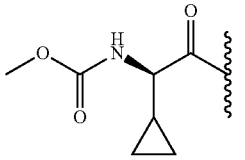 |
| 79 | 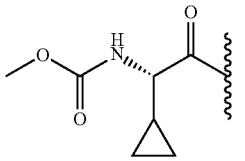 |
| 80 | 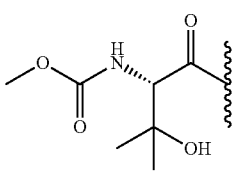 |
| 81 | 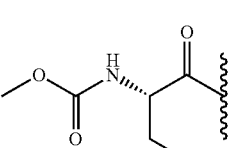 |
| 82 | 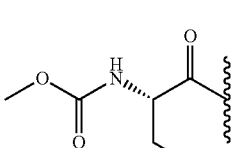 |
| 83 | 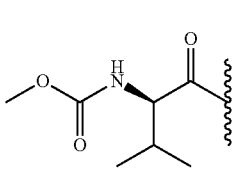 |
| 84 | 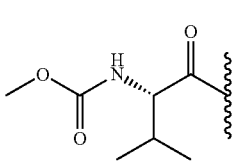 |
| 85 | 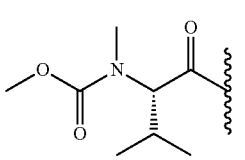 |
| 86 | 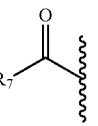 |
| 87 | 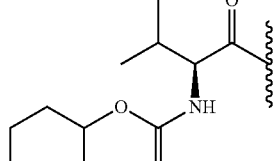 |
| 88 | 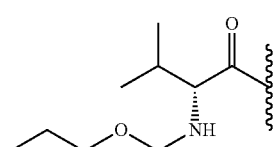 |
| 89 | 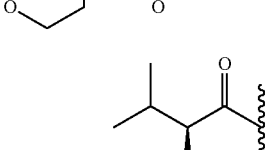 |
| 90 | 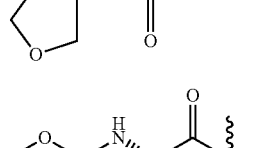 |
| 91 | 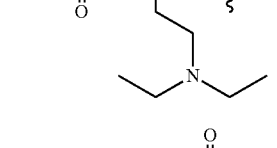 |

TABLE 1-continued
| Entry | R₇–C(=O)– structure |
|---|---|
| 92 | 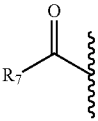 |
| 93 | 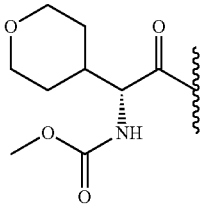 |
| 94 | 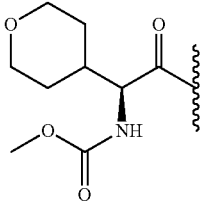 |
| 95 | 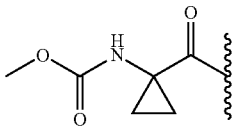 |
| 96 | 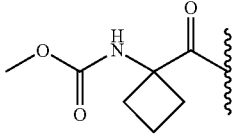 |
| 97 | 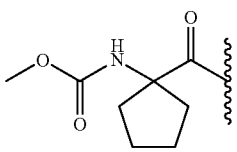 |
| 98 | 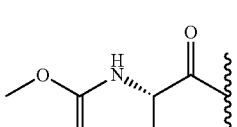 |
| 99 | 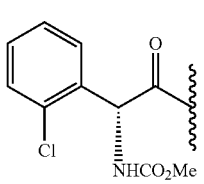 |
| 100 | 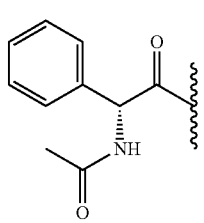 |
| 101 | 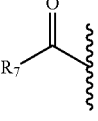 |
| 102 | 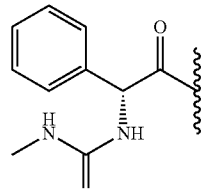 |
| 103 | 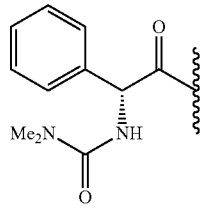 |
| 104 | 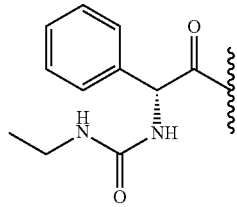 |
| 105 | 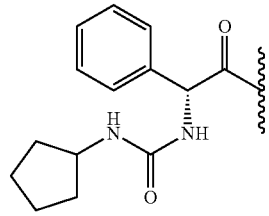 |
| 106 | 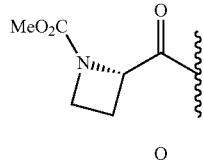 |
| 107 | 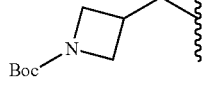 |

TABLE 1-continued
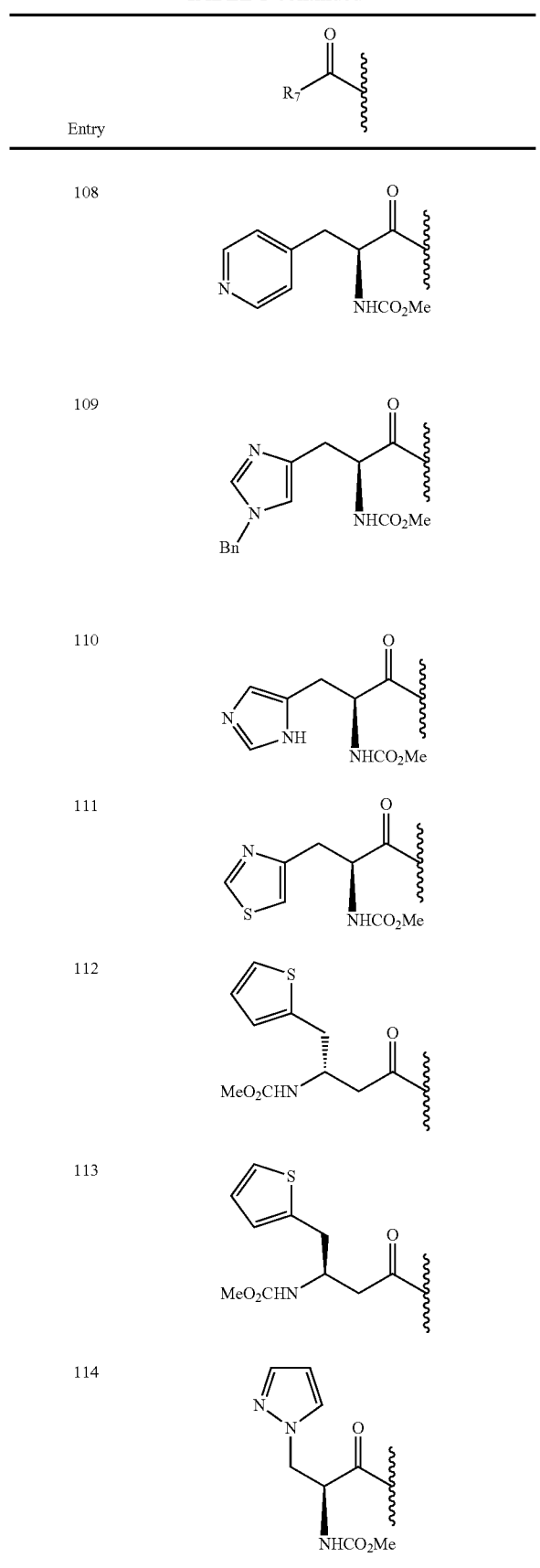
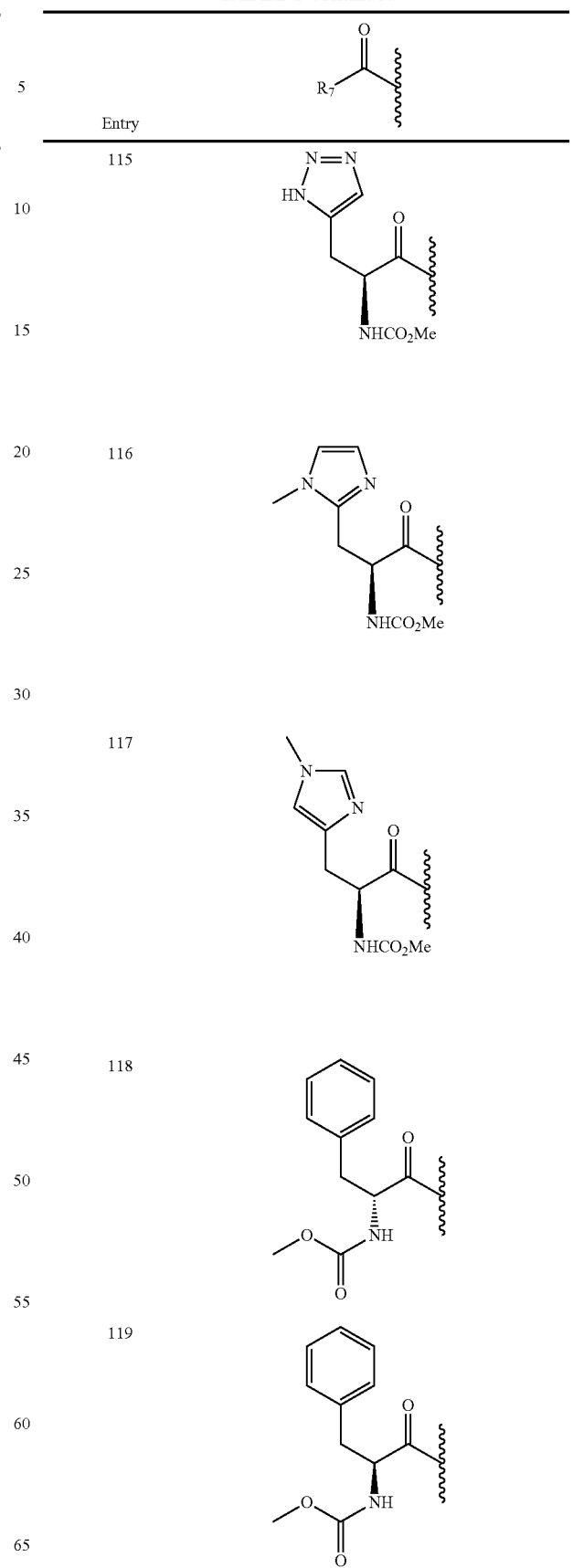

TABLE 1-continued

| Entry | R₇ group |
|---|---|
| 120 | 4-[(HO)(MeO)P(=O)O]-C₆H₄-CH₂-CH(NHCO₂Me)-C(=O)- |
| 121 | (1H-indol-3-yl)-CH₂-CH(NHCO₂Me)-C(=O)- |
| 122 | 4-(OBn)-C₆H₄-CH₂-CH(NHCO₂Me)-C(=O)- |
| 123 | 4-(FmocNH-CH₂)-C₆H₄-CH₂-CH(NHCO₂Me)-C(=O)- |
| 124 | (2-oxo-1,3-oxazolidin-4-yl)-C(=O)- |
| 125 | (2-oxo-1,3-oxazolidin-4-yl)-C(=O)- |
| 126 | (5-methyl-2-oxo-1,3-oxazolidin-4-yl)-C(=O)- |
| 127 | 2-(MeO₂C-NH)-cyclopentyl-C(=O)- |
| 128 | 2-(MeO₂C-NH)-cyclopentyl-C(=O)- |
| 129 | 2-(MeO₂C-NH)-cyclohexyl-C(=O)- |
| 130 | 3-(MeO₂C-NH)-cyclopentyl-C(=O)- |
| 131 | 3-(MeO₂C-NH)-cyclopentyl-C(=O)- |
| 132 | 2-(MeO₂C-NH)-cyclohexyl-C(=O)- |

TABLE 1-continued
| Entry | R₇-C(O)- structure |
|---|---|
| 133 | 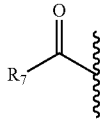 |
| 134 | 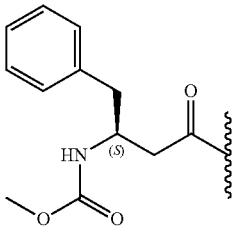 |
| 135 | 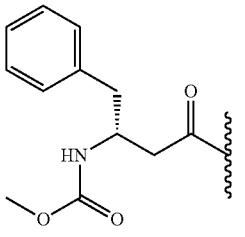 |
| 136 | 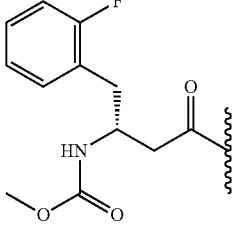 |
| 137 | 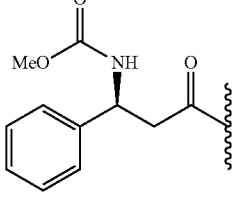 |
| 138 | 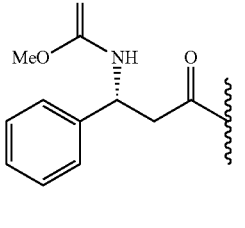 |
| 139 | 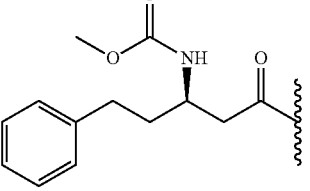 |
| 140 | 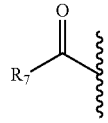 |
| 141 | 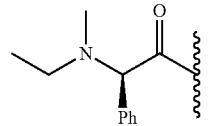 |
| 142 | 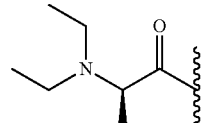 |
| 143 | 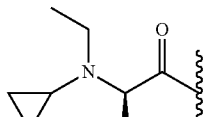 |
| 144 | 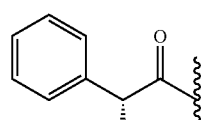 |
| 145 | 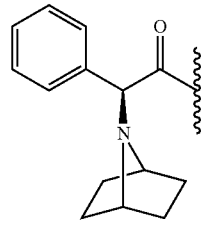 |
| 146 | 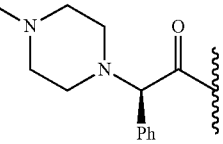 |

TABLE 1-continued

| Entry | R₇ group |
|---|---|
| 147 | (3-fluoropyrrolidin-1-yl), α-Ph |
| 148 | 4-Ph-piperidin-1-yl, α-Ph |
| 149 | 4-hydroxy-4-methyl-piperidin-1-yl, α-Ph |
| 150 | 4-hydroxy-piperidin-1-yl, α-Ph |
| 151 | 2-oxopiperazin-1-yl, α-Ph |
| 152 | morpholin-4-yl, α-Ph |
| 153 | piperidin-1-yl, α-Ph |
| 154 | 4-Cbz-piperazin-1-yl, α-Ph |
| 155 | 2-(trifluoromethyl)phenyl, α-NMe₂ |
| 156 | 3-(trifluoromethyl)phenyl, α-NMe₂ |
| 157 | pyridin-3-yl, α-NMe₂ |
| 158 | pyridin-2-yl, α-NMe₂ |
| 159 | pyridin-4-yl, α-NMe₂ |
| 160 | 3-chlorophenyl, α-NMe₂ |
| 161 | 2-chlorophenyl, α-NMe₂ |
| 162 | 6-chloropyridin-3-yl, α-NMe₂ |
| 163 | 2-fluorophenyl, α-NMe₂, (R) |

TABLE 1-continued
| Entry | |
|---|---|
| 164 | 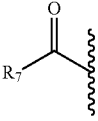 |
| 165 | 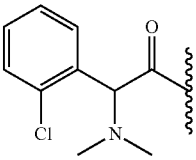 |
| 166 | 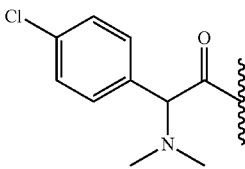 |
| 167 | 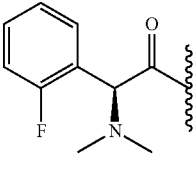 |
| 168 | 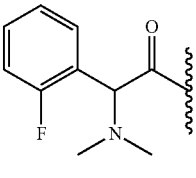 |
| 169 | 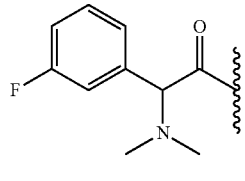 |
| 170 | 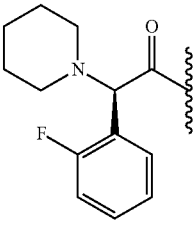 |
| 171 | 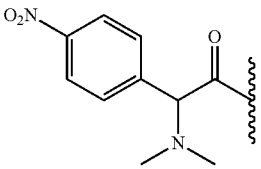 |
| 172 | 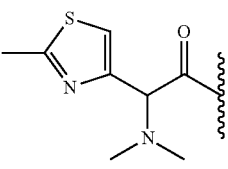 |
| 173 | 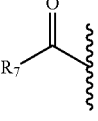 |
| 174 | 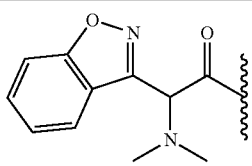 |
| 175 | 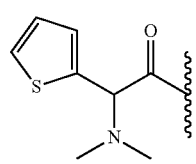 |
| 176 | 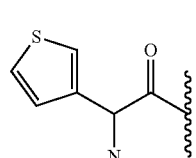 |
| 177 | 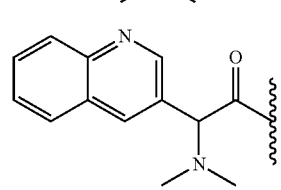 |
| 178 | 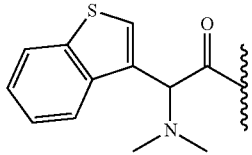 |
| 179 | 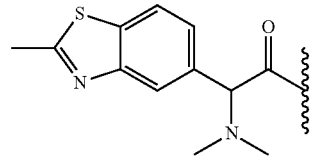 |
| 180 | 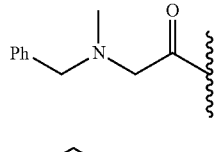 |

TABLE 1-continued
| Entry | R7 group |
|---|---|
| 181 | 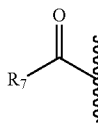 |
| 182 | 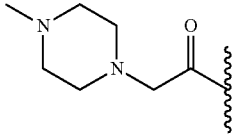 |
| 183 | 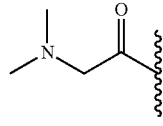 |
| 184 | 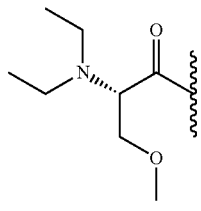 |
| 185 | 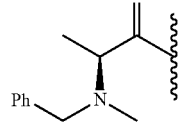 |
| 186 | 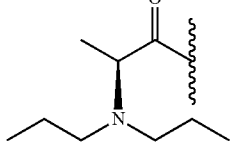 |
| 187 | 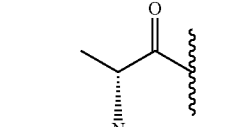 |
| 188 | 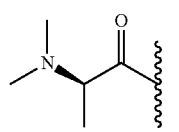 |
| 189 | 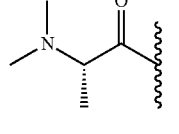 |
TABLE 1-continued
| Entry | R7 group |
|---|---|
| 190 | 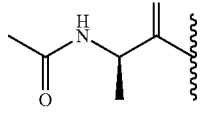 |
| 191 | 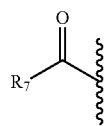 |
| 192 | 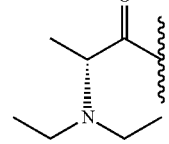 |
| 193 | 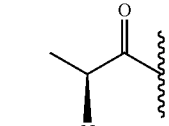 |
| 194 | 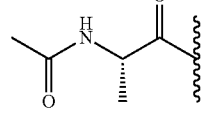 |
| 195 | 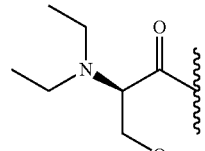 |
| 196 | 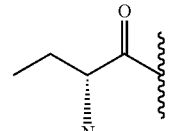 |
| 197 | 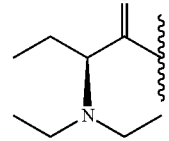 |

TABLE 1-continued
| Entry | |
|---|---|
| 198 | 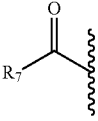 |
| 199 | 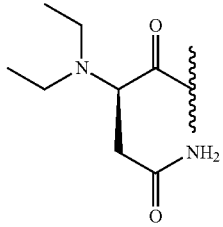 |
| 200 | 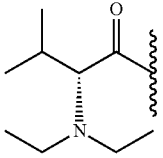 |
| 201 | 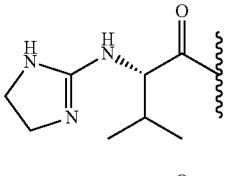 |
| 202 | 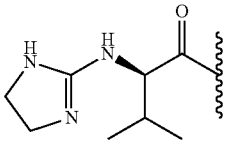 |
| 203 | 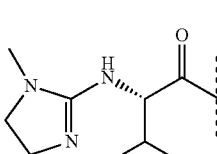 |
| 204 | 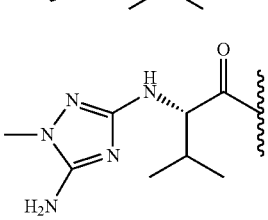 |
| 205 | 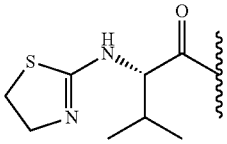 |
| 206 | 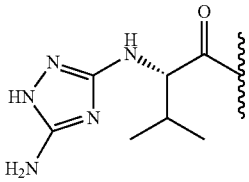 |
| 207 | 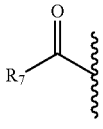 |
| 208 | 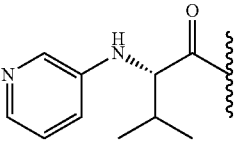 |
| 209 | 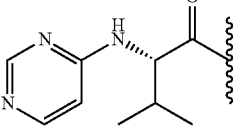 |
| 210 | 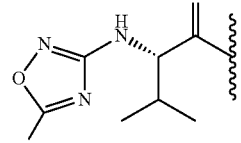 |
| 211 | 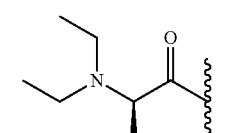 |
| 212 | 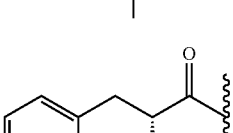 |
| 213 | 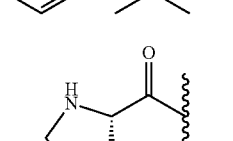 |
| 214 | 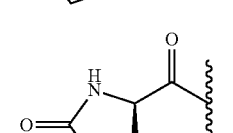 |

TABLE 1-continued

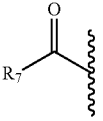

| Entry | |
|---|---|
| 215 | 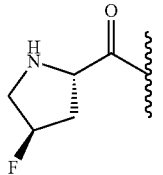 |
| 216 | 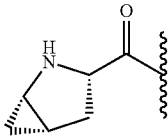 |
| 217 | 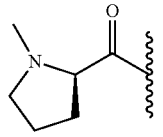 |
| 218 | 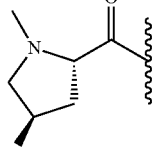 |
| 219 | 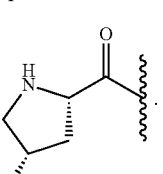 |

A further embodiment of the present invention includes pharmaceutical compositions comprising any single compound delineated herein, or a pharmaceutically acceptable salt, ester, solvate, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, solvate, or prodrug thereof, with a pharmaceutically acceptable carrier or excipient.

Yet a further embodiment of the present invention is a pharmaceutical composition comprising any single compound delineated herein in combination with one or more HCV compounds known in the art, or a pharmaceutically acceptable salt, ester, solvate, or prodrug thereof, with a pharmaceutically acceptable carrier or excipient.

It will be appreciated that reference herein to therapy and/or treatment includes, but is not limited to prevention, retardation, prophylaxis, therapy and cure of the disease. It will further be appreciated that references herein to treatment or prophylaxis of HCV infection includes treatment or prophylaxis of HCV-associated disease such as liver fibrosis, cirrhosis and hepatocellular carcinoma.

It will be further appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

It will be further appreciated that the compounds of the invention, or their pharmaceutically acceptable salts, stereoisomers, tautomers, prodrugs or salt of a prodrug thereof, can be administered as the sole active pharmaceutical agent, or used in combination with one or more agents to treat or prevent hepatitis C infections or the symptoms associated with HCV infection. Other agents to be administered in combination with a compound or combination of compounds of the invention include therapies for disease caused by HCV infection that suppresses HCV viral replication by direct or indirect mechanisms. These include agents such as host immune modulators (for example, interferon-alpha, pegylated interferon-alpha, interferon-beta, interferon-gamma, CpG oligonucleotides and the like), or antiviral compounds that inhibit host cellular functions such as inosine monophosphate dehydrogenase (for example, ribavirin and the like). Also included are cytokines that modulate immune function. Also included are vaccines which comprise HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like. Other agents to be administered in combination with a compound of the present invention include any agent or combination of agents that inhibit the replication of HCV by targeting proteins of the viral genome involved in the viral replication. These agents include but are not limited to other inhibitors of HCV RNA dependent RNA polymerase such as, for example, nucleoside type polymerase inhibitors described in WO01/90121(A2), or U.S. Pat. No. 6,348,587B1 or WO01/60315 or WO01/32153 or non-nucleoside inhibitors such as, for example, benzimidazole polymerase inhibitors described in EP 1 162 196 A1 or WO02/04425.

Accordingly, one aspect of the invention is directed to a method for treating or preventing an infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of the invention, or a pharmaceutically acceptable salt, stereoisomer, tautomer, prodrug, salt of a prodrug, or combination thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

Further aspect of the invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the invention, or a pharmaceutically acceptable salt, stereoisomer, tautomer, prodrug, salt of a prodrug, or combination thereof. Yet another aspect of the invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the invention, or a pharmaceutically acceptable salt, stereoisomer, tautomer, prodrug, salt of a prodrug, or combination thereof. An agent that treats patients for disease caused by hepatitis B (HBV) infection may be for example, but not limited thereto, L-deoxythymidine, adefovir, lamivudine or tenofovir, or any combination thereof. Example of the RNA-containing virus includes, but not limited to, hepatitis C virus (HCV).

Another aspect of the invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the invention, or a pharmaceutically acceptable salt, stereoisomer, tautomer, prodrug, salt of a prodrug, or combination thereof. The agent that treats patients for disease caused by human immunodeficiency virus (HIV) infection may include, but is not limited thereto, ritonavir, lopinavir, indinavir, nelfmavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. Example of the RNA-containing virus includes, but not limited to, hepatitis C virus (HCV). In addition, the present invention provides the use of a compound or a combination of compounds of the invention, or a therapeutically acceptable salt form, stereoisomer, or tautomer, prodrug, salt of a prodrug, or combination thereof, and one or more agents selected from the group consisting of a host immune modulator and a second antiviral agent, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

When used in the above or other treatments, combination of compound or compounds of the invention, together with one or more agents as defined herein above, can be employed in pure form or, where such forms exist, in pharmaceutically acceptable salt form, prodrug, salt of a prodrug, or combination thereof. Alternatively, such combination of therapeutic agents can be administered as a pharmaceutical composition containing a therapeutically effective amount of the compound or combination of compounds of interest, or their pharmaceutically acceptable salt form, prodrugs, or salts of the prodrug, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, further aspect of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt, stereoisomer, or tautomer, prodrug, salt of a prodrug, or combination thereof, one or more agents as defined hereinabove, and a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, [alpha]-, [beta]-, [delta]-, [omega]-, and [tau]-interferons, while examples of class II interferons include, but are not limited to, [gamma]-interferons.

Inhibitors of HCV NS3 protease include agents (compounds or biologicals) that are effective to inhibit the function of HCV NS3 protease in a mammal Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085, WO 2006/007700 and WO 2006/007708 (all by Boehringer Ingelheim), WO 02/060926, WO 03/053349, WO03/099274, WO 03/099316, WO 2004/032827, WO 2004/043339, WO 2004/094452, WO 2005/046712, WO 2005/051410, WO 2005/054430 (all by BMS), WO 2004/072243, WO 2004/093798, WO 2004/113365, WO 2005/010029 (all by Enanta), WO 2005/037214 (Intermune) and WO 2005/051980 (Schering), and the candidates identified as VX-950, ITMN-191 and SCH 503034.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388 and WO 2006/007693 (all by Boehringer Ingelheim), WO 2005/049622 (Japan Tobacco), WO 2005/014543 (Japan Tobacco), WO 2005/012288 (Genelabs), WO 2004/087714 (IRBM), WO 03/101993 (Neogenesis), WO 03/026587 (BMS), WO 03/000254 (Japan Tobacco), and WO 01/47883 (Japan Tobacco), and the clinical candidates XTL-2125, HCV 796, R-1626 and NM 283.

The relevant patent disclosures describing the synthesis of HCV NS5A inhibitors are: US 2009/0202478; US 2009/0202483; WO 2009/020828; WO 2009/020825; WO 2009/102318; WO 2009/102325; WO 2009/102694; WO 2008/144380; WO 2008/021927; WO 2008/021928; WO 2008/021936; WO 2006/1333262; WO 2004/014852; WO 2008/070447; WO 2009/034390; WO 2006/079833; WO 2007/031791; WO 2007/070556; WO 2007/070600; WO 2008/064218; WO 2008/154601; WO 2007/082554; WO 2008/048589, the contents of each of which are expressly incorporated by reference herein.

Inhibitors of another target in the HCV life cycle include agents (compounds or biologicals) that are effective to inhibit the formation and/or replication of HCV other than by inhibiting the function of the HCV NS3 protease. Such agents may interfere with either host or HCV viral mechanisms necessary for the formation and/or replication of HCV Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to an NS5A protein and an NS4B protein.

It can occur that a patient may be co-infected with hepatitis C virus and one or more other viruses, including but not limited to human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

DEFINITIONS

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system including, but not limited to, phenyl, naphthyl, tetrahydronaphthyl, indanyl, idenyl. An aryl group can be a monovalent, bivalent or higher valent radical, as required by the context in which the term is used.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl. A heteroaryl group can be a monovalent, bivalent or higher valent radical, as required by the context in which the term is used.

In accordance with the invention, any of the aryls, substituted aryls, heteroaryls and substituted heteroaryls described herein, can be any aromatic group. Aromatic groups can be substituted or unsubstituted.

The terms "$C_1$-$C_{12}$ alkyl," as used herein, refer to saturated, straight- or branched-chain hydrocarbon radicals containing between one and twelve carbon atoms, which can be optionally inserted one or more hetero atoms such as, but not limited to O, N and S. Examples of $C_1$-$C_{12}$ alkyl radicals include, but are not limited to, ethyl, propyl, isopropyl, n-hexyl, octyl, decyl, dodecyl radicals, —$CH_2OCH_2$—, —$CH_2SCH_2$—, —$CH_2OCH_2CH_2$—, —$CH(CH_3)OCH_2CH_2CH_2CH_2$—.

The term "$C_2$-$C_{12}$ alkenyl," as used herein, refer to straight- or branched-chain hydrocarbon radicals containing from two to twelve carbon atoms having at least one carbon-carbon double bond. One or more hetero atoms such as, but not limited to O, N and S can be optionally inserted between the carbon atoms, provided the hetero atoms are not next to the double bond carbons. Alkenyl groups include, but are not limited to, for example, ethenyl, propenyl, butenyl, 1-methyl-2-buten-1-yl, heptenyl, octenyl, —$CH(CH_3)OCH_2C=CH_2$, and the like.

The term "$C_3$-$C_{12}$-cycloalkyl," as used herein, refers to a monocyclic or polycyclic saturated carbocyclic ring compound. Examples of $C_3$-$C_{12}$-cycloalkyl include, but not limited to, cyclopropyl, cyclobutyl, cyclopentyl, cyclohexyl, cycloheptyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The term "$C_3$-$C_{12}$-cycloalkylene," as used herein, refers to a monocyclic or polycyclic saturated carbocyclic ring compound. Examples of $C_3$-$C_{12}$-cycloalkyl include, but not limited to, cyclopropylene, cyclobutylene, cyclopentylene, cyclohexylene, cycloheptylene and cyclooctylene, bicyclo[2.2.1]heptylene, and bicyclo[2.2.2]octylene.

The term "$C_3$-$C_{12}$ cycloalkenyl" as used herein, refers to monocyclic or polycyclic carbocyclic ring compound having at least one carbon-carbon double bond. Examples of $C_3$-$C_{12}$ cycloalkenyl include, but not limited to, cyclopropenyl, cyclobutenyl, cyclopentenyl, cyclohexenyl, cycloheptenyl, cyclooctenyl, and the like. The term "$C_3$-$C_{12}$ cycloalkenylene" as used herein, refers to monocyclic or polycyclic carbocyclic ring compound having at least one carbon-carbon double bond. Examples of $C_3$-$C_{12}$ cycloalkenylene include, but not limited to, cyclopropenylene, cyclobutenylene, cyclopentenylene, cyclohexenylene, cycloheptenylene, cyclooctenylene, and the like.

It is understood that any alkyl, alkenyl, alkynyl and cycloalkyl moiety described herein can also be an aliphatic group, an alicyclic group or a heterocyclic group. An "aliphatic" group is a non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocyclic groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The term "substituted" refers to substitution by independent replacement of one, two, or three or more of the hydrogen atoms thereon with substituents including, but not limited to, —F, —Cl, —Br, —I, —OH, protected hydroxy, —NO$_2$, —CN, —N$_3$, —NH$_2$, protected amino, oxo, thioxo, —NH—C$_1$-C$_{12}$-alkyl, —NH—C$_2$-C$_8$-alkenyl, —NH—C$_2$-C$_8$-alkynyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_8$-alkenyl, —O—C$_2$-C$_8$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_8$-alkenyl, —C(O)—C$_2$-C$_8$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_8$-alkenyl, —CONH—C$_2$-C$_8$-alkynyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_8$-alkenyl, —C(O)—C$_2$-C$_8$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_8$-alkenyl, —OCONH—C$_2$-C$_8$-alkynyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_8$-alkenyl, —NHC(O)—C$_2$-C$_8$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_8$-alkenyl, —NHCO$_2$—C$_2$-C$_8$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_8$-alkenyl, —NHC(O)NH—C$_2$-C$_8$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_8$-alkenyl, —NHC(S)NH—C$_2$-C$_8$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_8$-alkenyl, —NHC(NH)NH—C$_2$-C$_8$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_8$-alkenyl, —NHC(NH)—C$_2$-C$_8$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_8$-alkenyl, —S(O)—C$_2$-C$_8$-alkynyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_8$-alkenyl, —SO$_2$NH—C$_2$-C$_8$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "halogen," as used herein, refers to an atom selected from fluorine, chlorine, bromine and iodine.

The term "hydroxy activating group", as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations, 2$^{nd}$ Ed.* Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)— or (S)—, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The present invention also relates to solvates of the compounds of Formula (I), for example hydrates.

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the Formula described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the invention described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), cytokine agonists, cytokine antagonists, lung surfactants and/or antimicrobial and anti-viral agents (eg ribavirin and amantidine). The compositions according to the invention may also be used in combination with gene replacement therapy.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are:

Ac for acetyl;
$Boc_2O$ for di-tert-butyl-dicarbonate;
Boc for t-butoxycarbonyl;
Bz for benzoyl;
Bn for benzyl;
BocNHOH for tert-butyl N-hydroxycarbamate;
t-BuOK for potassium tert-butoxide;
BOP for (benzotriazol-1-yloxy)tris(dimethylamino)phosphonium;
Hexafluorophosphate;
Brine for sodium chloride solution in water;
Cbz for benzyloxycarbonyl;
CDI for carbonyldiimidazole;
$CH_2Cl_2$ for dichloromethane;
$CH_3$ for methyl;
$CH_3CN$ for acetonitrile;
$Cs_2CO_3$ for cesium carbonate;
dba for dibenzylidene acetone;
dppb for diphenylphosphino butane;
dppe for diphenylphosphino ethane;
DBU for 1,8-diazabicyclo[5.4.0]undec-7-ene;
DCC for N,N'-dicyclohexylcarbodiimide;
DEAD for diethylazodicarboxylate;
DIAD for diisopropyl azodicarboxylate;
DIPEA or $(i-Pr)_2EtN$ for N,N,-diisopropylethyl amine;
Dess-Martin periodinane for 1,1,1-tris(acetyloxy)-1,1-dihydro-1,2-benziodoxol-3-(1H)-one;
DMAP for 4-dimethylaminopyridine;
DME for 1,2-dimethoxyethane;
DMF for N,N-dimethylformamide;
DMSO for dimethyl sulfoxide;
DPPA for diphenylphosphoryl azide;
EDC for N-(3-dimethylaminopropyl)-N'-ethylcarbodiimide;
EDC HCl for N-(3-dimethylaminopropyl)-N'-ethylcarbodiimide hydrochloride;
EtOAc for ethyl acetate;
EtOH for ethanol;
$Et_2O$ for diethyl ether;
HATU for O-(7-azabenzotriazol-1-yl)-N,N,N',N',-tetramethyluronium;
Hexafluorophosphate;
HCl for hydrogen chloride;
HOBT for 1-hydroxybenzotriazole;
$K_2CO_3$ for potassium carbonate;
MeOH for methanol;
Ms for mesyl or $-SO_2-CH_3$;
$Ms_2O$ for methanesulfonic anhydride or mesyl-anhydride;
$NaHCO_3$ for sodium bicarbonate or sodium hydrogen carbonate;
$Na_2CO_3$ sodium carbonate;
NaOH for sodium hydroxide;
$Na_2SO_4$ for sodium sulfate;
$NaHSO_3$ for sodium bisulfite or sodium hydrogen sulfite;
$Na_2S_2O_3$ for sodium thiosulfate;
$NH_2NH_2$ for hydrazine;
$NH_4HCO_3$ for ammonium bicarbonate;
$NH_4Cl$ for ammonium chloride;
NMMO for N-methylmorpholine N-oxide;
$NaIO_4$ for sodium periodate;
OH for hydroxy;
$OsO_4$ for osmium tetroxide;
TEA or $Et_3N$ for triethylamine;
TFA for trifluoroacetic acid;
THF for tetrahydrofuran;
TPP or $PPh_3$ for triphenylphosphine;
Ts for tosyl or $-SO_2-C_6H_4CH_3$;
$Ts_2O$ for tolylsulfonic anhydride or tosyl-anhydride;
TsOH for p-tolylsulfonic acid;
Pd for palladium;
Ph for phenyl;
$Pd_2(dba)_3$ for tris(dibenzylideneacetone)dipalladium(0);
$Pd(PPh_3)_4$ for tetrakis(triphenylphosphine)palladium(0);
TBS for tert-butyl dimethylsilyl;
TMS for trimethylsilyl; or
TMSCl for trimethylsilyl chloride.

Synthetic Methods

The compounds and processes of the present invention will be better understood in connection with the following synthetic schemes that illustrate the methods by which the compounds of the invention may be prepared.

As shown in Scheme 1, an intermediate of formula (1-5) may be prepared from 3-amino-thiophene-2-carboxylic acid methyl ester (1-1). The compound of formula (1-2) may be prepared by reductive amination. The reducing agents include, but not limited to, BH3, $NaBH_3CN$, $Et_3SiH$, $PhSiH_3$ and $PhMe_2SiH$. The acids includes, not limited to, HOAc, HCl, and $Bu_2SnCl_2$. The prefer condition is $PhSiH_3$ and $Bu_2SnCl_2$. Acylation of the compound of formula (1-2) can be accomplished under standard acylation conditions to give the compound of formula (1-3) where $R_8$ is as previously defined. One condition is to react with correspondent carboxylic acid. The coupling regent can be selected from, but not limited to, DCC, EDC, di-isopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, $CH_2Cl_2$, DMF or THF. The reaction temperature can vary from 0° C. to about 50° C. Another condition is to react with acid chloride in the presence of suitable bases such as, but not limited to, triethylamine, diisopropylethylamine, DBU, N-methylmorpholine and DMAP. Alternatively, the compound of (1-2) may be reacted with an isocyanate or carbamoyl chloride to give the compound of formula (1-3) where $R_8$ is an amine. The compound of formula (1-4) may be prepared by thiophene halogenation of compound of formula (1-3). The detailed discussion of halogenation is described by R. C. Larlock in *Comprehensive Organic Transformation*. The preferred halide is bromide or iodide. The compound of formula (1-5) can be prepared by reacting the compound of formula (1-4) with an aryl boronic acid or an aryl boronic ester under the Suzuki conditions which are known to those skilled in the art (see reviews: A. Suzuki, *Pure Applied Chem.* 1991, 63, 419; A. Suzuki, *Handbook of Organopalladium Chemistry for Organic Synthesis* 2002, 1, 249; A. Anastasi.

Scheme 1

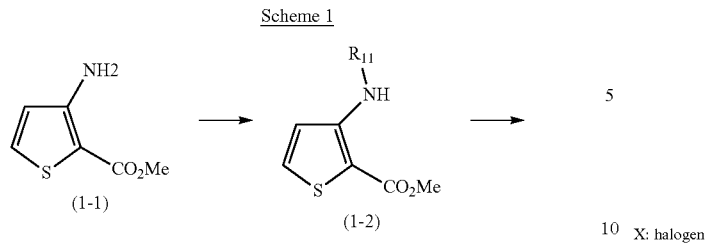

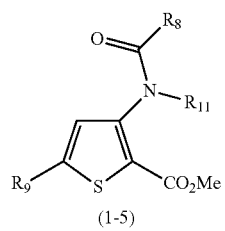

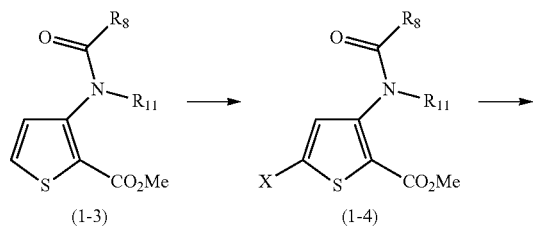

X: halogen

The preparation of another key intermediate is depicted in scheme 2. Aryl boronic ester of formula (2-1) is coupled with the aryl bromide of formula (2-2) using standard Suzuki coupling conditions described in *Angew. Chem. Int. Ed. Engl.* 2001, 40, 4544. It should be noted that other boronic esters or boronic acid analogs of the compound of formula (2-2) may be used instead of the pinacol boronic ester. A, B, $R_3$, $R_4$, $R_5$, $R_6$ are as previously defined. $R_{p1}$ and $R_{p2}$ are amino protecting groups such as, but not limited to, Boc and Cbz.

Scheme 2

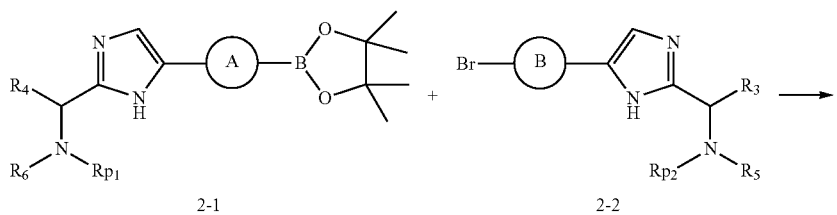

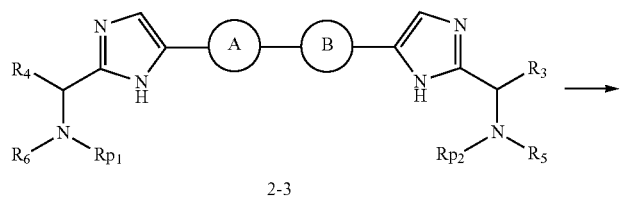

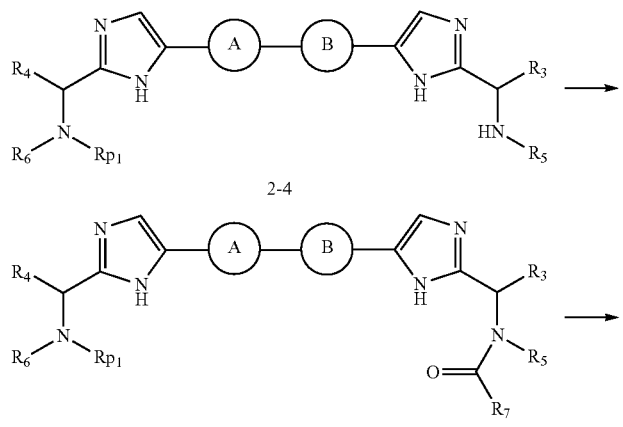

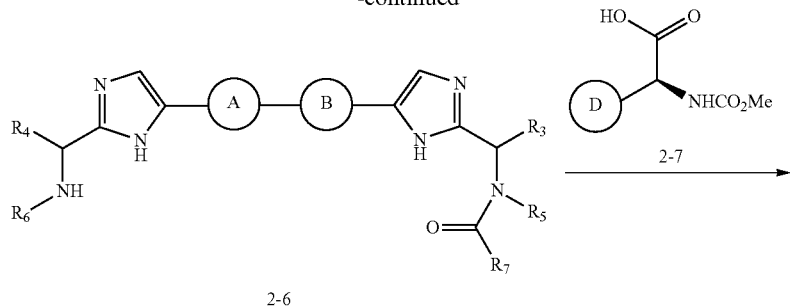

2-6

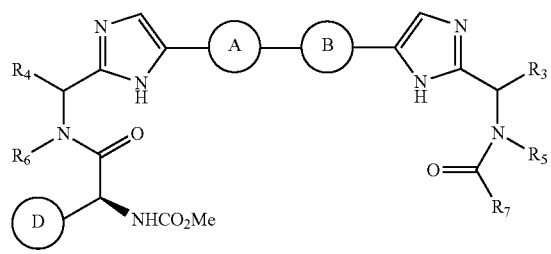

2-8

Compound of formula (2-3) is converted to the compound of formula (2-4) by selective deprotection of $R_{p2}$. The selective deprotection is only achieved when $R_{p1}$ and $R_{p2}$ are different such as $R_{p1}$ is Boc and $R_{p2}$ is Cbz. When $P_{p2}$ is Cbz, catalytic hydrogenation deprotection condition can be used. A more through discussion of the procedures, reagents and conditions for removing protecting groups is described in literature, for example, by T. W. Greene and P. G. M. Wuts in "*Protective Groups in Organic Synthesis*" $3^{rd}$ ed., John Wiley & Son, Inc., 1999. Acylation of the compound of formula (2-4) can be accomplished under standard acylation condition to give the compound of formula (2-5) where $R_7$ is as previously defined. The coupling regent can be selected from, but not limited to DCC, EDC, di-isopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, $CH_2Cl_2$, DMF and THF. The reaction temperature can vary from 0° C. to about 50° C. Alternatively, the compound of (2-4) may be reacted with an isocyanate or carbamoyl chloride to give the compound of formula (2-5) where $R_7$ is an amine. The compound of formula (2-5) is converted to the compound of formula (2-6) by deprotection of $R_{p1}$. When $R_{p1}$ is Boc, acidic deprotection can be used. A more through discussion of the procedures, reagents and conditions for removing protecting groups is described in literature, for example, by T. W. Greene and P. G. M. Wuts in "*Protective Groups in Organic Synthesis*" $3^{rd}$ ed., John Wiley & Son, Inc., 1999. Further coupling of the compound of formula (2-6) with the compound of formula (2-7) affords the key intermediate of the compound of formula (2-8). The coupling regent can be selected from, but not limited to DCC, EDC, di-isopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, $CH_2Cl_2$, DMF and THF. The reaction temperature can vary from 0° C. to about 50° C.

The preparation of compound of formula (2-1) and compound of formula (2-2) is illustrated in scheme 3. The compound of formula (2-1) may be derived from bromoketone compound of formula (3-2), which can be prepared from the corresponding ketone compound of formula (3-1) in the presence of a bromination reagent such as NBS, bromine, or the like, optionally in the presence of an acid and/or with heating. Then the bromoketone compound of formula (3-2) may be either converted to the corresponding amine, compound of formula (3-3), or coupled with protected amino acid, the compound of formula (3-4) in the presence of a base such as $Et_3N$ or DIPEA to afford keto-ester, compound of formula (3-5). Similarly, amine compound of formula (3-3) may be converted to the corresponding keto-amide compound of formula (3-6) via condensation with appropriate amino acid under standard amide formation conditions. Both compound of formula (3-5) and compound of formula (3-6) may be transformed to aryl bromide, the compound of formula (3-7) via heating with $NH_4OAc$ under thermal or microwave conditions. The key intermediate, compound of formula (2-1) can be prepared by reacting with diboron reagent (3-9) under the Suzuki conditions which are known to those skilled in the art (see reviews: A. Suzuki, *Pure Applied Chem.* 1991, 63, 419; A. Suzuki, *Handbook of Organopalladium Chemistry for Organic Synthesis* 2002, 1, 249; A. Anastasia, et al, *Handbook of Organopalladium Chemistry for Organic Synthesis* 2002, 1, 311; 1). Another key intermediate the compound of formula (2-2) may be prepared from the compound of formula (3-8) in the same fashion as the preparation of the compound of formula (3-7).

Scheme 3

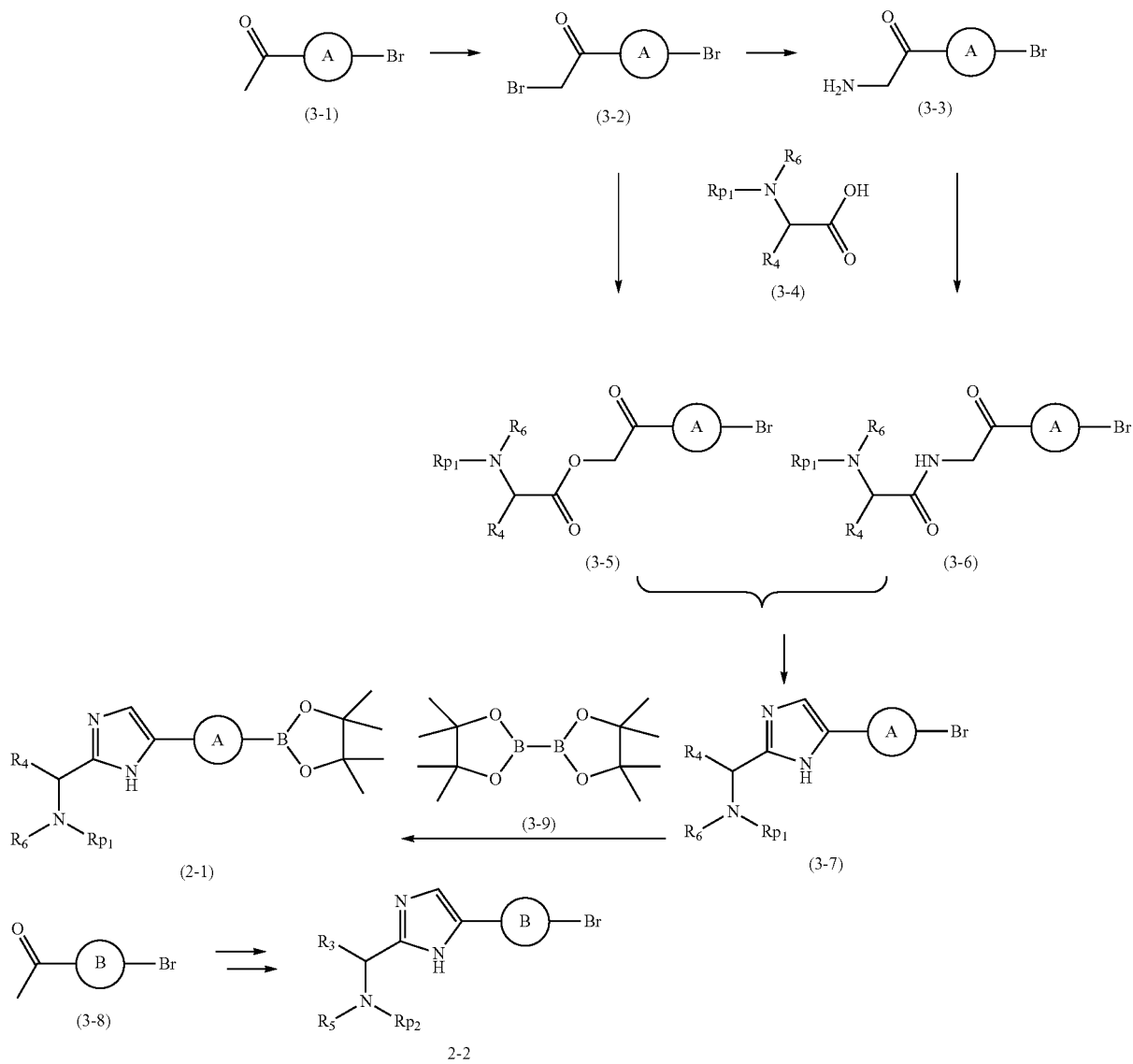

The novel hybrid compounds of the present invention may be prepared by linking the intermediates the compound of formula (1-5) with the compound of formula (2-8). The linker can be, but is not limited to, amine, ether, thioether, carbamate, urea.

An example of the linking strategies that may be used to prepare the compounds of the present invention is shown in Scheme 4.

Scheme 4

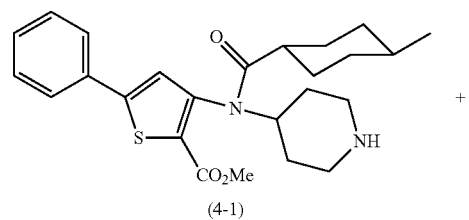

(4-1)

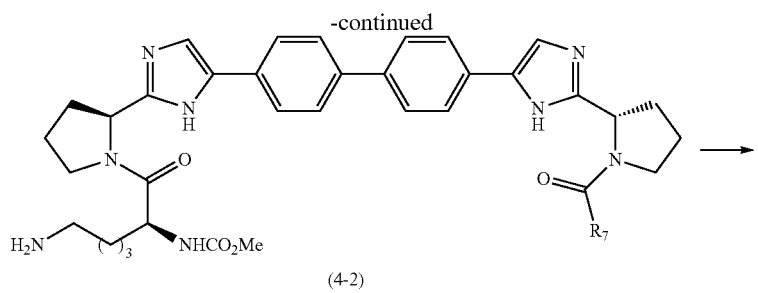
(4-2)
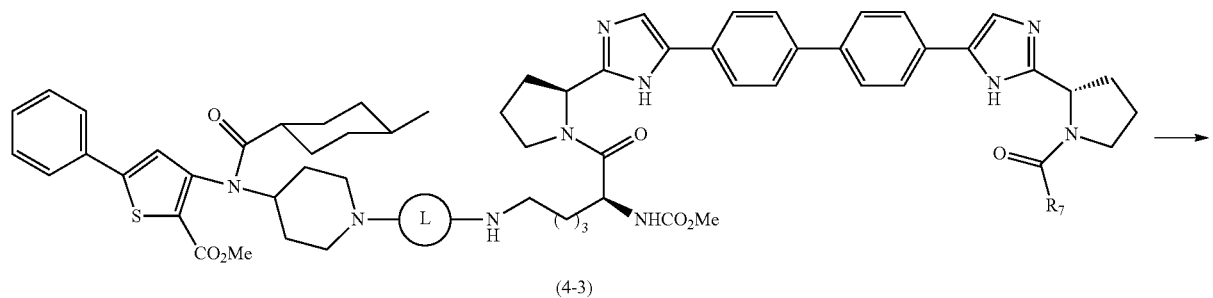
(4-3)
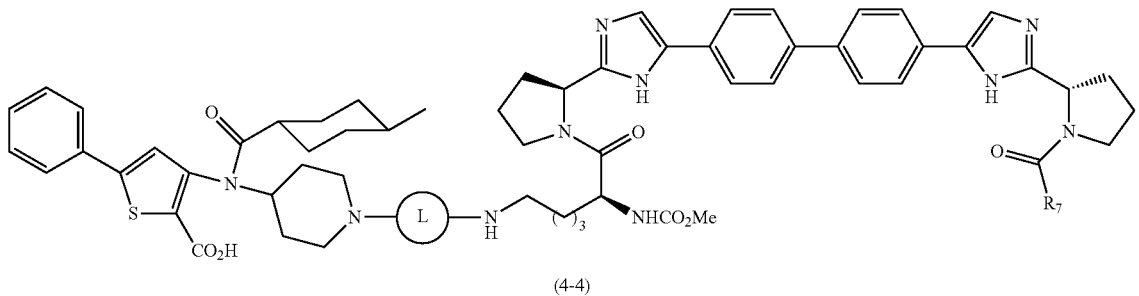
(4-4)
An example of preparation of the key intermediate, compound of formula (4-2) is illustrated in scheme 5.
Scheme 5
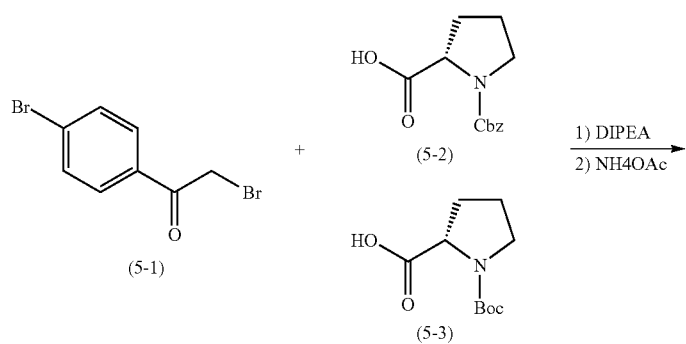

-continued
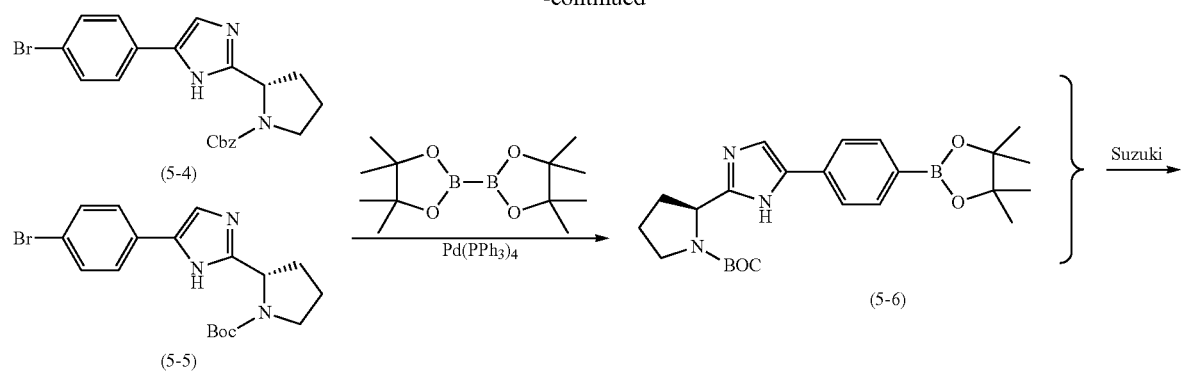
(5-4)
(5-5)
(5-6)
Suzuki
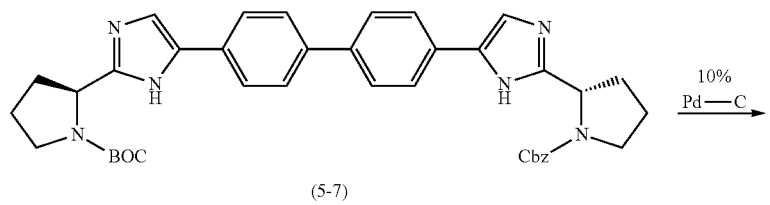
(5-7)
10% Pd—C
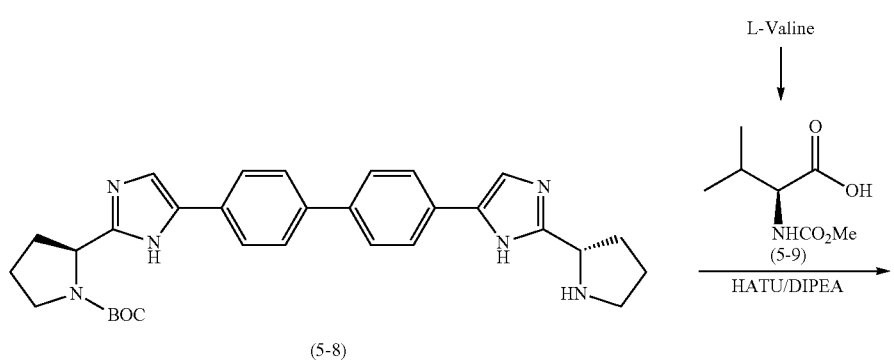
(5-8)
L-Valine
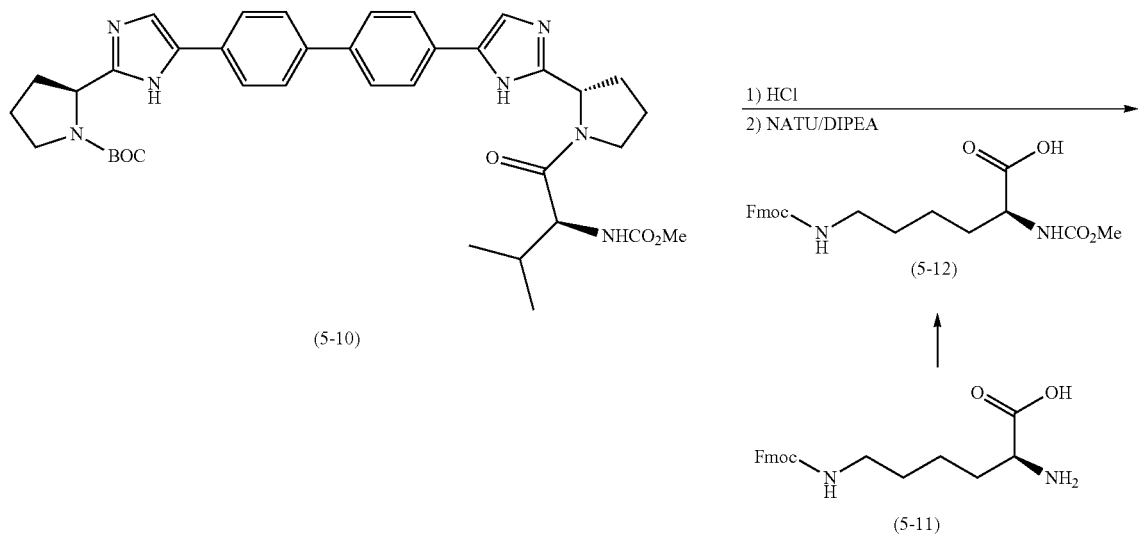
(5-9)
HATU/DIPEA
(5-10)
1) HCl
2) NATU/DIPEA
(5-12)
(5-11)

-continued

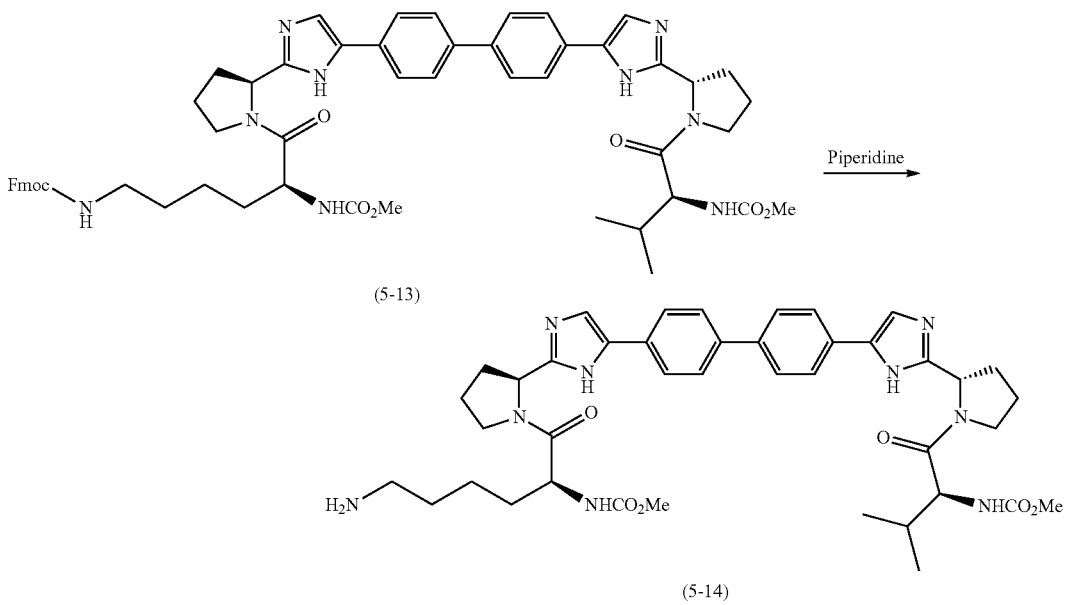

Example 1

Compound of formula (4-4): where L is —(CO)—, and R₇ is

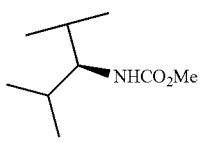

Step 1a: benzyl 4-(2-(methoxycarbonyl)-5-phenylthiophen-3-ylamino)piperidine-1-carboxylate

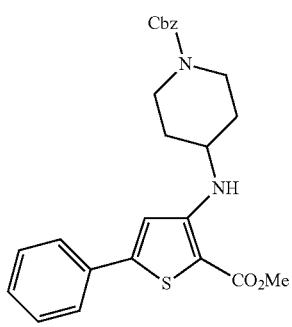

To a solution of 3-amino-5-phenyl-thiophene-2-carboxylic acid methyl ester (2.33 g, 10 mmol) in THF (2.0 mL) was added benzyl 4-oxopiperidine-1-carboxylate (2.33 g, 10 mmol), dibutyltin chloride (302 mg, 1.0 mmol) and phenylsilane (1.36 ml, 11 mmol) at room temperature. The reaction mixture was stirred for two days at room temperature and quenched with saturated NaHCO3 aqueous solution. The mixture was extracted with ethyl acetate and washed with brine. Dried and concentrated, the crude was purified on silica gel column to give the title compound (4.23 g, 94%).

MS: (ESI) m/z (M+H) 452.16

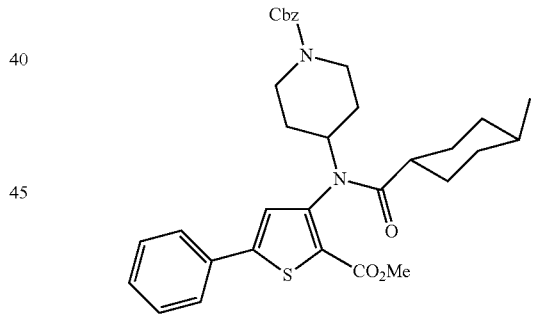

Step 1b: benzyl 4-((1r,4r)-N-(2-(methoxycarbonyl)-5-phenylthiophen-3-yl)-4-methylcyclohexanecarboxamido)piperidine-1-carboxylate To a solution of benzyl 4-(2-(methoxycarbonyl)-5-phenylthiophen-3-ylamino)piperidine-1-carboxylate (540 mg, 1.12 mmol) in DCE (4.0 mL) was added trans-4-methylcyclohexylchloride (360 mg, 2.24 mmol), and sym-collidine (0.59 mL, 4.48 mmol) at room temperature. The reaction mixture was heated for 16 h at 90° C. and quenched with saturated NaHCO₃ aqueous solution. The mixture was extracted with ethyl acetate and washed with brine. Dried and concentrated, the crude was purified on silica gel column to give the title compound (520 mg, 80%).

MS: (ESI) m/z (M+H) 575.28

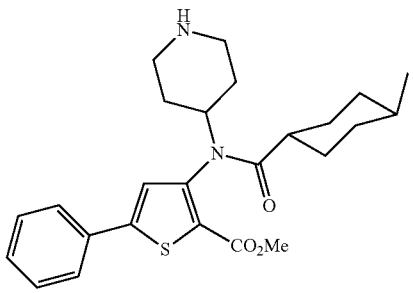

Step 1c: methyl 3-((1r,4r)-4-methyl-N-(piperidin-4-yl)cyclohexanecarboxamido)-5-phenylthiophene-2-carboxylate To a solution of benzyl 4-((1r,4r)-N-(2-(methoxycarbonyl)-5-phenylthiophen-3-yl)-4-methylcyclohexanecarboxamido)piperidine-1-carboxylate (357 mg, 0.62 mmol) in 6:1 EtOAC/MeOH (5.0 ml) was added 10% palladium on charcoal (80 mg) at room temperature. The reaction mixture was placed under H$_2$ atmosphere (25-35 psi) for 3 days, then filter through celite and evaporated to dryness. The crude was purified on silica gel column to give the title compound (136 mg, 50%).

MS: (ESI) m/z (M+H) 441.23

Step 1d: Compound of Formula (5-9)

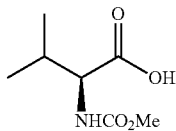

To a mixture of L-Valine (3.9 g, 33.29 mmol) in 1M-NaOH (33 mL, 33 mmol) was added Na$_2$CO$_3$ (1.83 g, 17.2 mmol) and cooled to 0° C. Methyl chloroformate (2.8 mL, 36.1 mmol) was slowly added to the reaction mixture at 0° C. for 10 min. and allowed to warm to room temperature and stirred for 3 hours. The reaction mixture was washed with diethyl ether (3×10 mL). The aqueous layer was cooled to 0° C. and acidified with concentrated HCl to pH (~2) and extracted with methylene chloride (3×30 mL). The combined organic layer was washed with brine, dried over Na$_2$SO$_4$, filtered, evaporated and dried on vacuum pump to give the title compound (5.3 g) as a white power.

Step 1e: Compound of Formula (5-12)

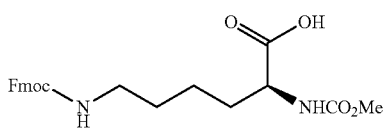

To a mixture of (5-11) (1.011 g, 2.15 mmol) in anhydrous methylene chloride (7 mL) was added HCl (14 mL, 4M in 1,4-dioxane) was dropwise added at room temperature and stirred for 1.5 hours. It was evaporated off and dried on vacuum pump to give HCl salt as a white solid. To a mixture of HCl salt in methylene chloride (27 mL) was added diisopropylethylamine (1.13 mL, 6.47 mmol) and methyl chloroformate (0.17 mL, 2.27 mmol) successively at 0° C. and stirred at room temperature for 1.5 hours. The reaction mixture was diluted with methylene chloride (70 mL), washed with 1 M-HCl, H$_2$O and brine. The organic layer was dried over Na$_2$SO$_4$, filtered and evaporated to dryness. The residue was purified by SiO$_2$ column chromatography using 0-15% methanol in methylene chloride to give the title compound (0.6 g) as a white solid.

MS: (ESI) m/z (M+H) 427.30

Step 1f: Compound of Formula (5-4)

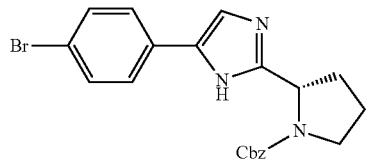

To a mixture of 1,4-dibromoacetophenone (5-1) (7.0 g, 25.19 mmol) and Cbz-L-proline (5-2) (6.59 g, 26.45 mmol) in acetonitrile (65 mL) was added diisopropylethylamine (5.27 mL, 30.23 mmol) and stirred at room temperature for 1.5 hours. The reaction was evaporated off, diluted with ethylacetate (100 mL), washed with aqueous saturated NaHCO$_3$ solution and brine. The organic layer was dried over Na$_2$SO$_4$, filtered and evaporated to give a brownish solid (~12 g), which was used directly for the next reaction without further purification. A mixture of previously obtained brownish solid (~12 g) and ammonium acetate (19.42 g, 252 mmol) in toluene (74 mL) was heated at 100° C. for 16.5 hours. After cooling to room temperature, the reaction mixture was treated with saturated aqueous NaHCO$_3$ solution (pH ~9), extracted with ethyl acetate (3×50 mL). The combined organic layer was washed with H$_2$O and brine, dried over Na$_2$SO$_4$, filtered and evaporated to dryness. The residue was purified by SiO$_2$ column chromatography using 0-60% ethyl acetate in hexanes to give the title compound (5-4) (9.7 g) as a pale brownish form.

MS: (ESI) m/z (M+H) 426.23, 428.23

Step 1g: Compound of Formula (5-5)

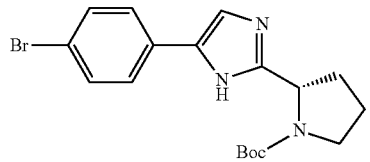

The compound of formula (5-5) may be prepared in the same fashion as the preparation of the compound of formula (5-4).

Step 1h: Compound of Formula (5-6)

A mixture of the compound of formula (5-5) (5.0 g, 12.74 mmol), bis-(pinacolato)diboron (3.59 g, 14.01 mmol) and potassium acetate (1.88 g, 19.1 mmol) in 1,4-dioxane (42 mL) was degassed. Pd(PPh₃)₄ (735 mg, 0.64 mmol) was added to the reaction and degassed again. The reaction mixture was heated at 80° C. for 14.5 hours. It was diluted with ethyl acetate (200 mL) and washed with saturated aqueous NaHCO₃ solution. The aqueous layer was extracted with ethyl acetate (2×100 mL). The combined organic layer was washed with H₂O and brine, dried over Na₂SO₄, filtered and evaporated to dryness. The residue was purified by SiO₂ column chromatography using 0-60% ethyl acetate in hexanes to give the title compound (5-6) (4.184 g) as a pale yellow solid.

MS: (ESI) m/z (M+H) 440.30

Step 1i: Compound of Formula (5-7)

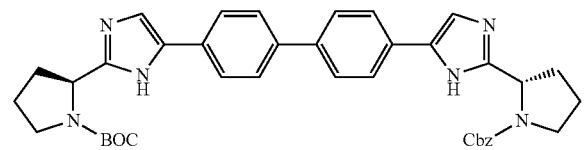

A mixture of boronic ester, the compound of formula (5-6) (1 g, 2.28 mmol), arylbromide, the compound of formula (5-5) (1.02 g, 2.39 mmol) and NaHCO₃ (630 mg, 7.51 mmol) in DME-H₂O (3:1, 24 mL) was degassed and Pd(PPh₃)₄ (138 mg, 0.12 mmol) was added to the reaction and degassed again. The reaction mixture was heated at 80° C. for 14 hours. It was filtered through a fritted funnel and evaporated off. The residue was diluted with methylene chloride and H₂O. The aqueous layer was extracted with methylene chloride. The combined organic layer was washed with H₂O and brine, dried over Na₂SO₄, filtered and evaporated to dryness. The residue was purified by SiO₂ column chromatography using 30-100% ethyl acetate containing 1% triethylamine in hexanes to give the title compound (5-7) (0.662 g) as a pale yellow solid.

MS: (ESI) m/z (M+H) 659.29

Step 1j: Compound of Formula (5-8)

A mixture of the compound of formula (5-7) (1.78 g, 2.7 mmol), 10% Pd—C (371 mg), K₂CO₃ (336 mg) and H₂O (6 drops) in EtOH (50 mL) was vigorously stirred under H2 atmosphere (using balloon) for 6 hours. Then, 10% Pd—C (120 mg) and K₂CO₃ (120 mg) were additionally added to the reaction and vigorously stirred for 2 hours. It was filtered through a pad of celite and evaporated to dryness. The residue was purified by SiO₂ column chromatography using 0-25% methanol in methylene chloride to give the title compound the compound of formula (5-8) (1.204 g) as a pale yellow solid.

MS: (ESI) m/z (M+H) 525.29

Step 1k: Compound of Formula (5-10)

To a mixture of the compound of formula (5-8) (1.2 g, 2.28 mmol), the compound of formula (5-9) (440 mg, 2.51 mmol) and diisopropylethylamine (1.2 mL, 6.84 mmol) in anhydrous methylene chloride (23 mL) was portionwise added HATU (955 mg, 2.51 mmol) at room temperature and stirred for 1.5 hours. The reaction mixture was diluted with methylene chloride (30 mL), washed with saturated aqueous NaHCO₃ Solution, H₂O and brine, dried over Na₂SO₄, filtered and evaporated to dryness. The residue was dissolved in methanol 15 mL), treated with K₂CO₃ (315 mg) and stirred for 1 hour. The reaction was filtered through a fritted funnel and evaporated to dryness. The residue was purified by SiO₂ column chromatography using 0-4% methanol in methylene chloride to give the title compound (5-10) (1.366 g) as a pale yellow foam.

MS: (ESI) m/z (M+H) 682.56

Step 1l: Compound of Formula (5-13)

To a mixture of the compound of formula (5-10) (300 mg, 0.44 mmol) in anhydrous methylene chloride (1 mL) was added HCl (4 mL, 4M in 1,4-dioxane) and stirred for 1.5 hour. The reaction was evaporated off and dried on vacuum pump to give a HCl salt. To a mixture of HCl salt previously obtained and the compound of formula (8-12) (216 mg, 0.51 mmol) in methylene chloride (8 mL) was added diisopropylethylamine (0.54 mL, 3.08 mmol) at 0° C. followed by addition of HATU (192 mg, 0.51 mmol) and stirred for at room temperature for 2 hours. The reaction mixture was diluted with methylene chloride (10 mL), washed with saturated aqueous NaHCO$_3$ solution, H$_2$O and brine, dried over Na$_2$SO$_4$, filtered and evaporated to dryness. The residue was dissolved in methanol (10 mL), treated with K$_2$CO$_3$ (12 mg) and stirred for 30 min. The reaction was filtered through a fritted funnel and evaporated to dryness. The residue was purified by SiO$_2$ column chromatography using 0-4% methanol in methylene chloride to give the title compound (5-13) (401 mg) as a pale yellow foam.

MS: (ESI) m/z (M+H) 990.52

Step 1m: Compound of Formula (5-14)

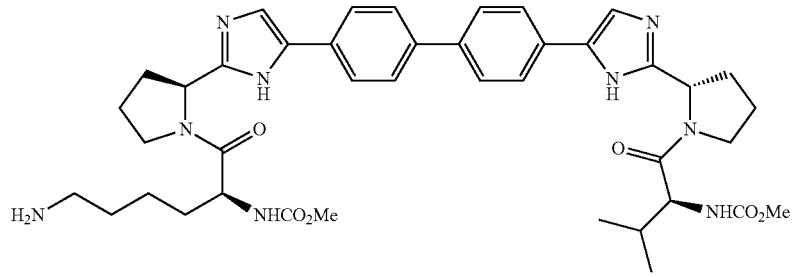

To a mixture of the compound of formula (5-13) (200 mg, 0.2 mmol) in anhydrous THF (2 mL) was added piperidine (0.2 mL, 2 mmol) at room temperature and stirred for 2.5 hours. The reaction mixture was evaporated, dissolved in methylene chloride (1 mL) and toluene (2 mL), evaporated to dryness. The residue was purified by SiO$_2$ column chromatography using 0-20% methanol (2N—NH$_3$) in methylene chloride to give the title compound (5-14) (145 mg) as a pale yellow foam.

MS: (ESI) m/z (M+H) 768.81

Step 1n: Compound of Formula (4-3): where L is —(CO)—, and R$_7$ is

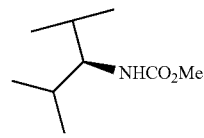

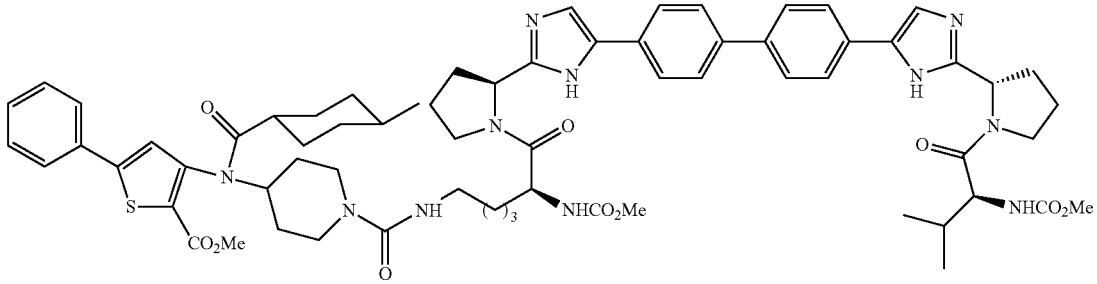

A mixture of methyl 3-((1r,4r)-4-methyl-N-(piperidin-4-yl)cyclohexanecarboxamido)-5-phenylthiophene-2-carboxylate (88 mg, 0.2 mmol) and CDI (39 mg, 0.24 mmol) in DCM (2 mL) was stirred at rt for 1 h. The solvent was evaporated under vacuum and the residue was dissolved in MeCN (2 mL) followed by addition of compound 5-14 (154 mg, 0.2 mmol) and DBU (0.036 mL, 0.24 mmol). The mixture was stirred at 50° C. for 3 h. Then, diluted with EtOAC, washed with water, brine, dry over anhydrous $Na_2SO_4$, filtered and evaporated to dryness. The residue was purified by SiO$_2$ column chromatography to give the title compound (4-3) (138 mg).

MS: (ESI) m/z (M+H) 1206.56

Step 1o: Compound of Formula (4-4): where L is —(CO)—, and $R_7$ is

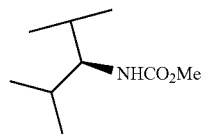

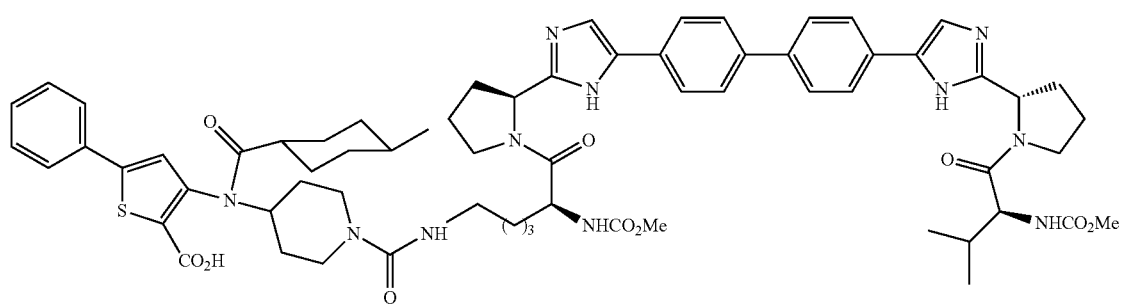

To a solution of compound 4-3 (60 mg, 0.05 mmol) in dioxane (0.5 mL) at rt was added LiOH (0.5 mL 0.5 M aqueous solution, 0.25 mmol). The mixture was then stirred at rt for 4 hours. The mixture was diluted with EtOAC and acidified with 1N HCl. The organic layer was washed with brine, dry over anhydrous $Na_2SO_4$, filtered and evaporated to dryness. The residue was purified by SiO$_2$ column chromatography to give the title compound (4-4) (26 mg).

MS: (ESI) m/z (M+H) 1912.52

The compounds of examples 3-221, wherein $R_7C(O)$— is delineated for each example in Table 2, are prepared via the method delineated in example 1.

TABLE 2

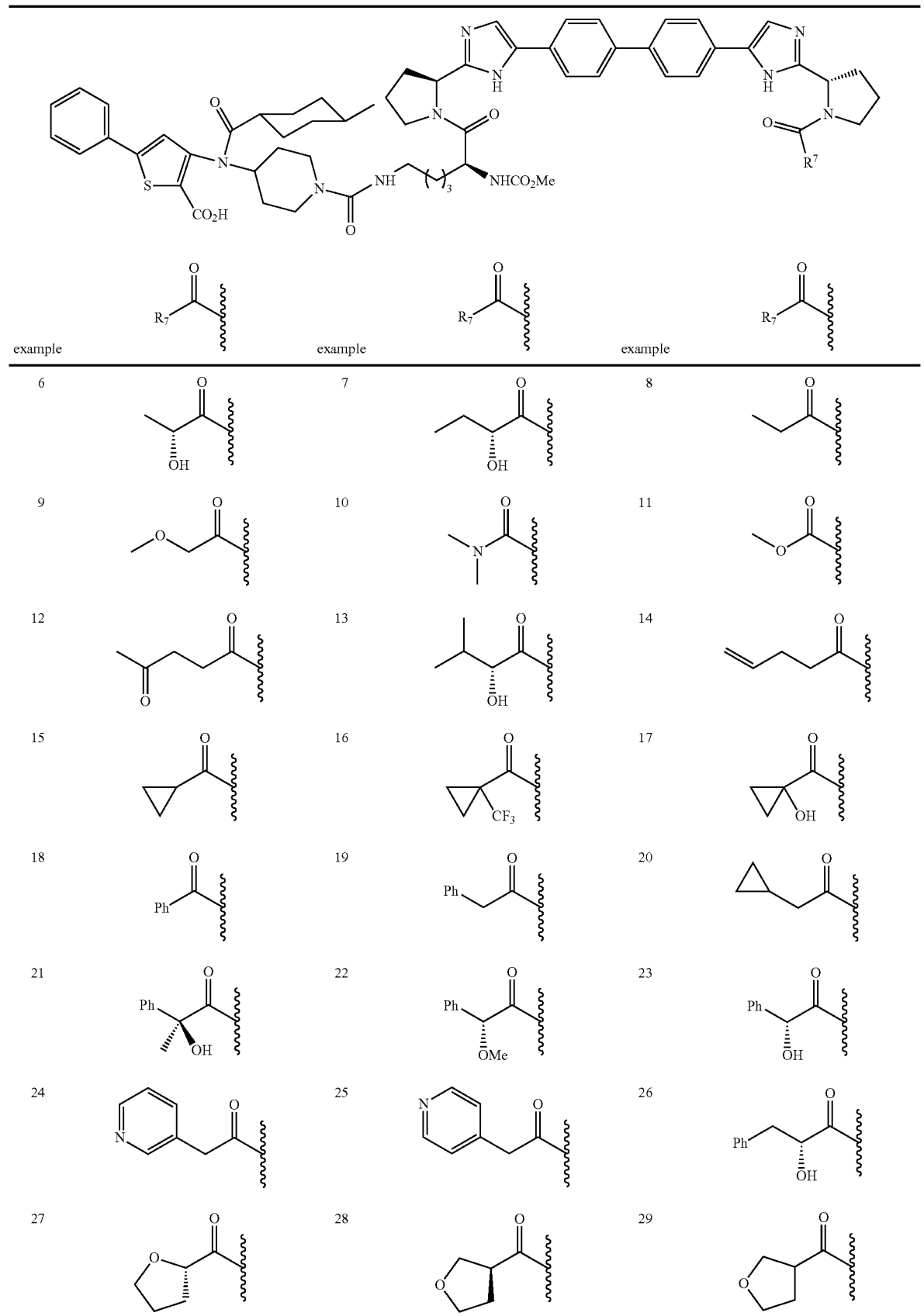

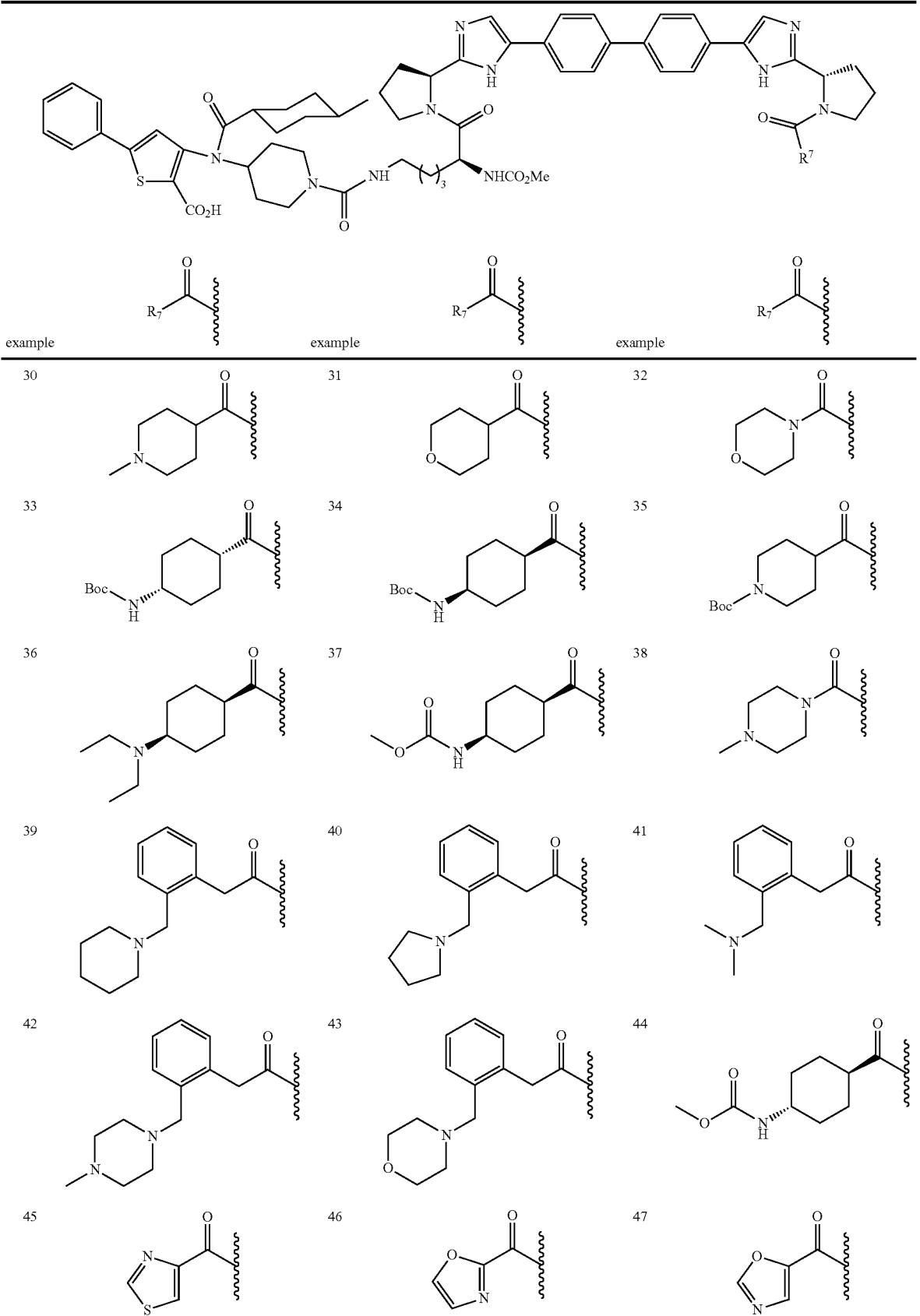

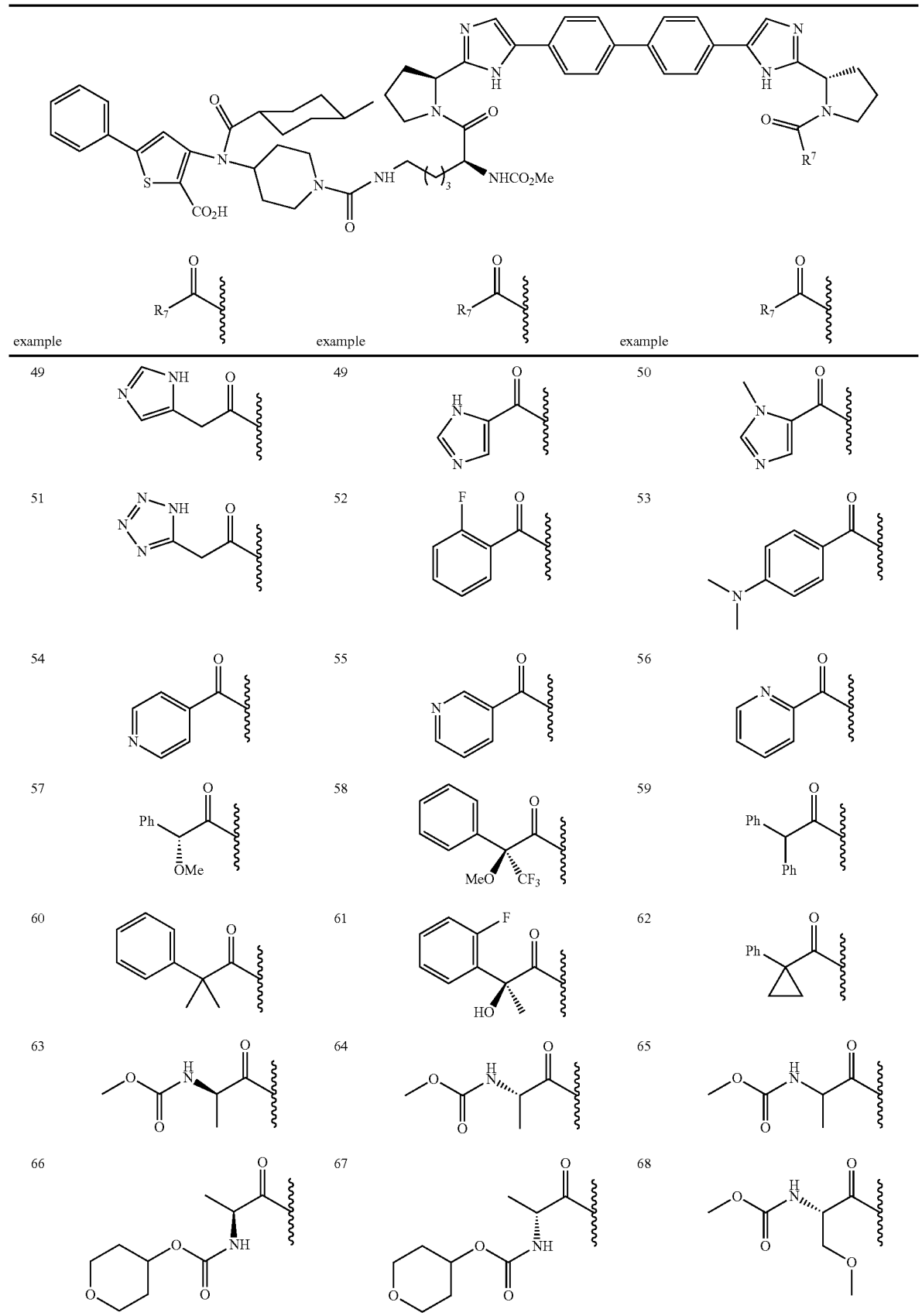

TABLE 2-continued
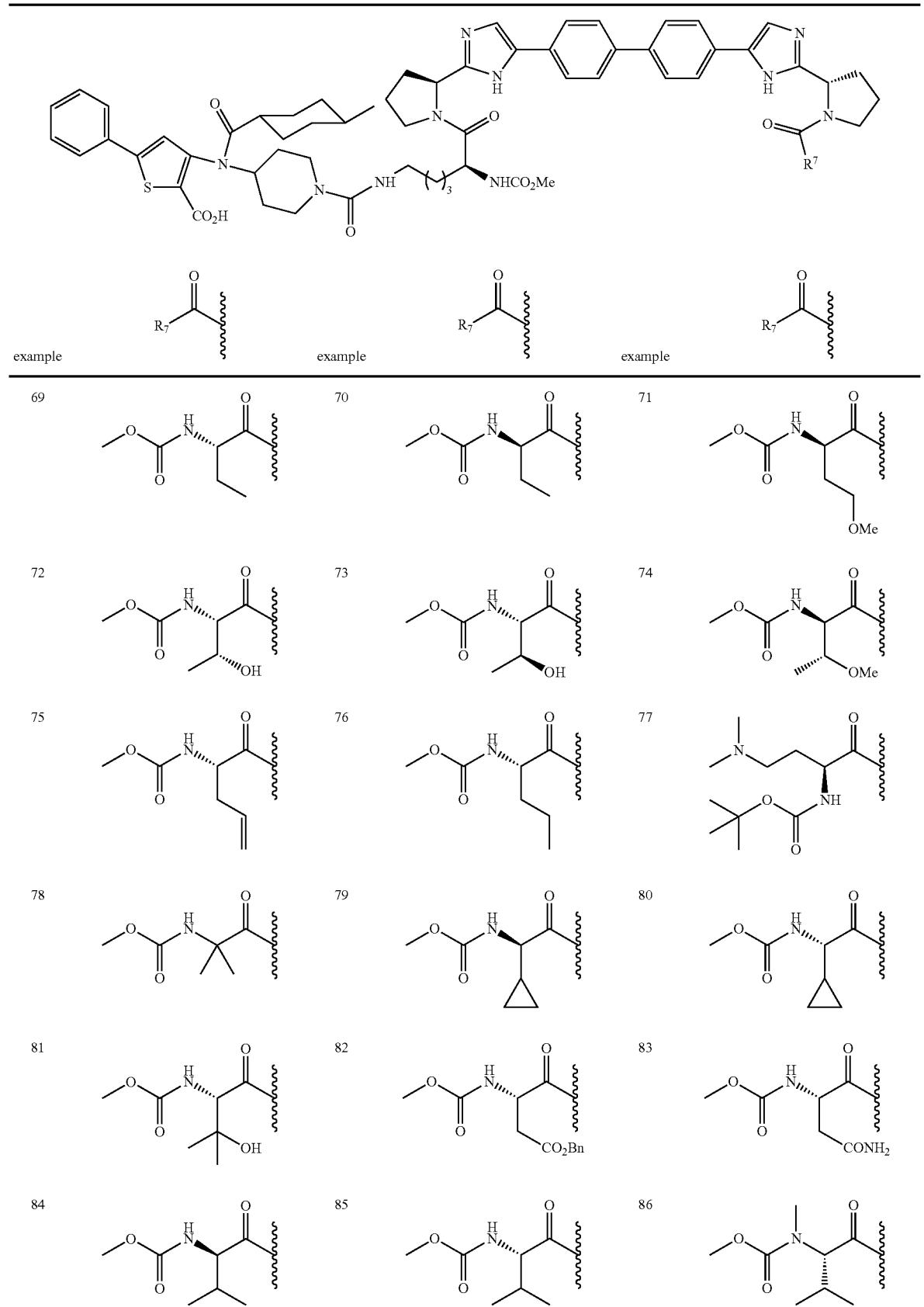

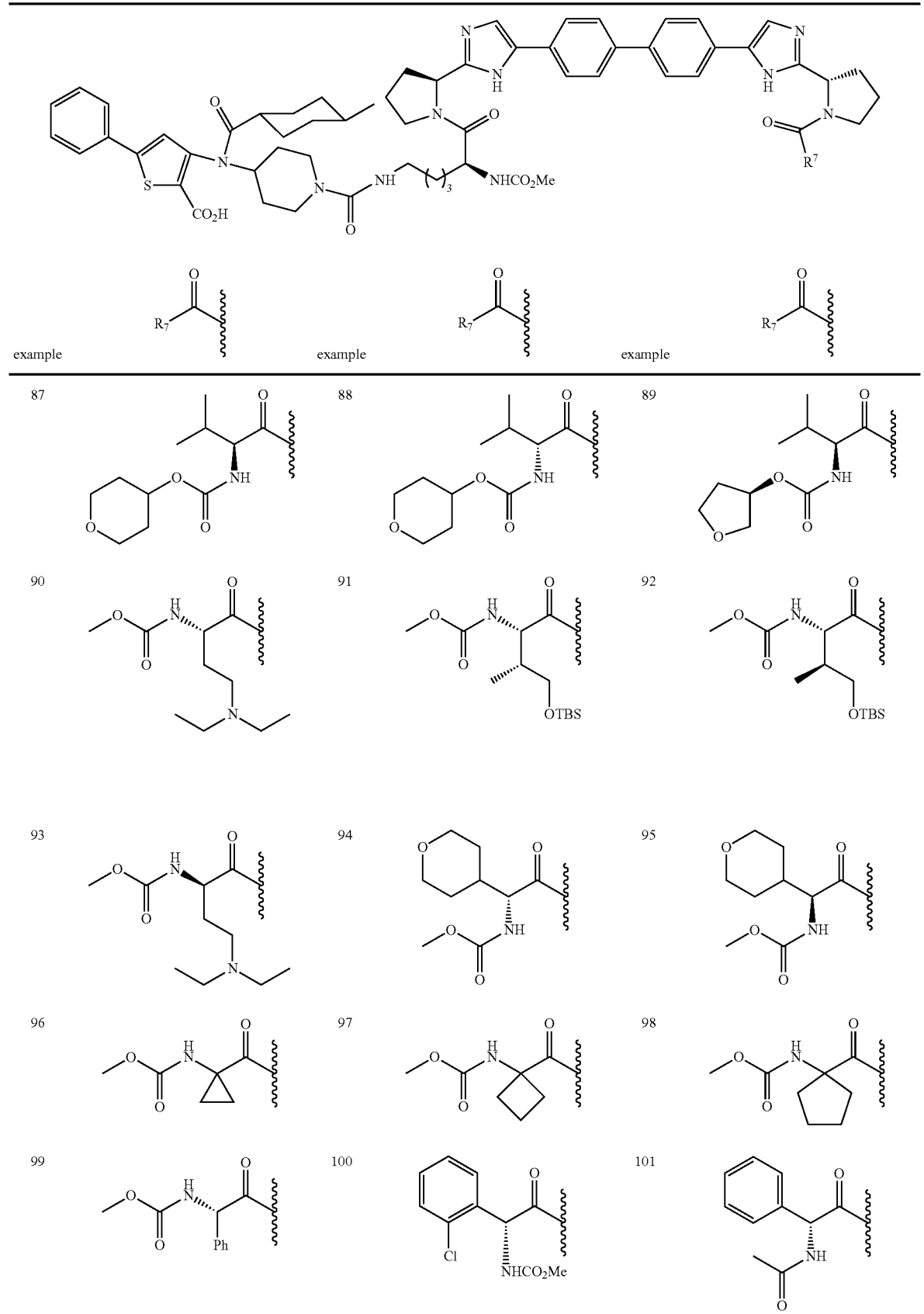

TABLE 2-continued

TABLE 2-continued

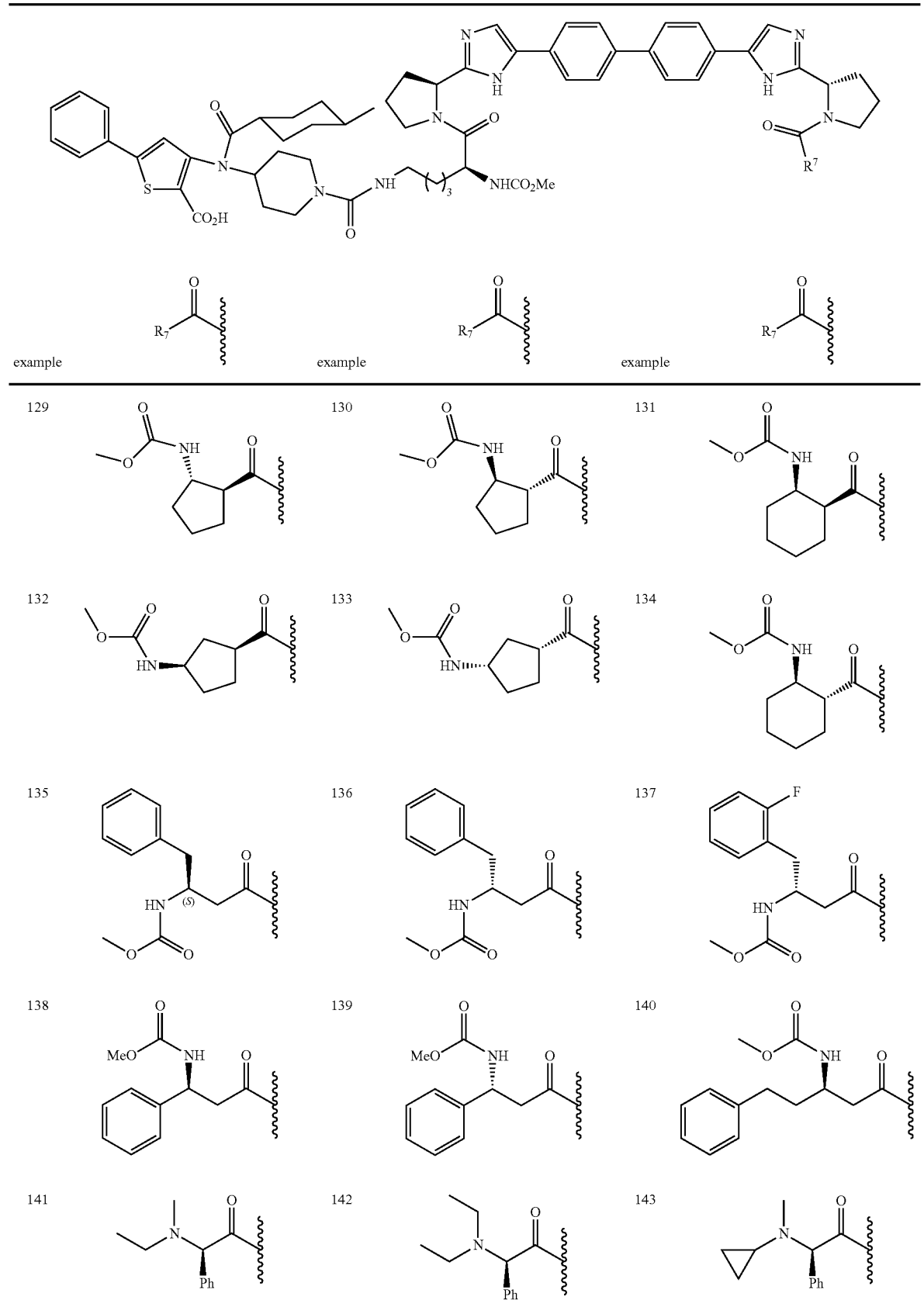

TABLE 2-continued
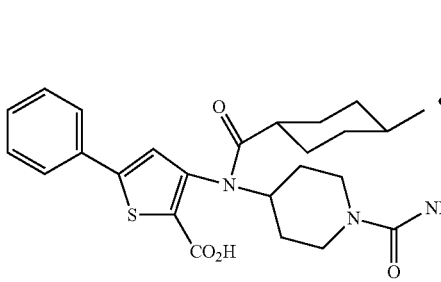
| example | | example | | example | |
|---|---|---|---|---|---|
| 144 | 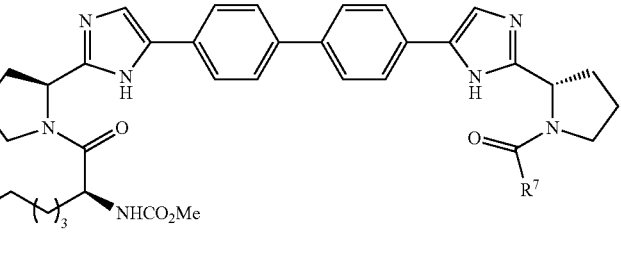 | 145 | 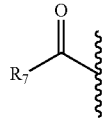 | 146 | 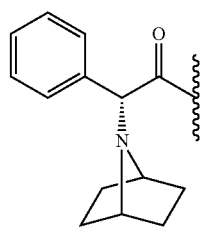 |
| 147 | 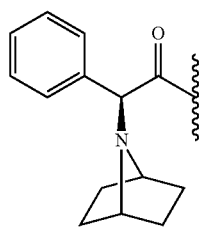 | 148 | 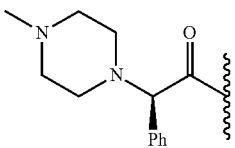 | 149 | 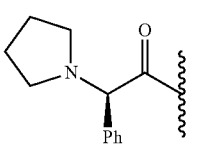 |
| 150 | 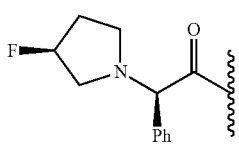 | 151 | 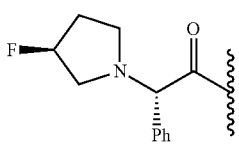 | 152 | 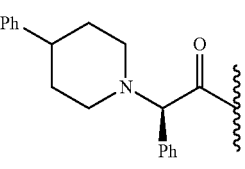 |
| 153 | 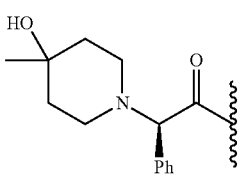 | 154 | 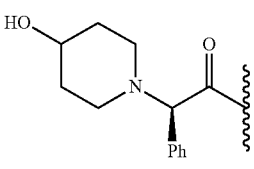 | 155 | 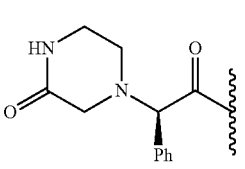 |
| 156 | 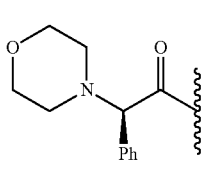 | 157 | 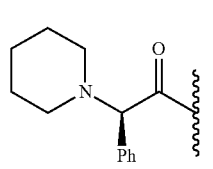 | 158 | 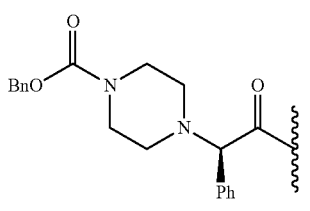 |
| 159 | 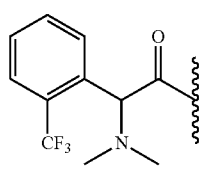 | 160 | 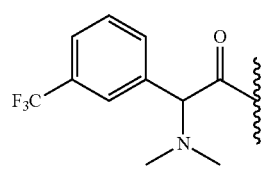 | 161 | 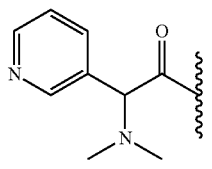 |

TABLE 2-continued
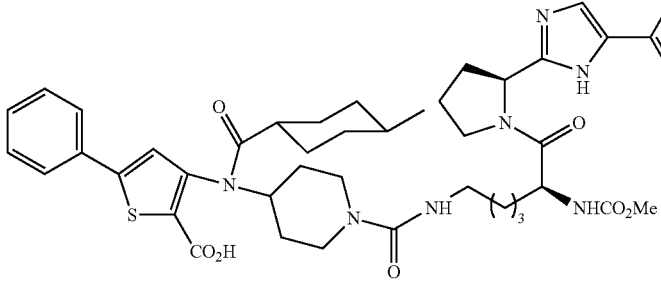
| example | 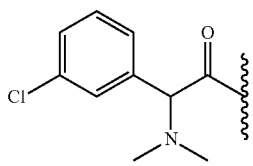 | example | 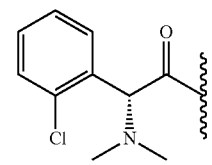 | example | 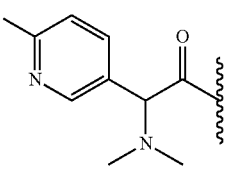 |
|---|---|---|---|---|---|
| 162 | 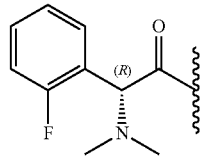 | 163 | 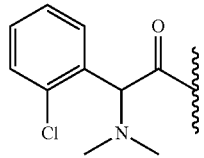 | 164 | 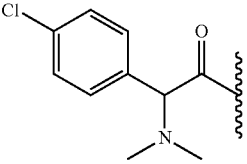 |
| 165 | 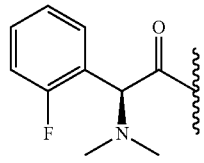 | 166 | 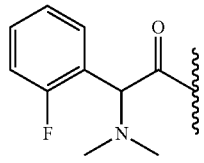 | 167 | 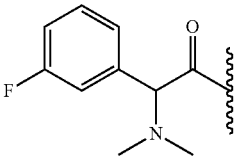 |
| 168 | 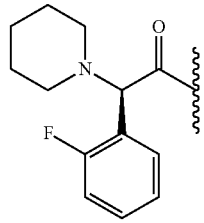 | 169 | 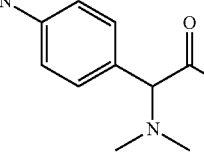 | 170 | 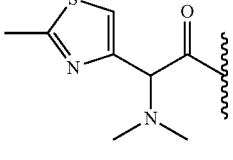 |
| 171 | 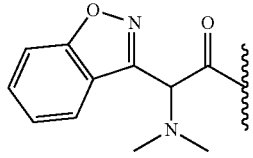 | 172 | 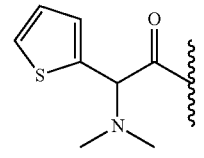 | 173 | 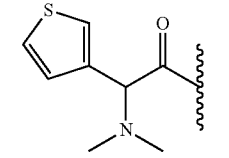 |
| 174 | 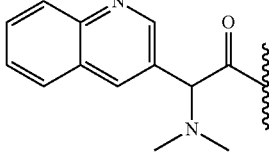 | 175 | 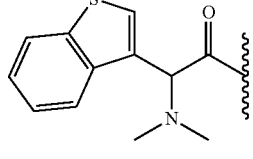 | 176 | 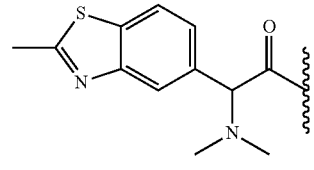 |
| 177 | | 178 | | 179 | |

TABLE 2-continued
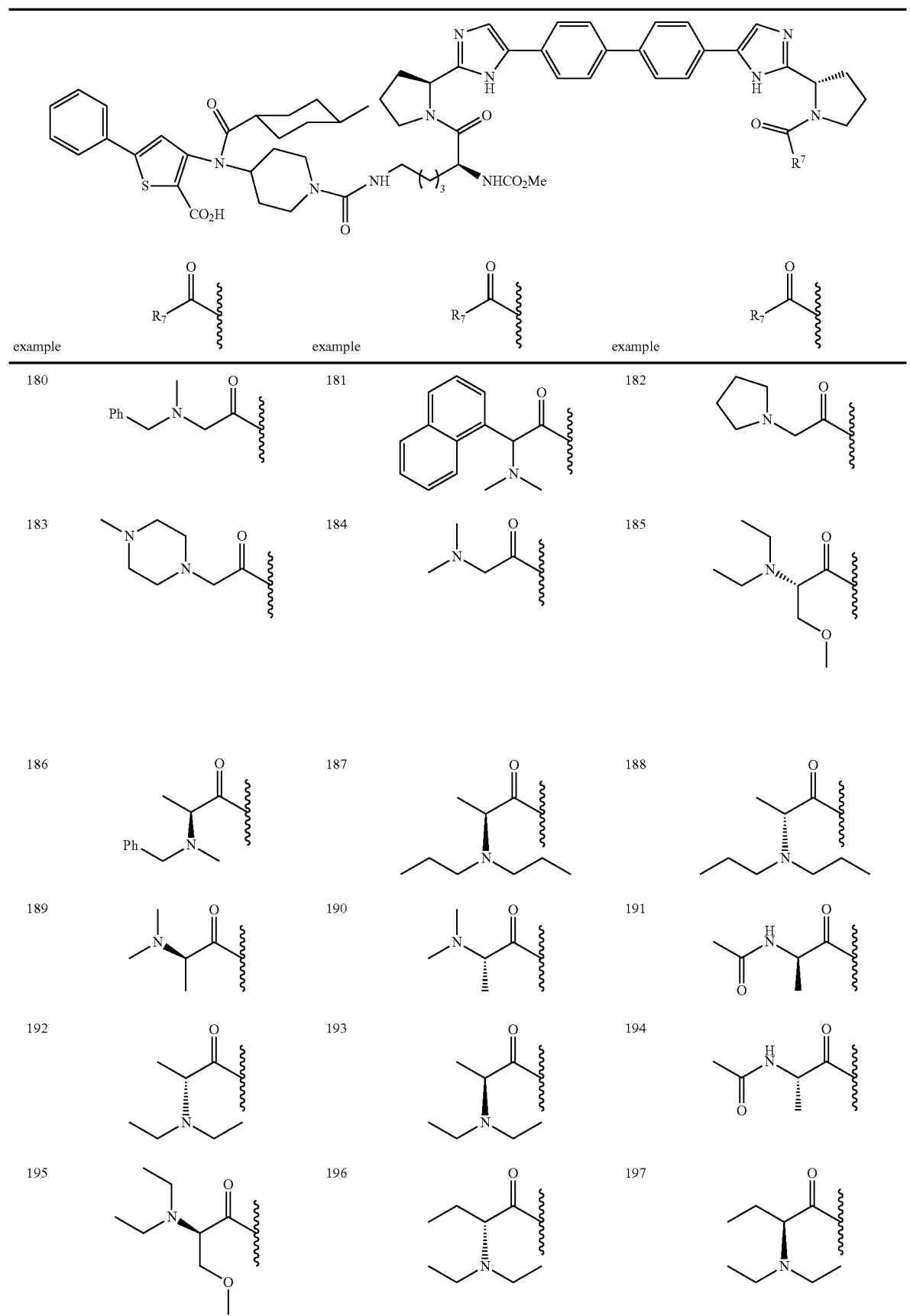

TABLE 2-continued
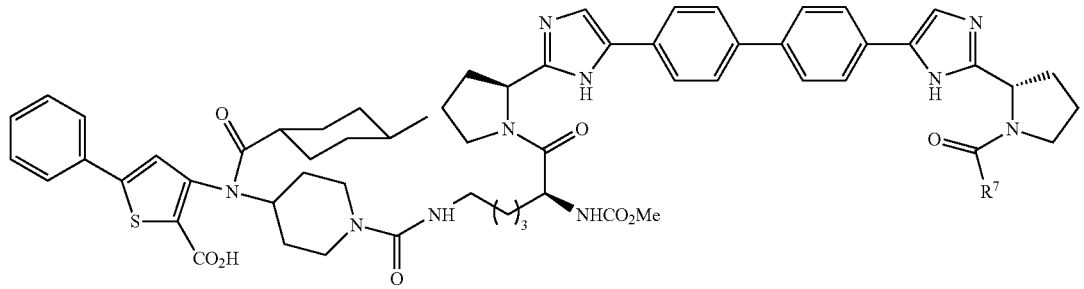
| example | 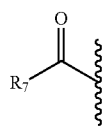 | example | 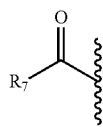 | example | 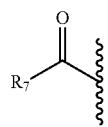 |
|---|---|---|---|---|---|
| 198 | 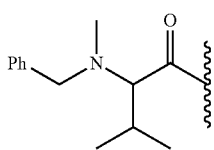 | 199 | 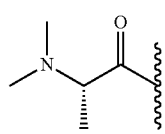 | 200 | 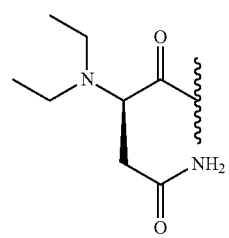 |
| 201 | 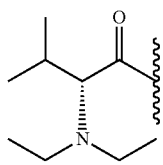 | 202 | 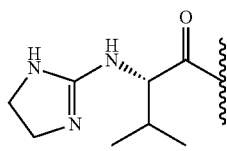 | 203 | 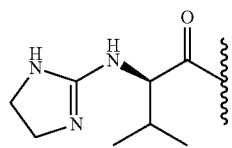 |
| 204 | 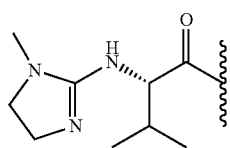 | 205 | 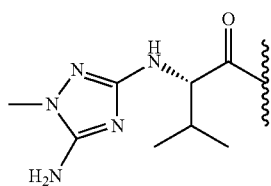 | 206 | 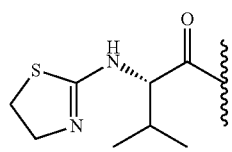 |
| 207 | 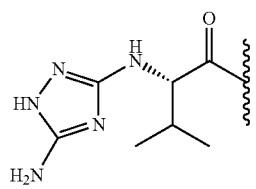 | 208 | 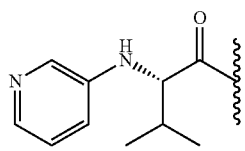 | 209 | 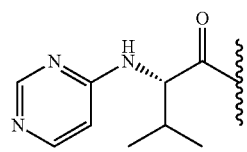 |

TABLE 2-continued
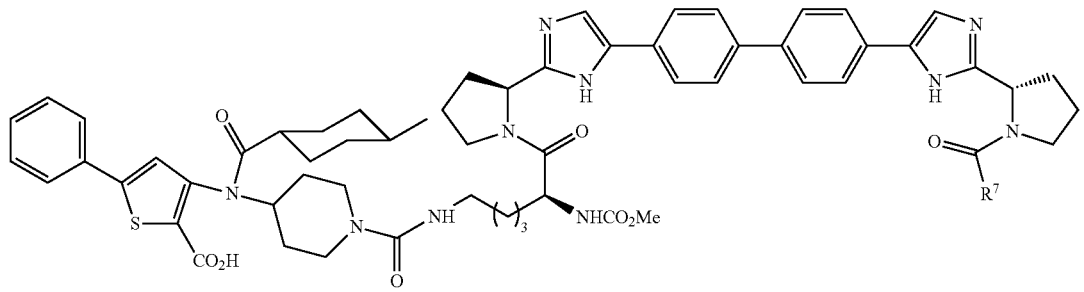
| example | 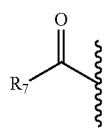 | example | 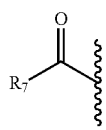 | example | 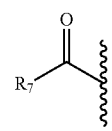 |
|---|---|---|---|---|---|
| 210 | 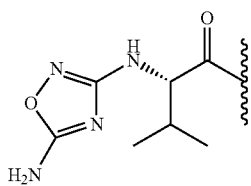 | 211 | 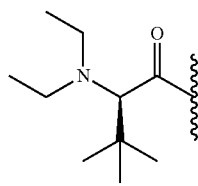 | 212 | 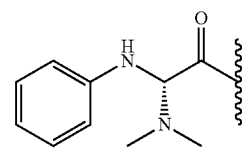 |
| 213 | 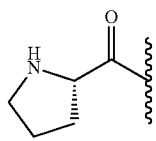 | 214 | 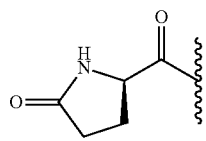 | 215 | 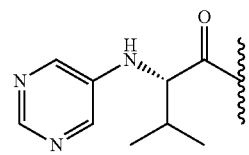 |
| 216 | 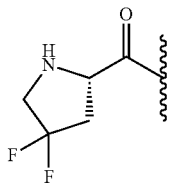 | 217 | 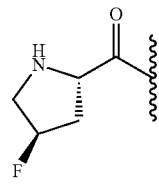 | 218 | 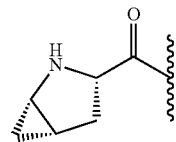 |
| 219 | 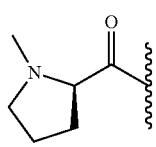 | 220 | 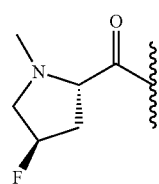 | 221 | 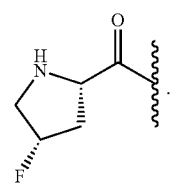 |

Example 222

Compound of formula (4-4): where L is —CH₂CH₂O(CO)—, and R₇ is

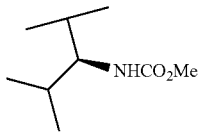

Step 222a: methyl 3-((1r,4r)-N-(1-(2-(tert-butyldimethylsilyloxy)ethyl)piperidin-4-yl)-4-methylcyclohexanecarboxamido)-5-phenylthiophene-2-carboxylate

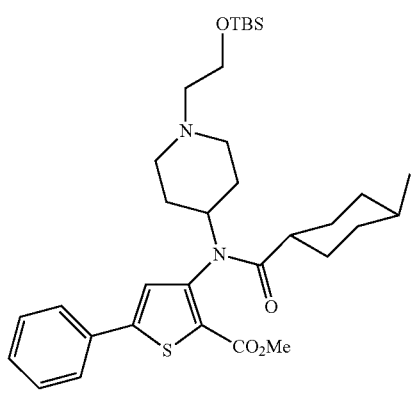

To a solution of methyl 3-((1r,4r)-4-methyl-N-(piperidin-4-yl)cyclohexanecarboxamido)-5-phenylthiophene-2-carboxylate (132 mg, 0.3 mmol) in DCE (2.0 ml) was added sequentially (tert-butyldimethylsilyloxy)acetaldehyde (209 mg, 1.2 mmol), AcOH (0.069 mL, 1.2 mmol) and NaBH(OAc)₃ (127 mg, 0.6 mmol) and stirred for 2 h. The reaction mixture was dilute with EtOAc then quenched with sat. NaHCO₃. The aqueous phase was extracted with EtOAc, the combined extract was washed with brine, dried on Na₂SO₄ and evaporated to dryness. The crude was purified on silica gel column to give the title compound (136 mg, 76%).

MS: (ESI) m/z (M+H) 599.29

Step 222b: methyl 3-((1r,4r)-N-(1-(2-hydroxyethyl)piperidin-4-yl)-4-methylcyclohexanecarboxamido)-5-phenylthiophene-2-carboxylate

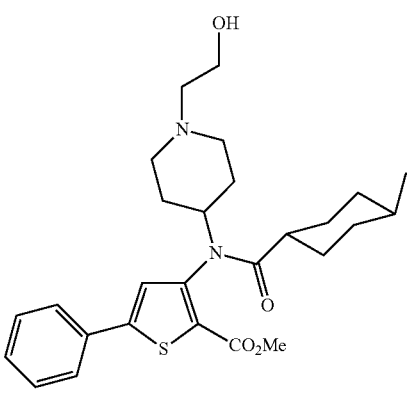

To a solution of methyl 3-((1r,4r)-N-(1-(2-(tert-butyldimethylsilyloxy)ethyl)piperidin-4-yl)-4-methylcyclohexanecarboxamido)-5-phenylthiophene-2-carboxylate (119 mg, 0.2 mmol) in DCM (3.0 ml) at 0° C. was added TFA (3 mL) at 0° C. and stirred for 1 h. The reaction mixture was evaporated to dryness. The residue was diluted with DCM, washed with aqueous 10% Na₂CO₃ solution, brine, dried on Na₂SO₄. The crude was purified on silica gel column to give the title compound (86 mg, 88%).

MS: (ESI) m/z (M+H) 485.21

Step 222c: Compound of Formula (4-3): where L is —CH₂CH₂O(CO)—, and R₇ is

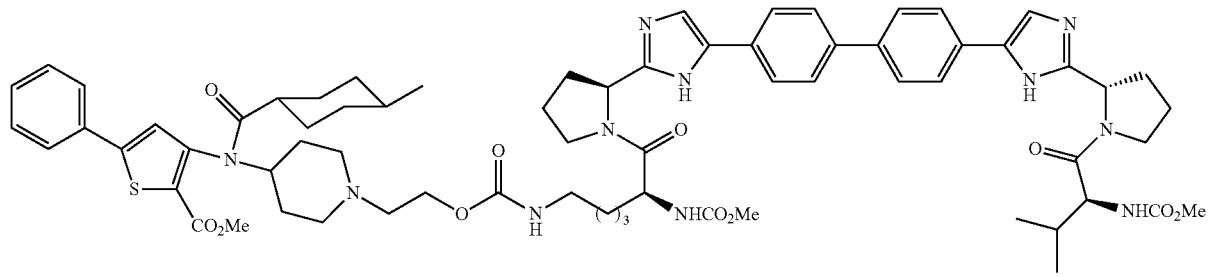

A mixture of methyl 3-((1r,4r)-N-(1-(2-hydroxyethyl)piperidin-4-yl)-4-methyl cyclohexanecarboxamido)-5-phenylthiophene-2-carboxylate (97 mg, 0.2 mmol) and CDI (39 mg, 0.24 mmol) in DCM (2 mL) was stirred at rt for 1 h. The solvent was evaporated under vacuum and the residue was dissolved in MeCN (2 mL) followed by addition of compound 5-14 (154 mg, 0.2 mmol) and DBU (0.036 mL, 0.24 mmol). The mixture was stirred at 50° C. for 3 h. Then, diluted with EtOAC, washed with water, brine, dry over anhydrous Na$_2$SO$_4$, filtered and evaporated to dryness. The residue was purified by SiO$_2$ column chromatography to give the title compound (4-3) (119 mg).

MS: (ESI) m/z (M+H) 1250.58

Step 222d: Compound of Formula (4-4): where L is —CH$_2$CH$_2$O(CO)—, and R$_7$ is

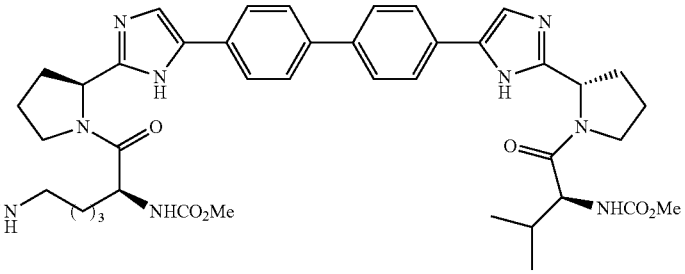

To a solution of compound 4-3 (63 mg, 0.05 mmol) in dioxane (0.5 mL) at rt was added LiOH (0.5 mL 0.5 M aqueous solution, 0.25 mmol). The mixture was then stirred at rt for 4 hours. The mixture was diluted with EtOAC and acidified with to PH 4. The organic layer was washed with brine, dry over anhydrous Na$_2$SO$_4$, filtered and evaporated to dryness. The residue was preparative chromatography to give the title compound (4-4) (19 mg).

MS: (ESI) m/z (M+H) 1236.56

Compounds of examples 222-440, wherein R$_7$C(O)— is delineated for each example in Table 3, are prepared via the method delineated in example 222.

TABLE 3

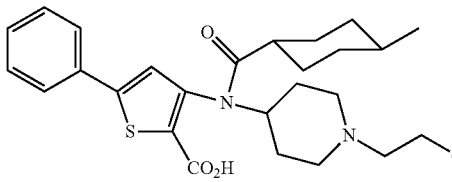

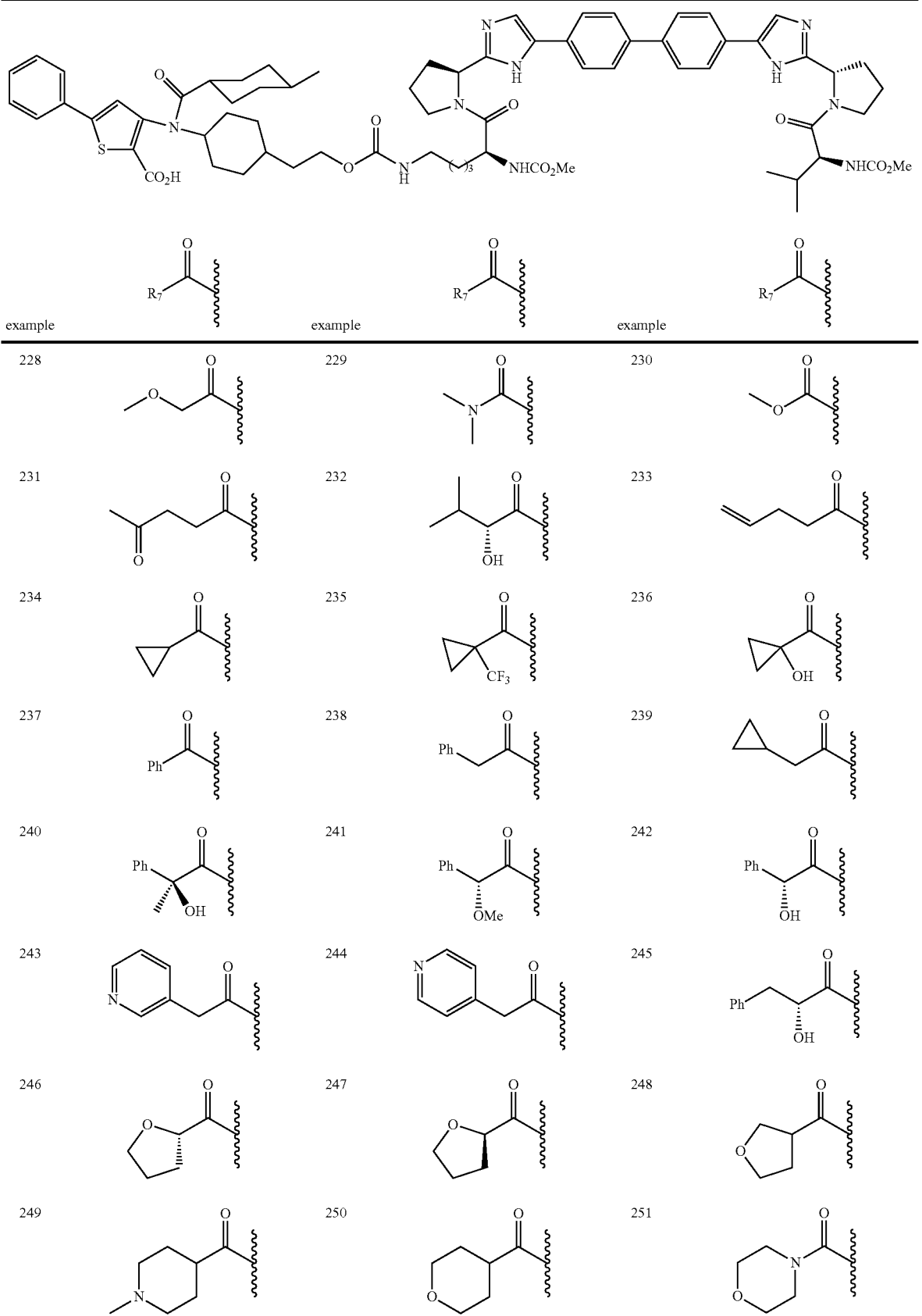

TABLE 3-continued
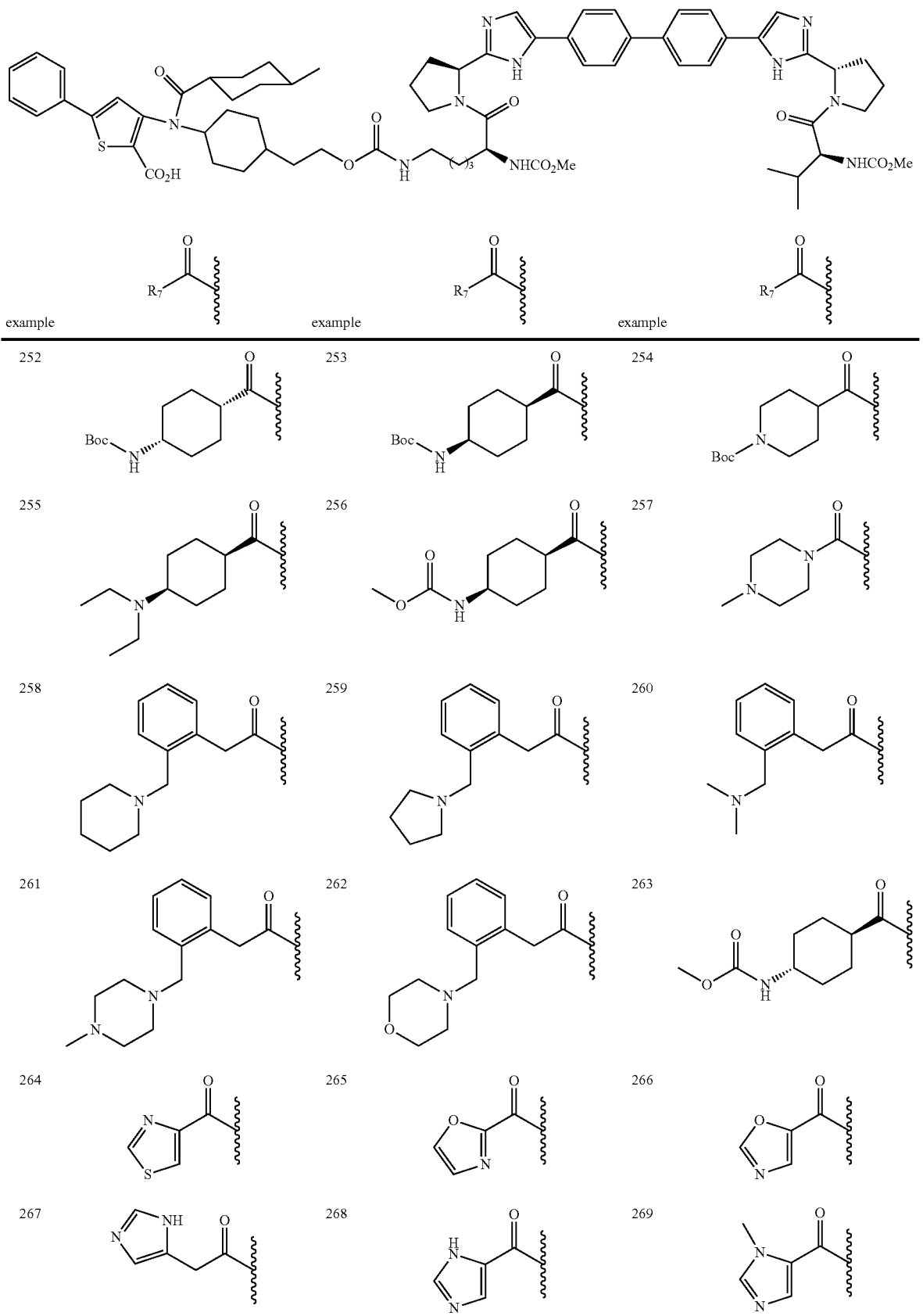

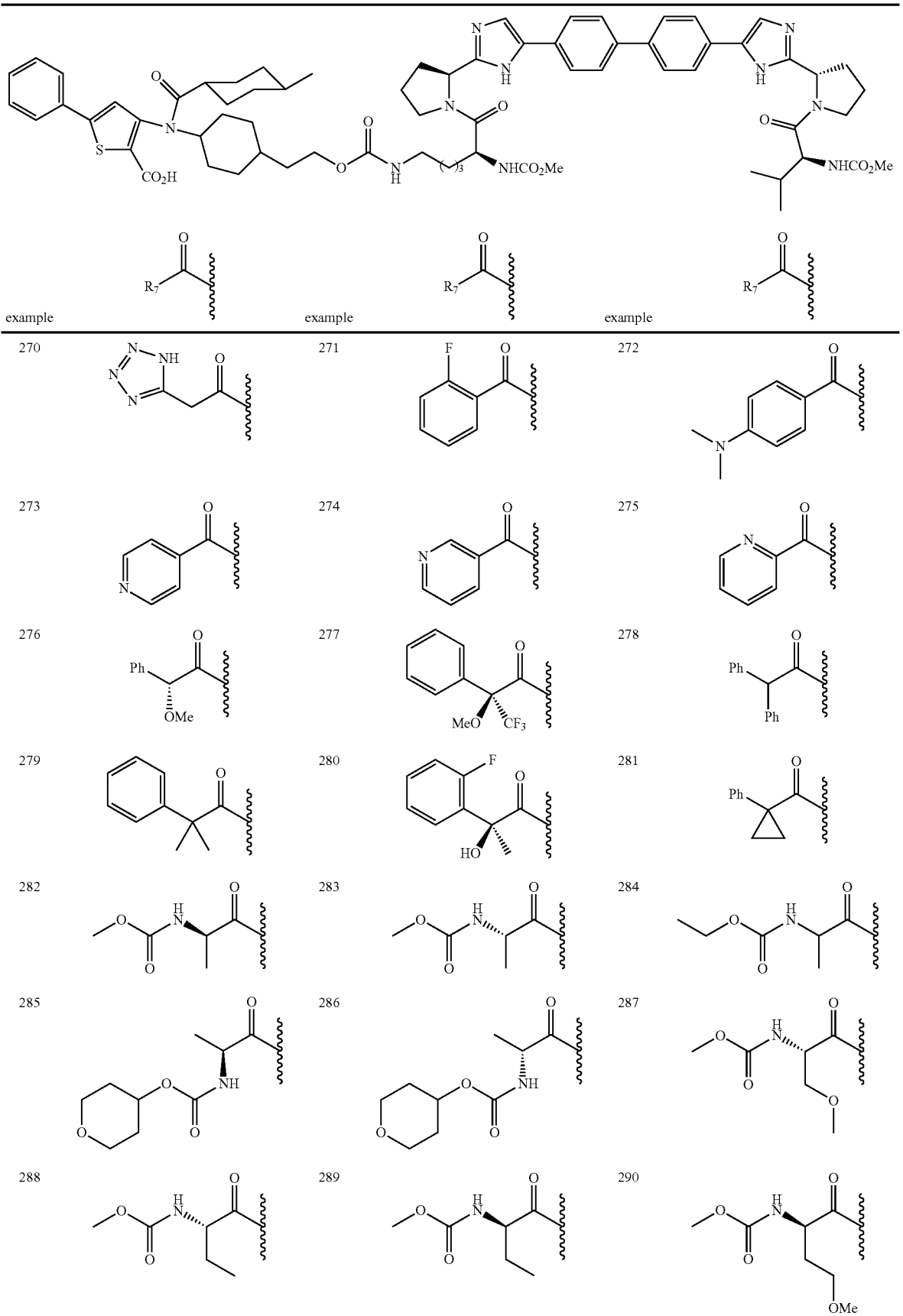

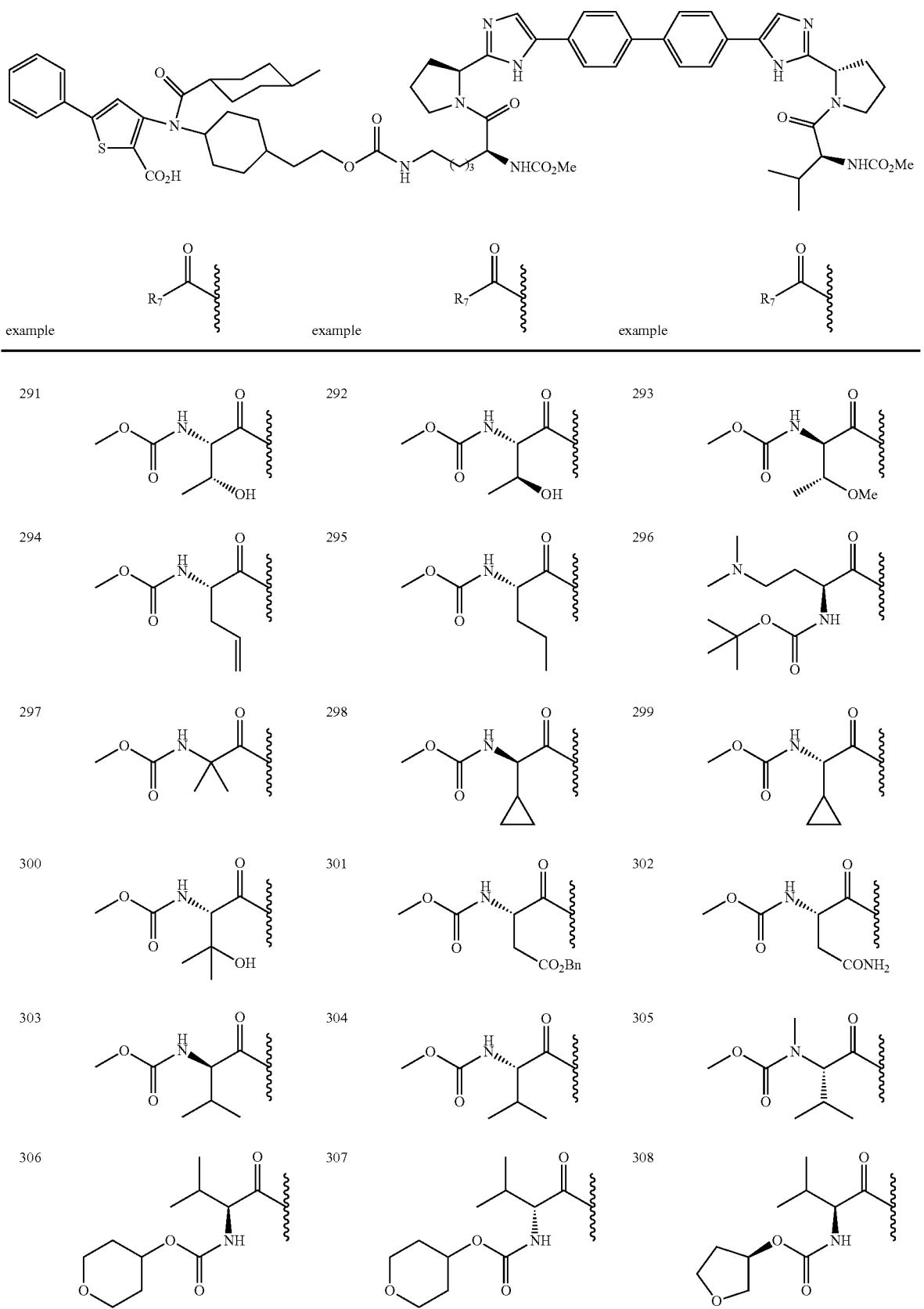

TABLE 3-continued
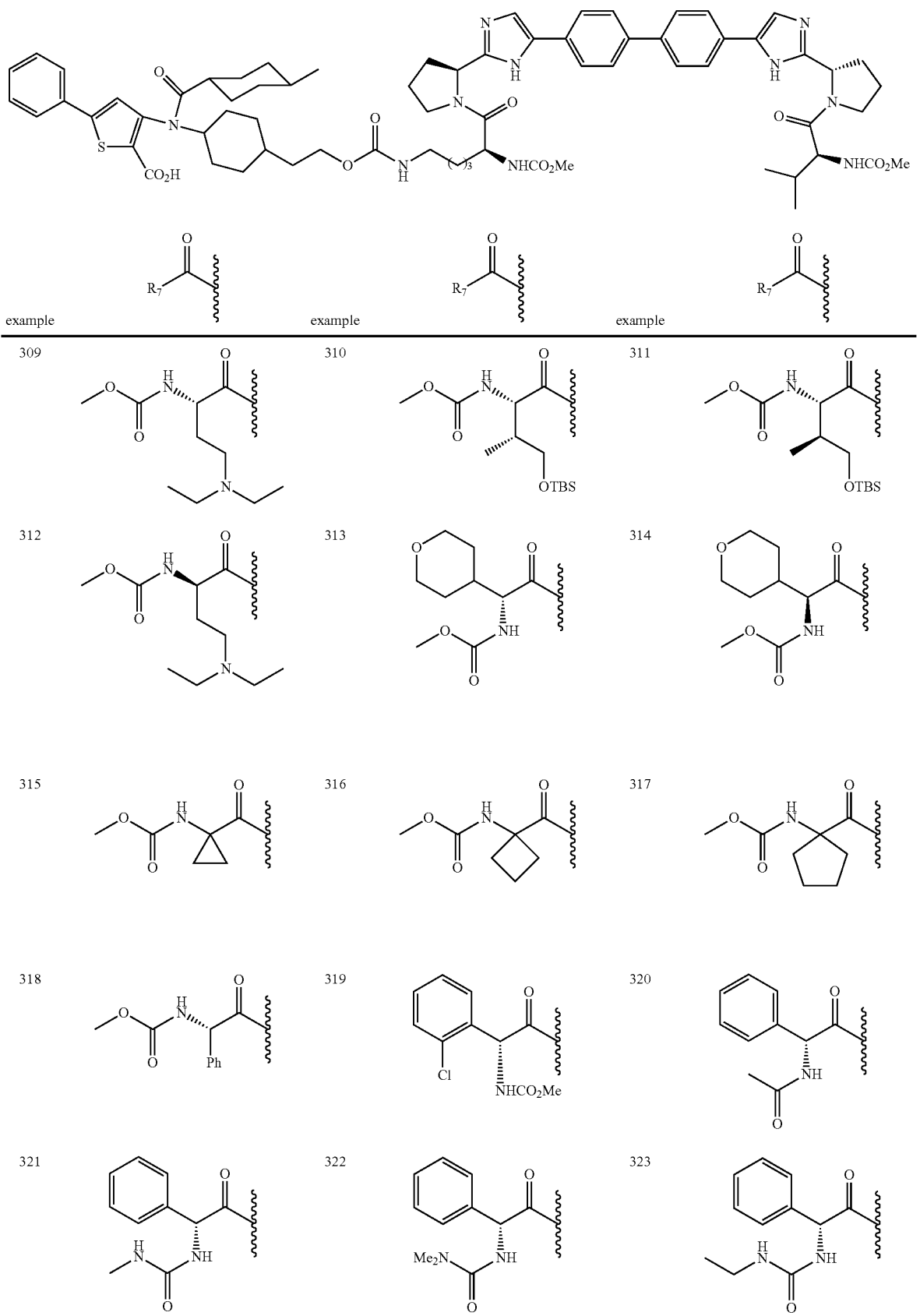

TABLE 3-continued
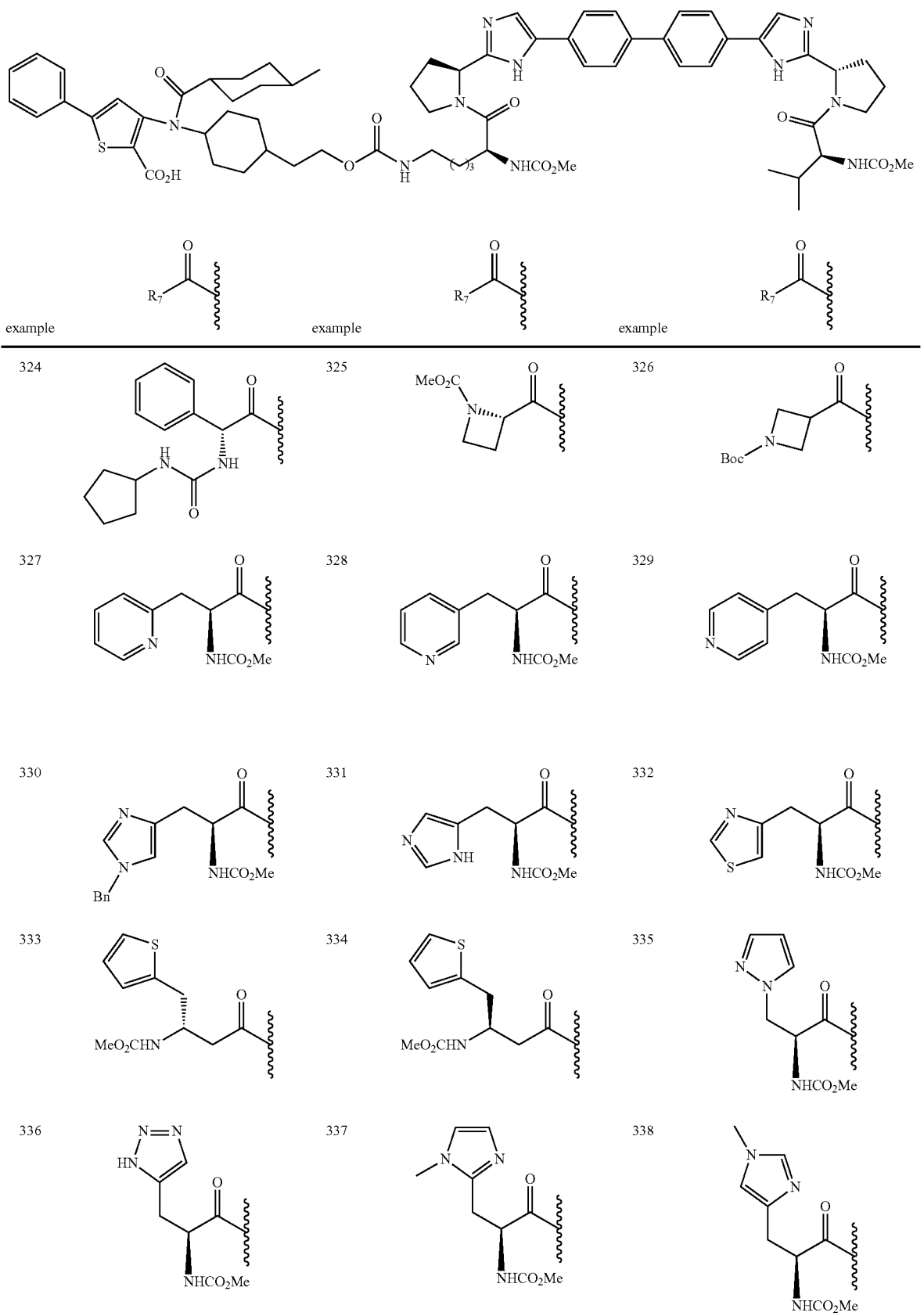

TABLE 3-continued
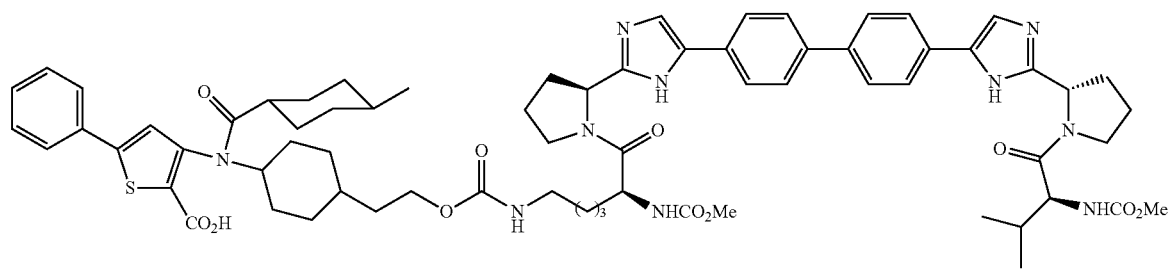
| example | | example | | example | |
|---|---|---|---|---|---|
| 339 | 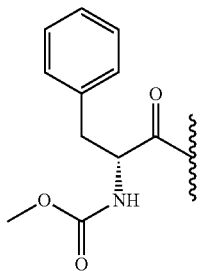 | 340 | 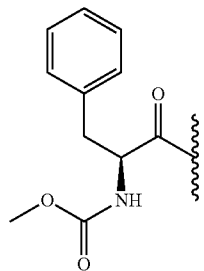 | 341 | 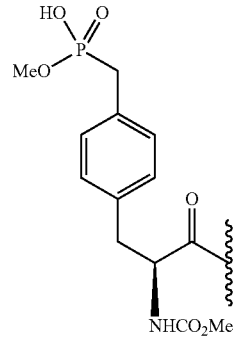 |
| 342 | 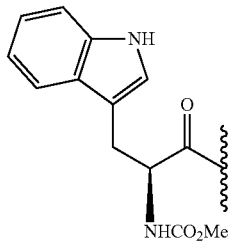 | 343 | 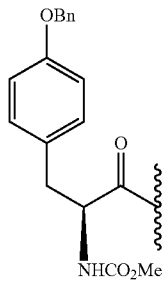 | 344 | 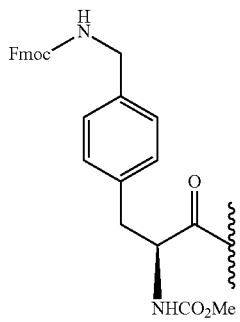 |
| 345 | 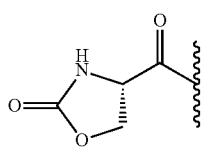 | 346 | 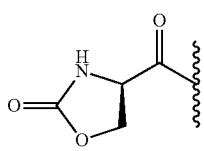 | 347 | 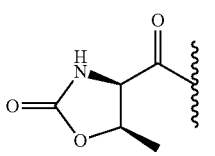 |
| 348 | 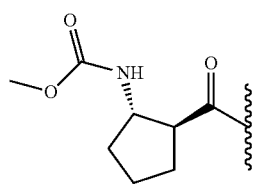 | 349 | 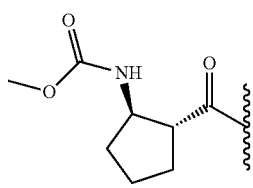 | 350 | 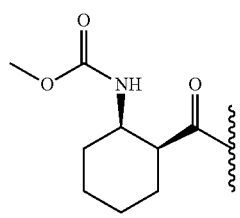 |

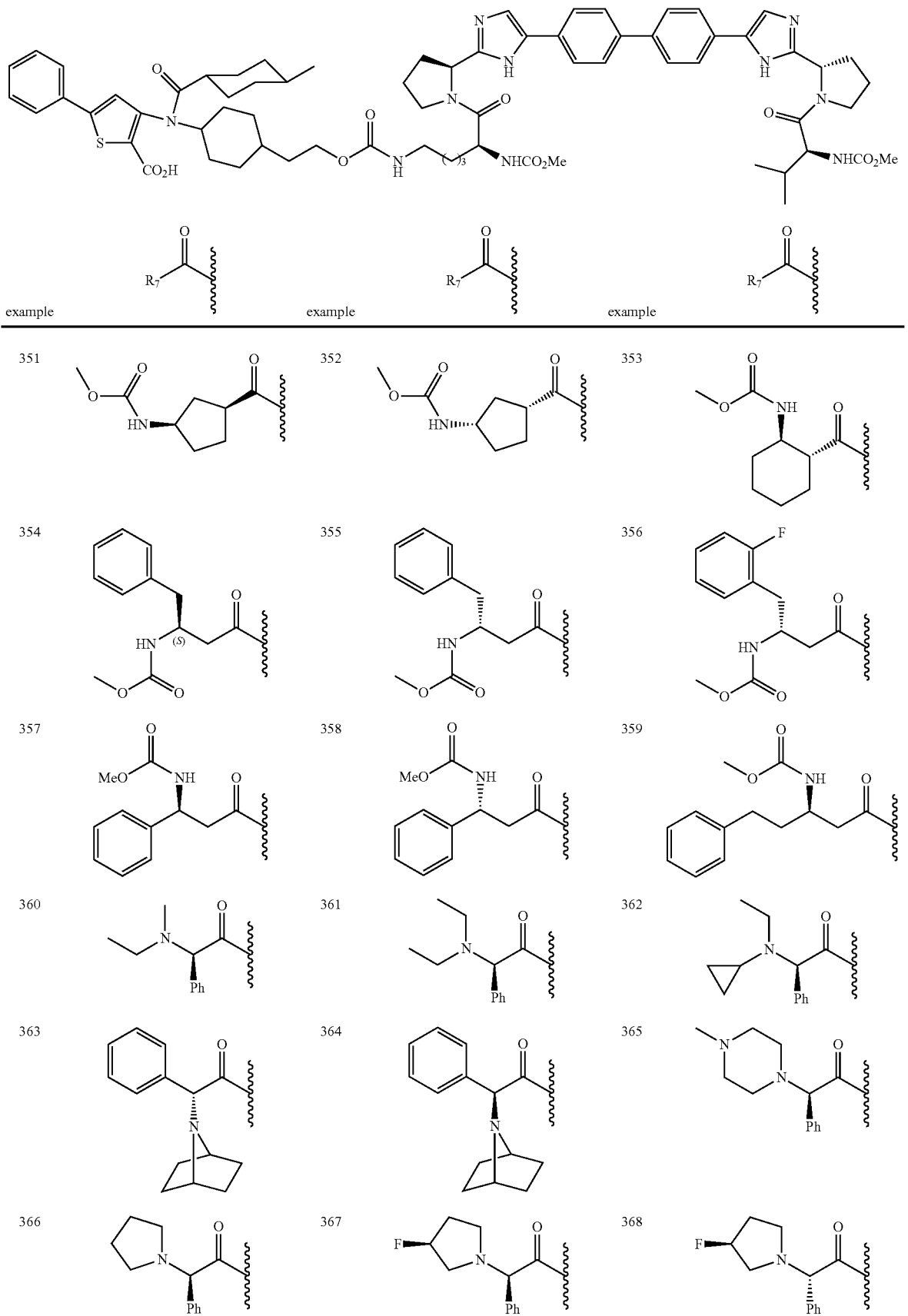

TABLE 3-continued
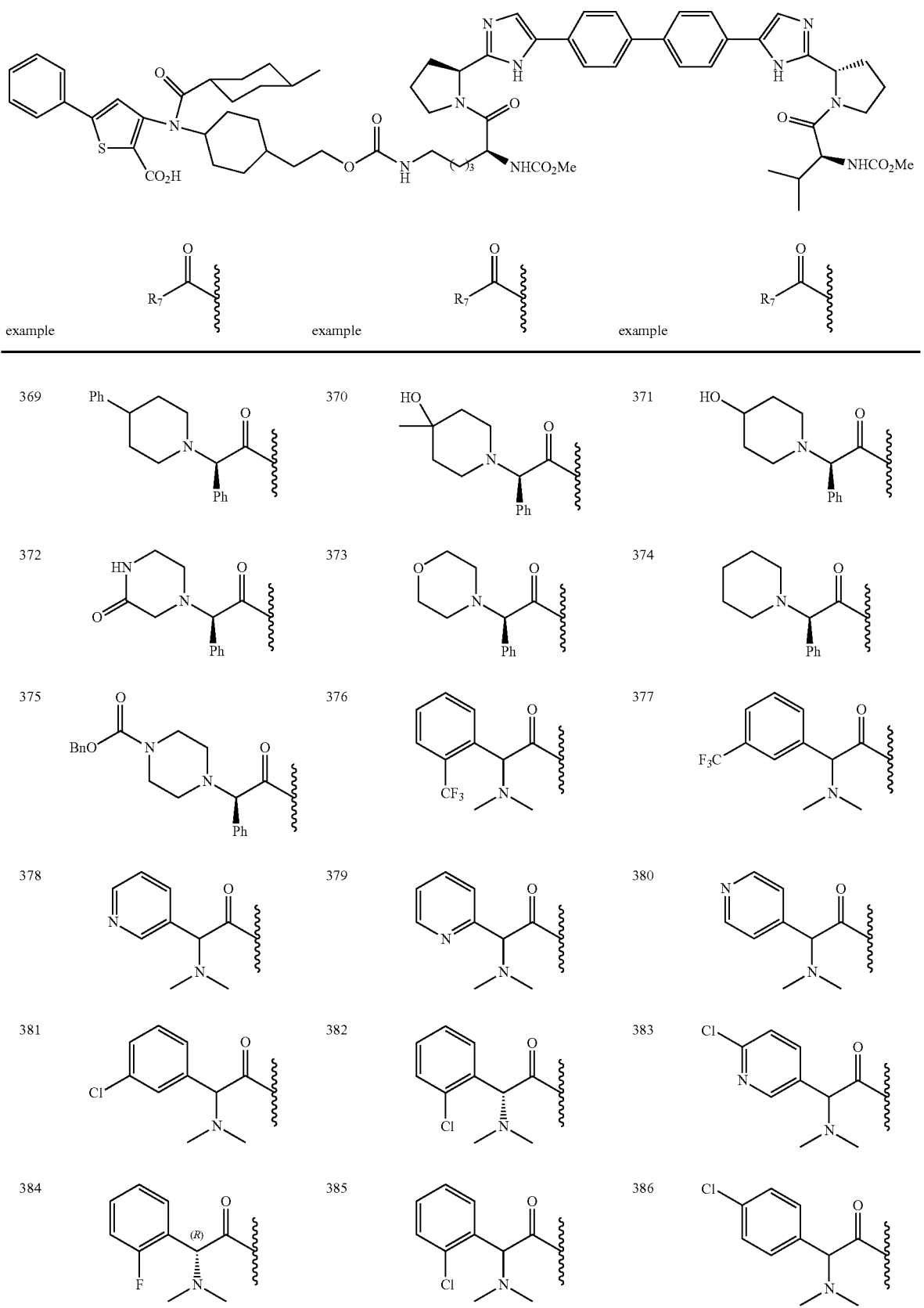

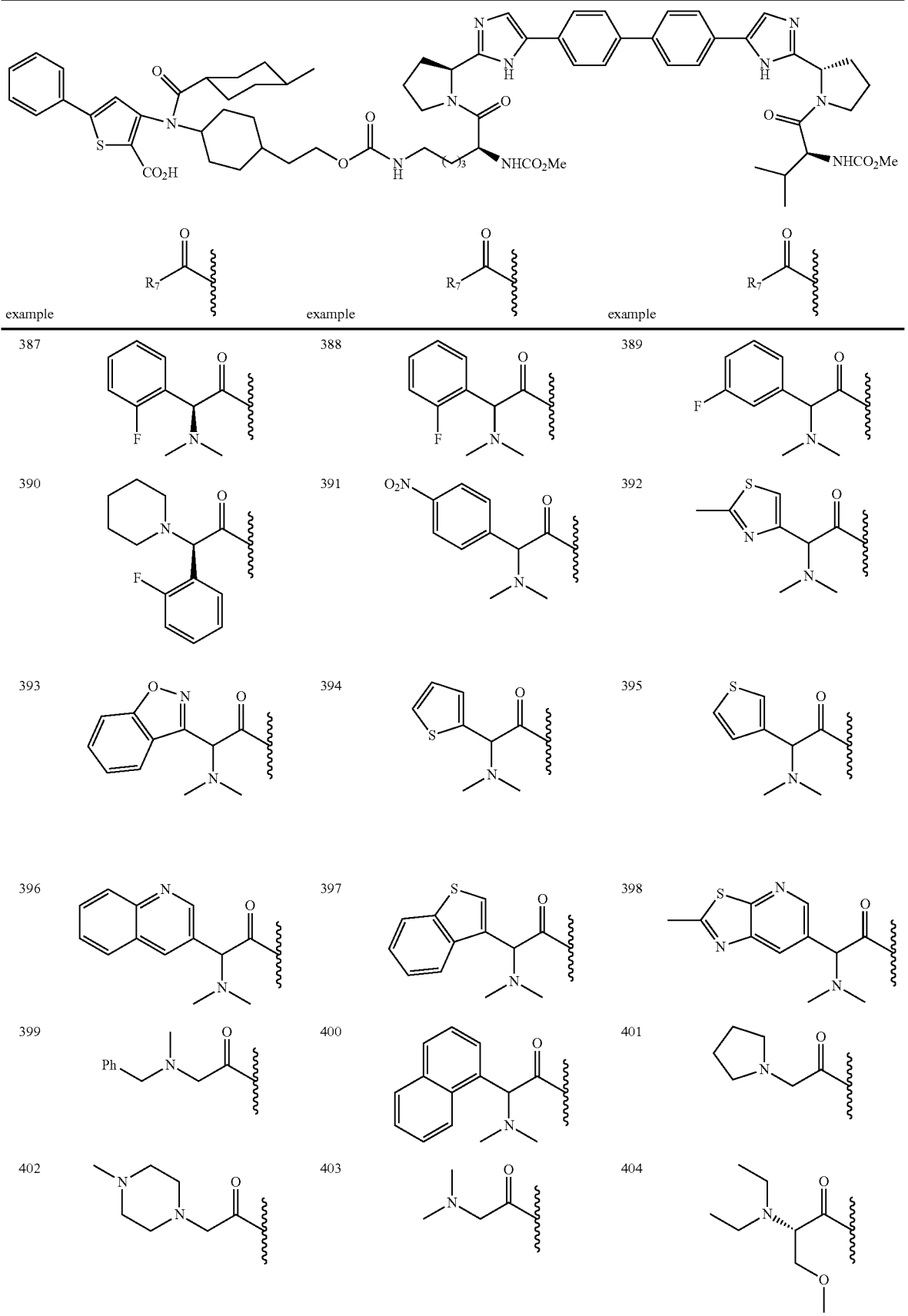

TABLE 3-continued
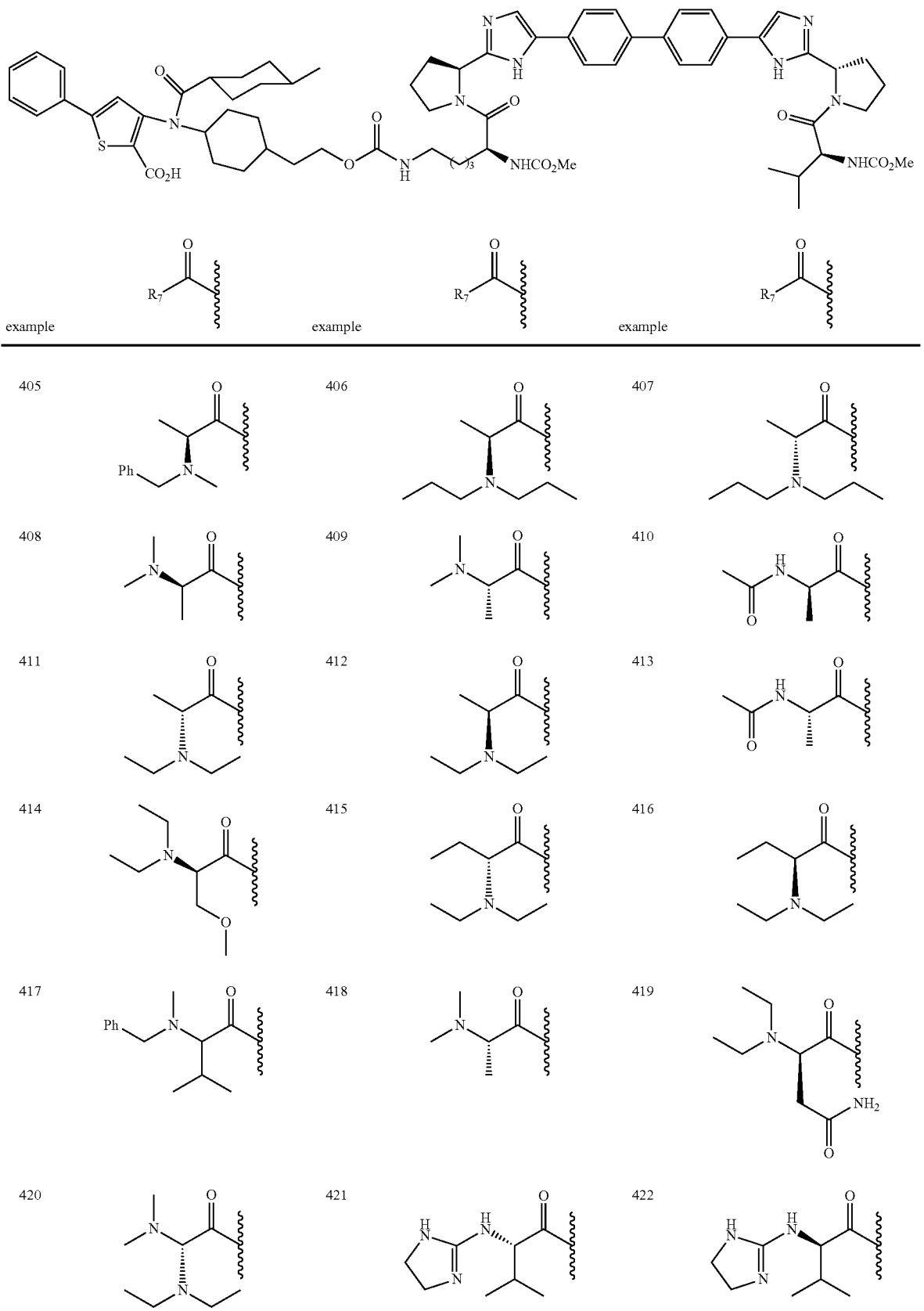

TABLE 3-continued
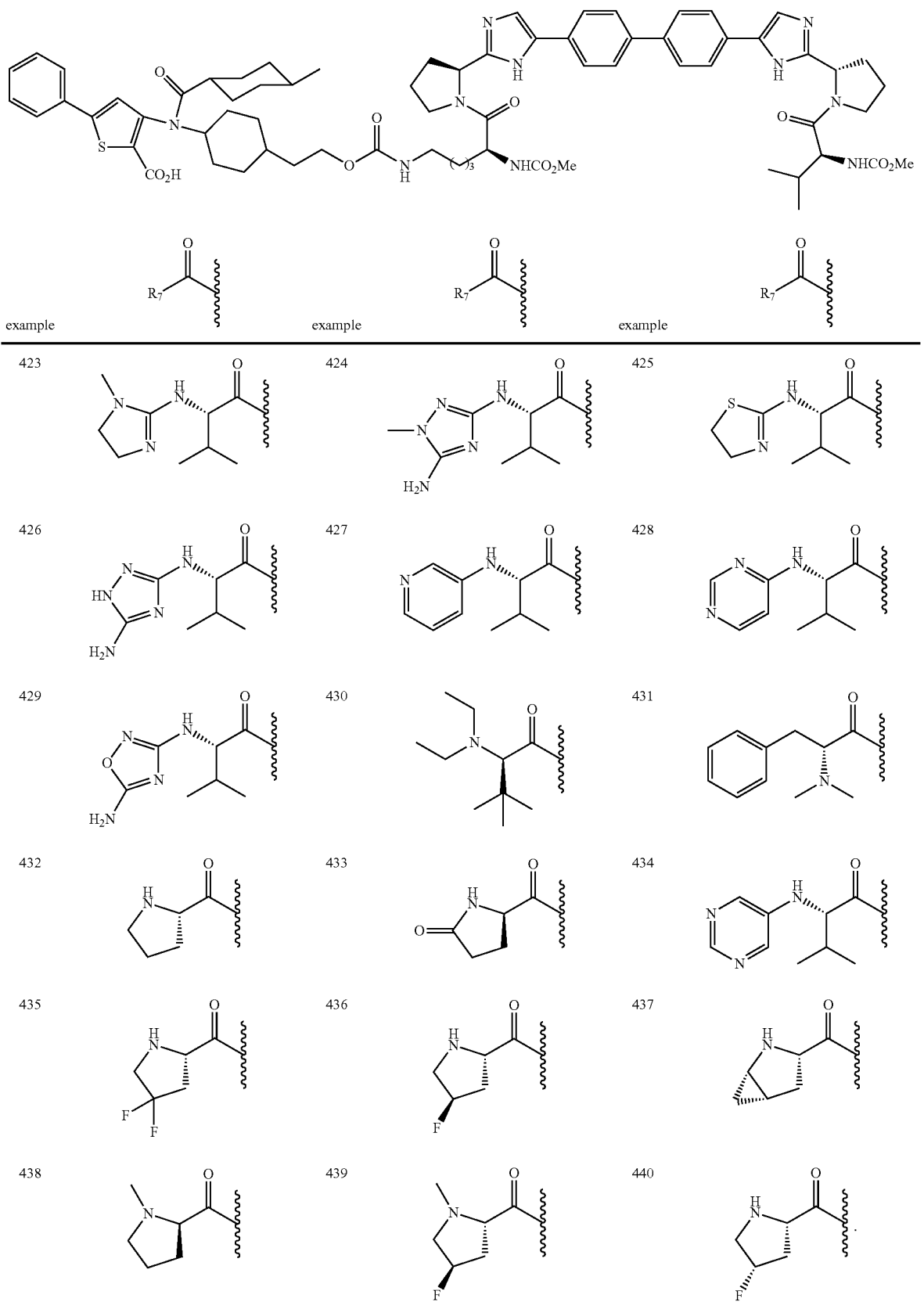

What is claimed is:

1. A compound represented by the formula (I):

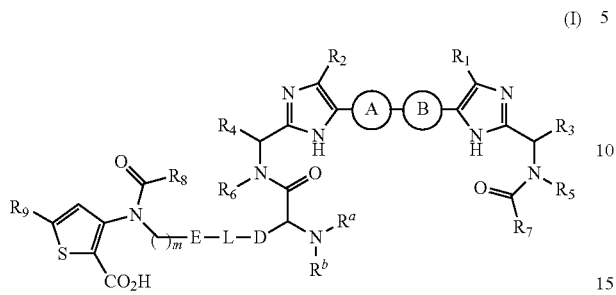

or a pharmaceutically acceptable salt, ester or prodrug thereof, wherein:

Ring A and ring B are each independently selected from:
   a) Phenyl;
   b) Substituted phenyl;
   c) Six membered heteroaryl containing one, two or three nitrogen atoms;
   d) Substituted six membered heteroaryl containing one, two or three nitrogen atoms;

$R_1$ and $R_2$ are each independently selected from:
   a) Hydrogen;
   b) Deuterium;
   c) Halogen;
   d) $R_{11}$, where $R_{11}$ is selected from:
      1) $C_1$-$C_{12}$ alkyl;
      2) Substituted $C_1$-$C_{12}$ alkyl;
      3) $C_2$-$C_{12}$ alkenyl;
      4) Substituted $C_2$-$C_{12}$ alkenyl;
      5) $C_2$-$C_{12}$ alkynyl;
      6) Substituted $C_2$-$C_{12}$ alkynyl;
      7) $C_3$-$C_{12}$ cycloalkyl;
      8) Substituted $C_3$-$C_{12}$ cycloalkyl;
      9) Aryl;
      10) Substituted aryl;
      11) Heterocycloalkyl;
      12) Substituted heterocycloalkyl;
      13) Heteroaryl; and
      14) Substituted heteroaryl;
   e) —C(O)O$R_{12}$, where $R_{12}$ is selected from hydrogen or $R_{11}$ where $R_{11}$ as previously defined;
   f) —C(O)$R_{12}$, where $R_{12}$ is as previously defined;
   g) —C(O)N($R_{13}$)($R_{14}$), where $R_{13}$ and $R_{14}$ are independently selected from $R_{12}$ and $R_{12}$ is as previously defined or $R_{13}$ and $R_{14}$, together with the nitrogen atom to which they are attached is substituted or unsubstituted heterocycloalkyl;
   h) —C(O)S$R_{12}$, where $R_{12}$ is as previously defined;
   i) —C(S)O$R_{12}$, where $R_{12}$ is as previously defined;
   j) —C(S)S$R_{12}$, where $R_{12}$ is as previously defined;
   k) —O$R_{12}$, where $R_{12}$ is as previously defined;
   l) —S$R_{12}$, where $R_{12}$ is as previously defined; and
   m) —N$R_{13}R_{14}$, where $R_{13}$ and $R_{14}$ are as previously defined;

$R_3$, $R_4$, $R_5$ and $R_6$ are independently selected from:
   a) Hydrogen;
   b) Deuterium;
   c) $C_1$-$C_{12}$ alkyl;
   d) Substituted $C_1$-$C_{12}$ alkyl;
   e) $C_2$-$C_{12}$ alkenyl;
   f) Substituted $C_2$-$C_{12}$ alkenyl;
   g) $C_2$-$C_{12}$ alkynyl;
   h) Substituted $C_2$-$C_{12}$ alkynyl;
   i) $C_3$-$C_{12}$ cycloalkyl;
   j) Substituted $C_3$-$C_{12}$ cycloalkyl;
   k) Aryl;
   l) Substituted aryl;
   m) Heterocycloalkyl;
   n) Substituted heterocycloalkyl;
   o) Heteroaryl; and
   p) Substituted heteroaryl;
or
$R_3$ and $R_5$, together with the nitrogen atom and the carbon atom to which they are attached, and/or $R_4$ and $R_6$, together with the nitrogen atom and the carbon atom to which they are attached form a substituted or unsubstituted heterocycloalkyl;

$R^a$ and $R^b$ are independently selected from:
   a) Hydrogen;
   b) $R_{11}$;
   c) —C(O)O—$R_{11}$, where $R_{11}$ is as previously defined;
   d) —C(O)NH$R_{11}$, where $R_{11}$ is as previously defined;
   e) $R^a$ and $R^b$ combined together with the N which attached to is substituted or unsubstituted heterocycloalkyl;

$R_7$ is selected from:
   a) $R_{11}$, where $R_{11}$ is as previously defined;
   b) —O$R_{11}$, where $R_{11}$ is as previously defined;
   c) —S$R_{11}$, where $R_{11}$ is as previously defined; and
   d) —N$R_{13}R_{14}$, where $R_{13}$ and $R_{14}$ are as previously defined;

D is selected from:
   a) $C_1$-$C_{12}$ alkylene containing 0, 1, 2 or 3 heteroatoms independently selected from O, S and N;
   b) Substituted $C_1$-$C_{12}$ alkylene containing 0, 1, 2 or 3 heteroatoms independently selected from O, S and N;
   c) $C_2$-$C_{12}$ alkenylene containing 0, 1, 2 or 3 heteroatoms independently selected from O, S and N;
   d) Substituted $C_2$-$C_{12}$ alkenylene containing 0, 1, 2 or 3 heteroatoms independently selected from O, S and N;
   e) $C_2$-$C_{12}$ alkynylene containing 0, 1, 2 or 3 heteroatoms independently selected from O, S and N;
   f) Substituted $C_2$-$C_{12}$ alkynylene containing 0, 1, 2 or 3 heteroatoms independently selected from O, S and N;
   g) $C_3$-$C_{12}$ cycloalkylene;
   h) Substituted $C_3$-$C_{12}$ cycloalkylene;
   i) Heterocycloalkylene; and
   j) Substituted heterocycloalkylene;

E is absent or selected from:
   a) $C_1$-$C_{12}$ alkylene;
   b) Substituted $C_1$-$C_{12}$ alkylene;
   c) $C_3$-$C_{12}$ cycloalkylene;
   d) $C_3$-$C_{12}$ cycloalkylene-M-, where M is selected from optionally substituted $C_1$-$C_{12}$ alkylene, or optionally substituted $C_2$-$C_{12}$ alkenylene, or optionally substituted $C_2$-$C_{12}$ alkynylene, and optionally substituted $C_3$-$C_{12}$ cycloalkylene, each of which contains 0, 1, 2 or 3 heteroatoms independently selected from O, S and N;
   e) Substituted $C_3$-$C_{12}$ cycloalkylene;
   f) Substituted $C_3$-$C_{12}$ cycloalkylene-M, where M is as previously defined;
   g) Heterocycloalkylene;
   h) Heterocycloalkylene-M-, where M is as previously defined;
   i) Substituted heterocycloalkylene; and
   j) Substituted heterocycloalkylene-M-, where M is as previously defined;

L is absent, or selected from:
a) —O—;
b) —N(R$_{12}$)—, where R$_{12}$ is as previously defined;
c) —N(C(O)R$_{11}$)—, where R$_{11}$ is as previously defined;
d) —N(C(O)OR$_{11}$)—, where R$_{11}$ is as previously defined;
e) —S(O)$_n$—, where n=0, 1, or 2;
f) —C(O)—;
g) —C(O)NH—;
h) —OC(O)NH—;
i) —OC(S)NH—;
j) —SC(S)NH—;
k) —NHC(O)NH—;
l) —NHC(S)NH—;
m) —O-M-, where M is as previously defined;
n) —O-M-OC(O)NH—, where M is as previously defined;
o) —S-M-OC(O)NH—, where M is as previously defined;
p) —S(O)$_n$-M-, where n=0, 1 or 2 and M is as previously defined;
q) —OC(O)NH-M-, where M is as previously defined;
r) —OC(S)NH-M-, where M is as previously defined;
s) —NHC(O)NH-M-, where M is as previously defined;
t) —NHC(S)NH-M-, where M is as previously defined;

R$_8$ is R$_{11}$, where R$_{11}$ is as previously defined;
R$_9$ is selected from:
a) Aryl;
b) Substituted aryl;
c) Heteroaryl; and
d) Substituted heteroaryl;

m is 0, 1, 2, 3 or 4.

2. A compound according to claim 1 which is represented by the formula (II):

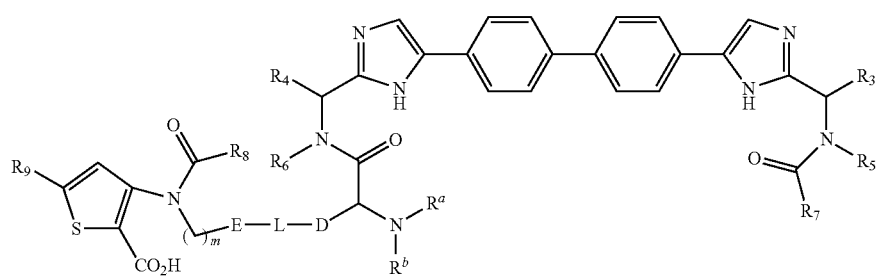

(II)

wherein R$_3$, R$_4$, R$_5$, R$_6$, R$_7$, R$_8$, R$_9$, R$^a$, R$^b$, m, E, L, and D are as defined in claim 1.

3. A compound according to claim 1 which is represented by the formula (III):

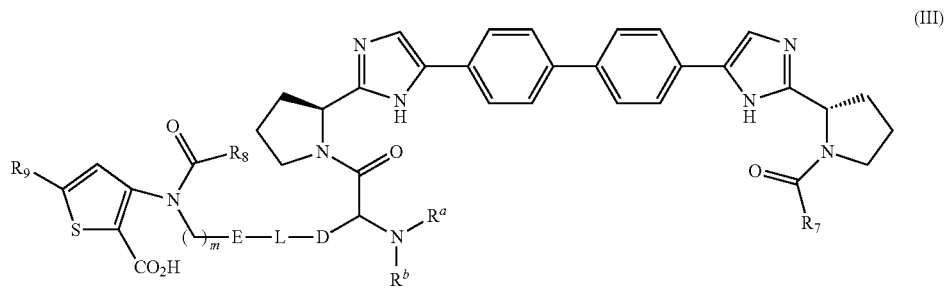

(III)

wherein R$_7$, R$_8$, R$_9$, R$^a$, R$^b$, m, E, L, and D are as defined in claim 1.

4. A compound according to claim 1 which is represented by the formula (IV):

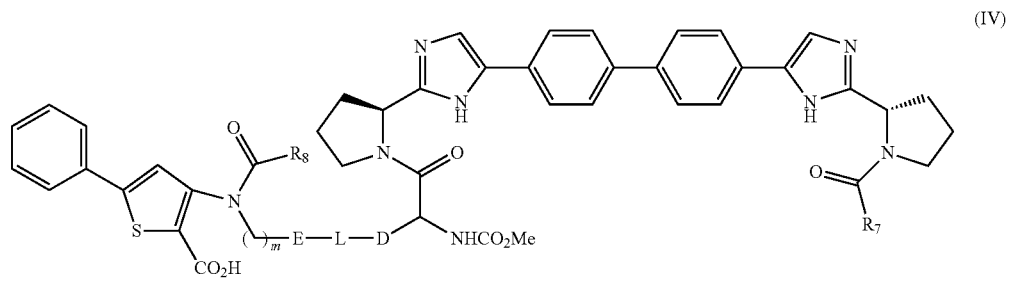

(IV)

wherein R$_7$, R$_8$, m, E, L, and D are as defined in claim 1.

5. A compound of formula (V):
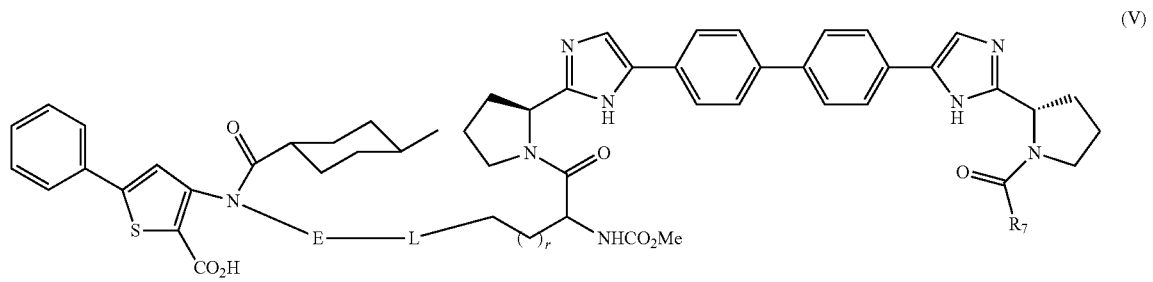
wherein:
E is selected from:
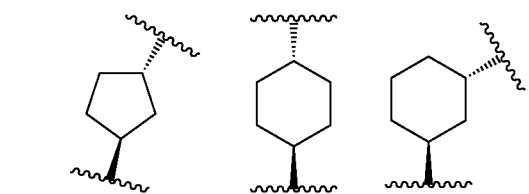
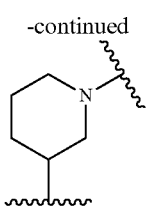
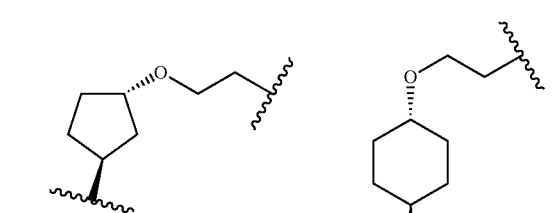
-continued
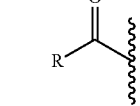
L is selected from: —N(Me)—; —NH—; —N(Boc)-; —N(Ac)-; —OC(O)NH—, —SCH$_2$CH$_2$OC(O)NH—, —OCH$_2$CH$_2$OC(O)NH—;
r is 0, 1, 2, 3, 4 or 5; and
R$_7$C(O)— is selected from the following table:
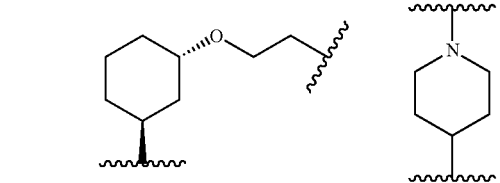
| Entry | 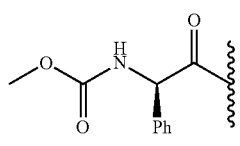 |
|---|---|
| 1 | 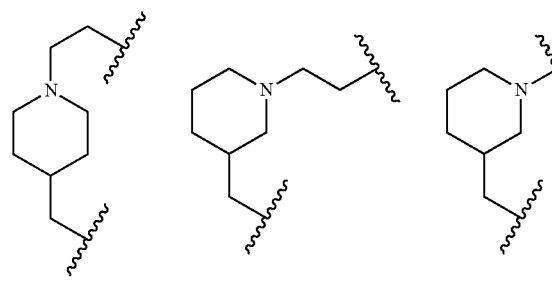 |
| 2 | 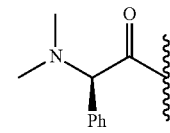 |
| 3 | 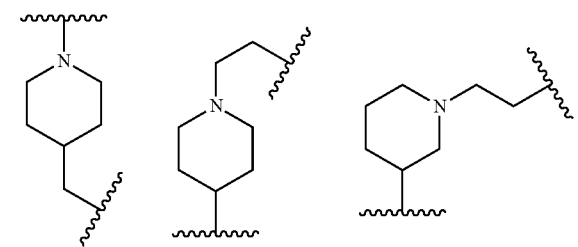 |
| 4 | |
| 5 | 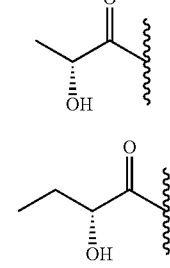 |

| Entry | 135 -continued | | Entry | 136 -continued | |
|---|---|---|---|---|---|
| | 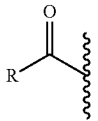 | | | 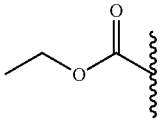 | |
| 6 | 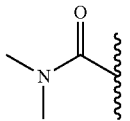 | | 16 | 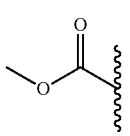 | |
| 7 | 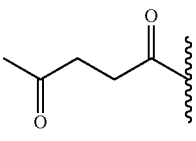 | | 17 | 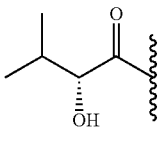 | |
| 8 | 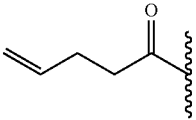 | | 18 | 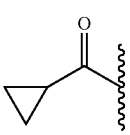 | |
| 9 | 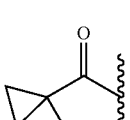 | | 19 | 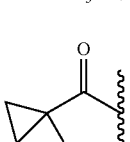 | |
| | | | 20 | 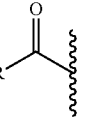 | |
| 10 | 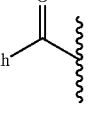 | | | | |
| | | | 21 | 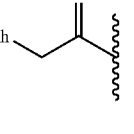 | |
| 11 | 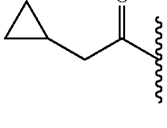 | | | | |
| | | | 22 | 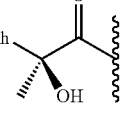 | |
| 12 | 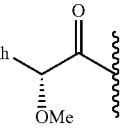 | | | | |
| | | | 23 | 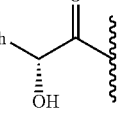 | |
| 13 | 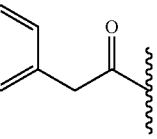 | | | | |
| 14 | 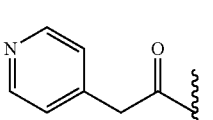 | | 24 | 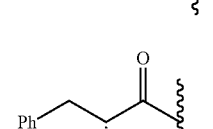 | |
| 15 | 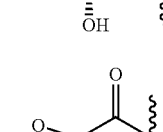 | | 25 | 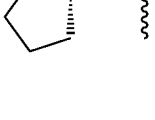 | |

| Entry | R group (137 -continued) |
|---|---|
| 26 | 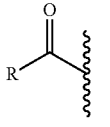 |
| 27 | 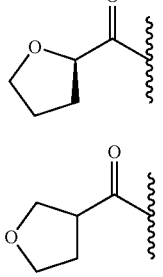 |
| 28 | 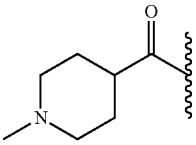 |
| 29 | 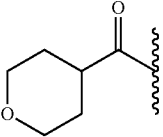 |
| 30 | 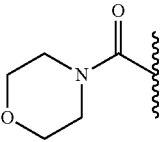 |
| 31 | 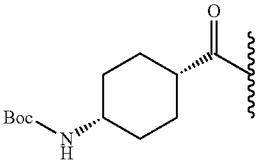 |
| 32 | 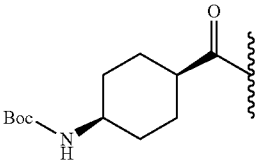 |
| 33 | 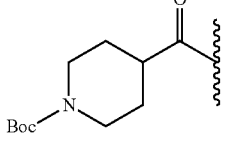 |
| 34 | 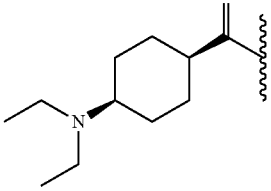 |
| Entry | R group (138 -continued) |
|---|---|
| 35 | 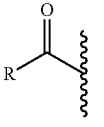 |
| 36 | 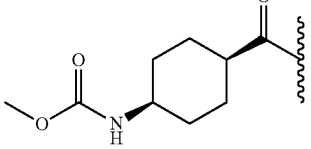 |
| 37 | 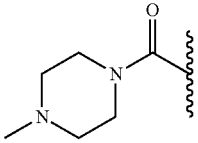 |
| 38 | 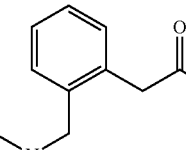 |
| 39 |  |
| 40 | 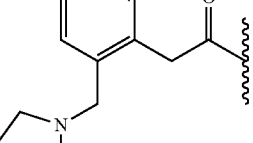 |
| 41 | 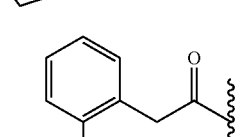 |

| Entry | 139 -continued (R-C(=O)-) | Entry | 140 -continued (R-C(=O)-) |
|---|---|---|---|
| 42 | methyl (trans-4-acylcyclohexyl)carbamate | 51 | 4-(dimethylamino)phenyl ketone |
| 43 | thiazol-4-yl ketone | 52 | pyridin-4-yl ketone |
| 44 | oxazol-2-yl ketone | 53 | pyridin-3-yl ketone |
| 45 | oxazol-5-yl ketone | 54 | pyridin-2-yl ketone |
| 46 | (1H-imidazol-5-yl)methyl ketone | 55 | (S)-1-methoxy-1-phenyl ketone |
| 47 | 1H-imidazol-5-yl ketone | 56 | (R)-2-methoxy-2-phenyl-3,3,3-trifluoro ketone |
| 48 | 1-methyl-1H-imidazol-5-yl ketone | 57 | diphenylmethyl ketone |
| 49 | (1H-tetrazol-5-yl)methyl ketone | 58 | 2-methyl-2-phenylpropanoyl |
| 50 | 2-fluorophenyl ketone | 59 | (R)-2-(2-fluorophenyl)-2-hydroxypropanoyl |

| 141 | 142 |
|---|---|
| -continued | -continued |

TABLE (Entry / structure with R-C(=O)- group):

| Entry | Structure |
|---|---|
| 60 | 1-phenylcyclopropyl ketone |
| 61 | methyl carbamate-Ala ketone |
| 62 | methyl carbamate-Ala (enantiomer) ketone |
| 63 | ethyl carbamate-Ala ketone |
| 64 | tetrahydropyran-4-yl carbamate-Ala ketone |
| 65 | tetrahydropyran-4-yl carbamate-Ala (enantiomer) ketone |
| 66 | methyl carbamate-Ser(OMe) ketone |
| 67 | methyl carbamate-Abu ketone |
| 68 | methyl carbamate-Abu ketone |
| 69 | methyl carbamate, side chain CH2CH2OMe |
| 70 | methyl carbamate-Thr ketone |
| 71 | methyl carbamate-Thr (epimer) ketone |
| 72 | methyl carbamate-Thr(OMe) ketone |
| 73 | methyl carbamate, allyl side chain |
| 74 | methyl carbamate, n-propyl side chain |
| 75 | Boc-NH, side chain CH2CH2NMe2 |
| 76 | methyl carbamate, α,α-dimethyl |

| Entry | Structure |
|---|---|
| 77 | (methyl carbamate, cyclopropyl α-amino ketone) |
| 78 | (methyl carbamate, cyclopropyl α-amino ketone, opposite stereochem) |
| 79 | (methyl carbamate, β-hydroxy-β-methyl) OH |
| 80 | (methyl carbamate), CO₂Bn |
| 81 | (methyl carbamate), CONH₂ |
| 82 | (methyl carbamate, Val) |
| 83 | (methyl carbamate, Val) |
| 84 | (N-methyl methyl carbamate, Val) |

| Entry | Structure |
|---|---|
| 85 | (tetrahydropyran-4-yl carbamate, Val) |
| 86 | (tetrahydropyran-4-yl carbamate, Val) |
| 87 | (tetrahydrofuran-3-yl carbamate, Val) |
| 88 | (methyl carbamate, CH₂CH₂NEt₂) |
| 89 | (methyl carbamate, CH(Me)CH₂OTBS) |
| 90 | (methyl carbamate, CH(Me)CH₂OTBS) |
| 91 | (methyl carbamate, CH₂CH₂NEt₂) |

| Entry | 145 -continued | | Entry | 146 -continued | |
|---|---|---|---|---|---|
| 92 | 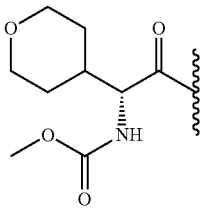 | | 100 | 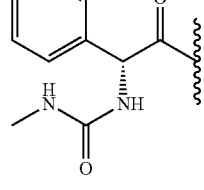 | |
| 93 | 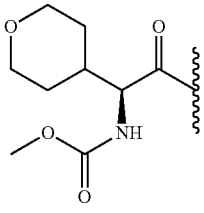 | | 101 | 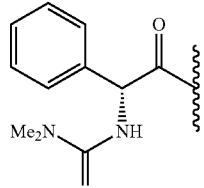 | |
| 94 | 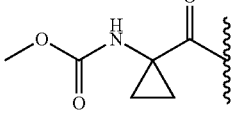 | | 102 | 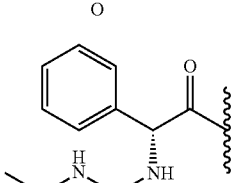 | |
| 95 | 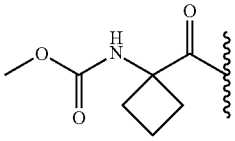 | | 103 | 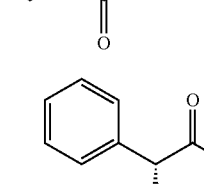 | |
| 96 | 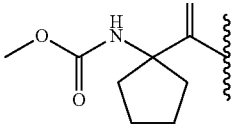 | | 104 | 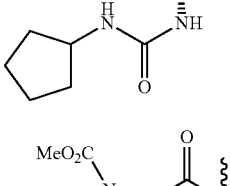 | |
| 97 | 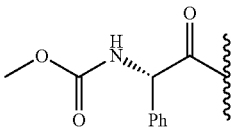 | | 105 | 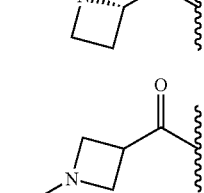 | |
| 98 | 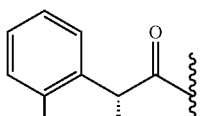 | | 106 | 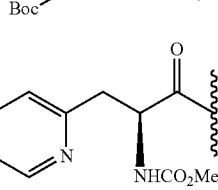 | |
| 99 | 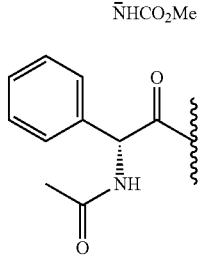 | | 107 | 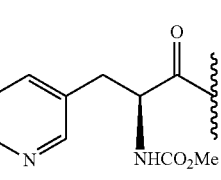 | |

| 147 | 148 |
|---|---|
| -continued | -continued |
| 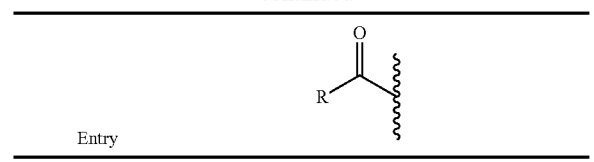 | 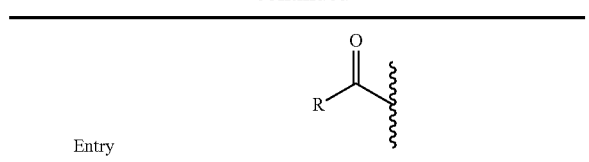 |
| Entry | Entry |
| 108 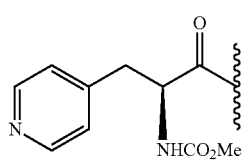 | 115 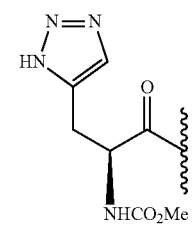 |
| 109 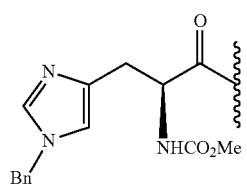 | 116 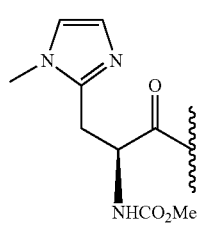 |
| 110 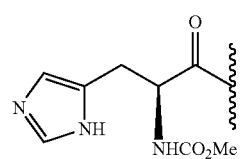 | 117 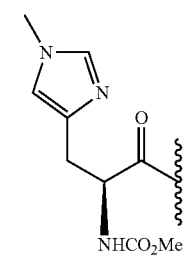 |
| 111 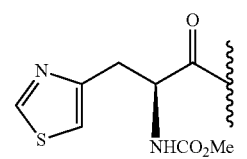 | 118 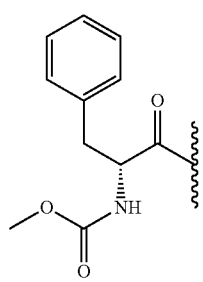 |
| 112 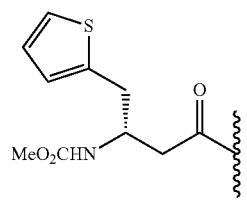 | 119 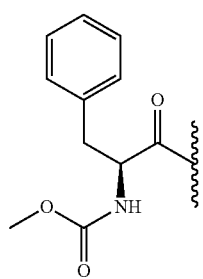 |
| 113 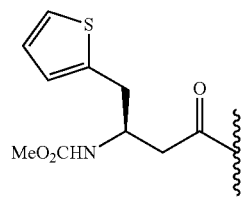 | |
| 114 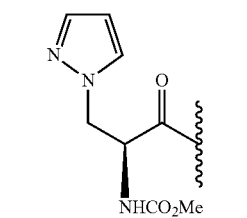 | |

| Entry | R group (149 -continued) |
|---|---|
| 120 | 4-(MeO(HO)P(O)O)-C6H4-CH2-CH(NHCO2Me)-C(O)- |
| 121 | (1H-indol-3-yl)-CH2-CH(NHCO2Me)-C(O)- |
| 122 | 4-(BnO)-C6H4-CH2-CH(NHCO2Me)-C(O)- |
| 123 | 4-(Fmoc-NH-CH2)-C6H4-CH2-CH(NHCO2Me)-C(O)- |
| 124 | (S)-2-oxo-oxazolidin-4-yl-C(O)- |
| 125 | (R)-2-oxo-oxazolidin-4-yl-C(O)- |

| Entry | R group (150 -continued) |
|---|---|
| 126 | (4S,5R)-5-methyl-2-oxo-oxazolidin-4-yl-C(O)- |
| 127 | (1R,2S)-2-(MeO2C-NH)-cyclopentyl-C(O)- |
| 128 | (1S,2R)-2-(MeO2C-NH)-cyclopentyl-C(O)- |
| 129 | (1R,2S)-2-(MeO2C-NH)-cyclohexyl-C(O)- |
| 130 | (1R,3S)-3-(MeO2C-NH)-cyclopentyl-C(O)- |
| 131 | (1S,3R)-3-(MeO2C-NH)-cyclopentyl-C(O)- |
| 132 | (1S,2R)-2-(MeO2C-NH)-cyclohexyl-C(O)- |

-continued

| Entry | |
|---|---|
| 133 | (S)-methyl (1-phenyl-4-oxo...) benzyl carbamate |
| 135 | methyl carbamate benzyl ketone |
| 135 | 2-fluorobenzyl methyl carbamate ketone |
| 136 | MeO-carbamate phenyl ketone |
| 135 | MeO-carbamate phenyl ketone |
| 138 | methyl carbamate phenethyl ketone |

-continued

| Entry | |
|---|---|
| 139 | N-methyl-N-ethyl phenylglycine derivative |
| 140 | N,N-diethyl phenylglycine derivative |
| 141 | N-ethyl-N-cyclopropyl phenylglycine derivative |
| 142 | 7-azabicyclic phenylglycine derivative |
| 143 | 7-azabicyclic phenylglycine derivative |
| 144 | 4-methylpiperazinyl phenylglycine derivative |
| 145 | pyrrolidinyl phenylglycine derivative |
| 146 | 3-fluoropyrrolidinyl phenylglycine derivative |

-continued

| Entry | Structure |
|---|---|
| 147 | (3-fluoropyrrolidin-1-yl)(phenyl)acetyl |
| 148 | (4-phenylpiperidin-1-yl)(phenyl)acetyl |
| 149 | (4-hydroxy-4-methylpiperidin-1-yl)(phenyl)acetyl |
| 150 | (4-hydroxypiperidin-1-yl)(phenyl)acetyl |
| 151 | (2-oxopiperazin-1-yl)(phenyl)acetyl |
| 152 | morpholino(phenyl)acetyl |
| 153 | piperidin-1-yl(phenyl)acetyl |
| 154 | 4-Cbz-piperazin-1-yl(phenyl)acetyl |
| 155 | 2-(dimethylamino)-2-(2-(trifluoromethyl)phenyl)acetyl |

-continued

| Entry | Structure |
|---|---|
| 156 | 2-(dimethylamino)-2-(3-(trifluoromethyl)phenyl)acetyl |
| 157 | 2-(dimethylamino)-2-(pyridin-3-yl)acetyl |
| 158 | 2-(dimethylamino)-2-(pyridin-2-yl)acetyl |
| 159 | 2-(dimethylamino)-2-(pyridin-4-yl)acetyl |
| 160 | 2-(3-chlorophenyl)-2-(dimethylamino)acetyl |
| 161 | 2-(2-chlorophenyl)-2-(dimethylamino)acetyl |
| 162 | 2-(6-chloropyridin-3-yl)-2-(dimethylamino)acetyl |
| 163 | (R)-2-(dimethylamino)-2-(2-fluorophenyl)acetyl |

155
-continued

156
-continued (Tables of chemical structures; not transcribable as text.)

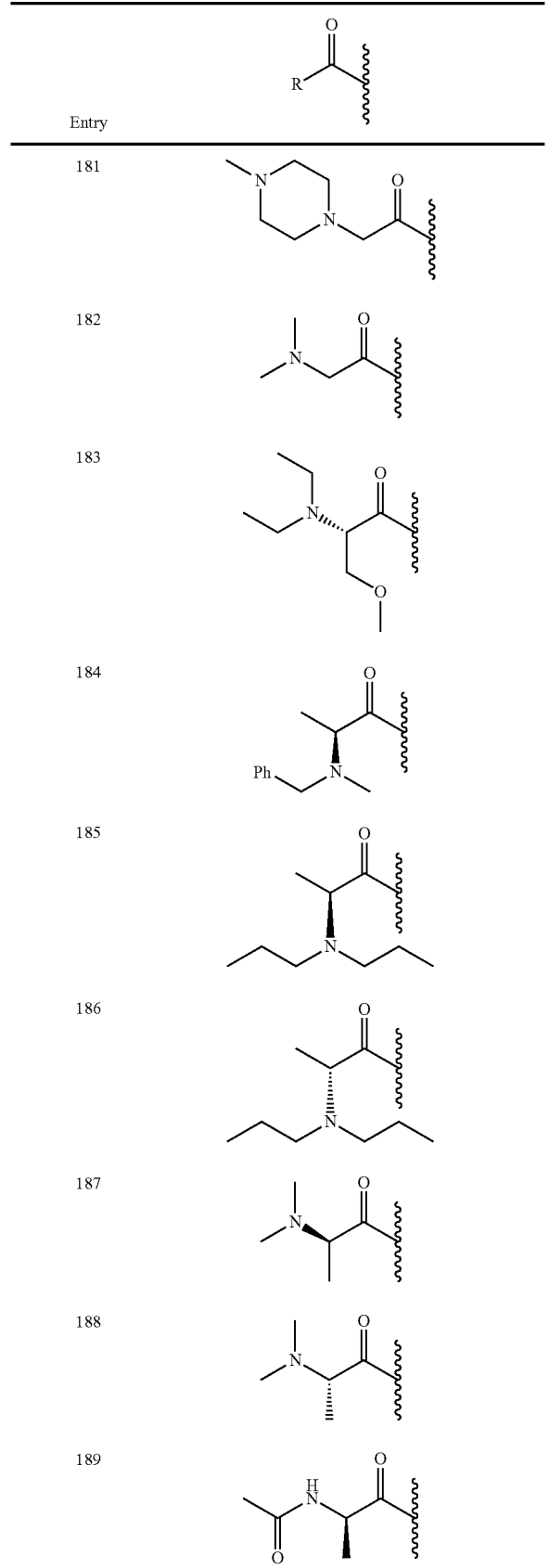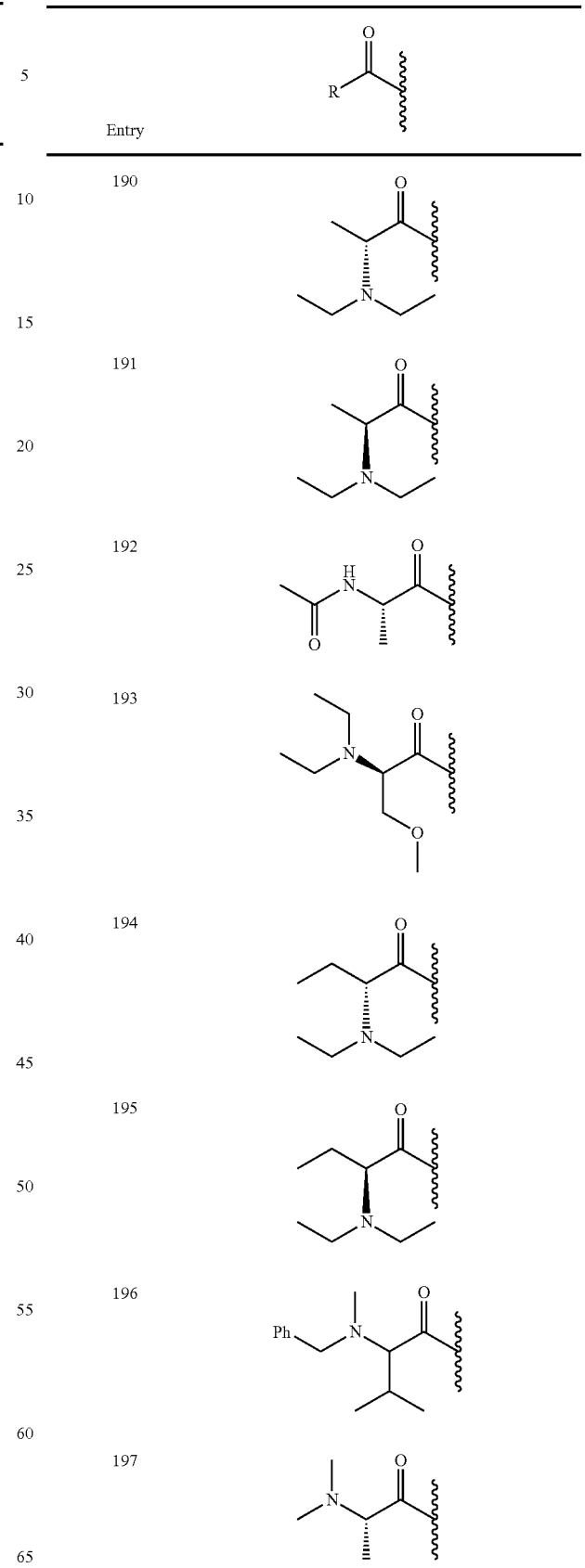

| Entry | R group | | Entry | R group |
|---|---|---|---|---|
| 198 | 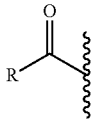 | | 206 | 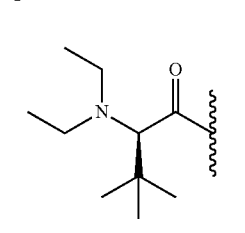 |
| 199 | 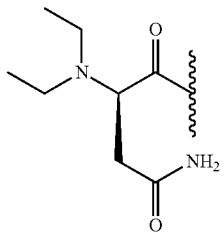 | | 207 | 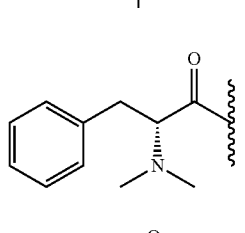 |
| 200 | 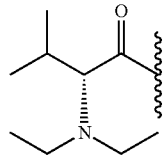 | | 208 | 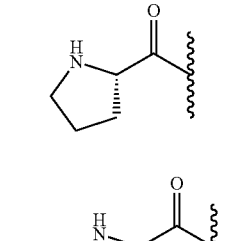 |
| 201 | 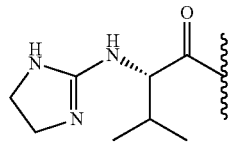 | | 209 | 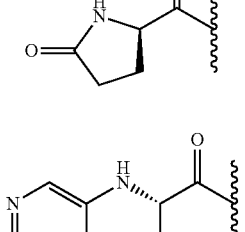 |
| 202 | 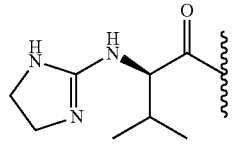 | | 210 | 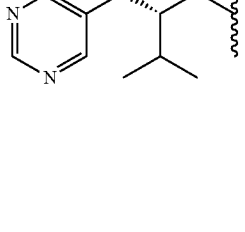 |
| 203 | 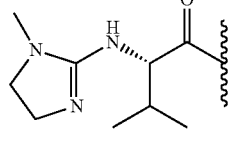 | | 211 |  |
| 204 | 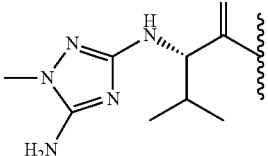 | | 212 |  |
| 205 | 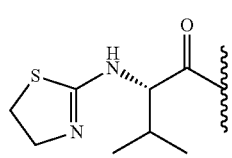 | | 213 |  |

6. A pharmaceutical composition comprising a therapeutically effective amount of a compound of claim 1 or a pharmaceutically-acceptable salt, ester or prodrug thereof, in combination with a pharmaceutically acceptable carrier.

* * * * *